US006372895B1

(12) United States Patent
Bentsen et al.

(10) Patent No.: US 6,372,895 B1
(45) Date of Patent: Apr. 16, 2002

(54) FLUOROGENIC COMPOUNDS

(75) Inventors: James Gregory Bentsen, North Saint Paul; Christopher Allen Mickelson, Saint Paul; Orlin Bruce Knudson, Vadnais Heights; Kevin Michael Lewandowski, Inver Grove Heights, all of MN (US)

(73) Assignee: 3M Innovative Properties Company, St Paul, MN (US)

( * ) Notice: Subject to any disclaimer, the term of this patent is extended or adjusted under 35 U.S.C. 154(b) by 0 days.

(21) Appl. No.: 09/611,686

(22) Filed: Jul. 7, 2000

(51) Int. Cl.$^7$ ................................................ C07G 11/00
(52) U.S. Cl. ...................... 536/4.1; 536/17.2; 536/17.4; 536/18.1; 536/18.4; 530/300; 530/331; 548/100; 548/146; 548/200; 548/202; 548/215; 548/235; 548/300.1; 548/311.7; 548/333.5; 548/335.1; 549/29; 549/30; 549/70; 549/72; 549/218; 549/368; 549/402
(58) Field of Search .................................. 536/4.1, 17.2, 536/17.4, 18.1, 18.4; 530/300, 331; 548/100, 146, 200, 202, 215, 235, 300.1, 311.7, 333.5; 549/29, 30, 70, 72, 218, 368, 402

(56) References Cited

U.S. PATENT DOCUMENTS

| | | |
|---|---|---|
| 4,172,227 A | 10/1979 | Tyrer et al. |
| 4,259,233 A | 3/1981 | Carrico et al. |
| 4,347,935 A | 9/1982 | Merrill |
| 4,591,554 A | 5/1986 | Koumura et al. |
| 4,661,913 A | 4/1987 | Wu et al. |
| 4,667,830 A | 5/1987 | Nozaki, Jr. et al. |
| 5,053,520 A | 10/1991 | Bieniarz et al. |
| 5,093,234 A | 3/1992 | Schwartz |
| 5,144,224 A | 9/1992 | Larsen |
| 5,236,827 A | 8/1993 | Sussman et al. |
| 5,292,840 A | 3/1994 | Heilmann et al. |
| 5,418,167 A | 5/1995 | Matner et al. |
| 5,514,120 A | 5/1996 | Johnson et al. |
| 5,602,202 A | 2/1997 | Groves |
| 5,958,782 A | 9/1999 | Bentsen et al. |

FOREIGN PATENT DOCUMENTS

| | | |
|---|---|---|
| DE | 3540919 A1 * | 5/1987 |
| EP | 0 223 162 | 5/1987 |
| EP | 0 645 382 A1 | 3/1995 |
| WO | WO 92/07899 | 5/1992 |
| WO | WO 96/07268 | 3/1996 |
| WO | WO 96/10747 | 4/1996 |
| WO | WO 96/40980 | 12/1996 |
| WO | WO 98/37802 | 9/1998 |
| WO | WO 99/06589 | 2/1999 |

* cited by examiner

*Primary Examiner*—Kathleen K. Fonda
(74) *Attorney, Agent, or Firm*—Philip Y Dahl

(57) ABSTRACT

Disclosed are novel coumarin based fluorogenic compounds useful in assaying for biological activity. Specifically, these fluorogenic compounds exhibit fluorescence at particular wavelengths when cleaved by target enzymes. Preferred compounds include sugar and peptide derivatives of umbelliferone derivatives bearing a heterocyclic five membered ring at the 3-position. These compounds can be used for rapidly detecting food pathogens and for determining sterilization effectiveness. The compounds may also be used in a form bounded to a polymeric support or to a biomolecule or macromolecule.

17 Claims, 17 Drawing Sheets

FLUOROGENIC COMPOUNDS

FIELD OF THE INVENTION

The present invention relates generally to fluorogenic compounds, including novel fluorogenic compounds suitable for use in biological assays, and to methods of using the flourogenic compounds in biological assays.

BACKGROUND OF THE INVENTION

Fluorogenic and chromogenic enzyme substrates find broad utility in biological detection assays. Many of these substrates are formed by covalently linking a fluorescent or chromophoric dye to a biological molecule that is specific to an enzyme being investigated. Subsequent cleavage of the covalent linkage by the enzyme releases the dye, allowing the fluorescent or calorimetric properties of the dye to be detected visually or measured spectrophotometrically.

The challenge in using this method is finding a fluorophore or chromophore that can satisfy a wide range of conditions for the biological assay of interest. For instance, the fluorescence or the color of the cleaved product should preferably vary from the uncleaved substrate, the background fluorescence and color of the biological sample should not interfere with the detection of the cleaved product, the substrate should be stable to heat and light under the conditions required for the assay, and the substrate should not interfere with the biological activity of the enzyme.

Commonly used substrates include fluorogenic synthetic enzyme substrates derived from coumarin derivatives 4-methylumbelliferone (4-MU) or 7-amino-4-methylcoumarin (7-AMC). MU derivatives have the following structure:

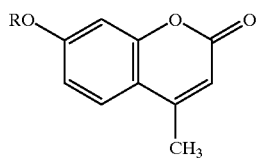

The popularity of these substrates can be ascribed to availability of a wide range of enzyme cleavable R groups. Typical R groups frequently used are esters, monosaccharides, disaccharides, and phosphates. In addition, the fluorogenic synthetic enzyme substrates are popular because of their noncarcinogenicity, ease of visual detection of the products of enzyme activity with UV light sources, autoclave stability, and availability of suitable fluorometers for measurement of fluorescence in both tube and multiwell panels. Enzyme cleavage releases 4-MU, giving rise to fluorescence associated with the 4-MU anion (excitation wavelength of 365 nm, emission wavelength 440 nm). Aryl peptides of 7-AMC are also frequently used as fluorogenic enzyme substrates. The released 7-AMC shows a blue fluorescence (excitation wavelength 370 nm, emission wavelength 440 nm).

Release of 4-MU and 7-AMC can be detected visually as a blue fluorescence when irradiated with a long wavelength UV lamp (for example, $\lambda=360\pm20$ nm). However, at these excitation and emission wavelengths, it is quite common for the biological sample to emit a significant background fluorescence of its own. In other cases, materials employed in making the plate, tube or polymeric support of an assay format can emit a significant background fluorescence. In these cases, low amounts of enzyme activity cannot be detected above background. This common problem adversely affects the sensitivity and speed of many enzyme-linked biological assays.

In contrast, at longer excitation and longer emission wavelengths, background fluorescence drops off dramatically. Therefore, it would be advantageous to develop a class of fluorogenic enzyme substrates that absorb and emit at longer wavelengths (i.e., are red-shifted) than those of the 4-MU- and 7-AMC-based derivatives, without losing the desirable properties of these dyes.

Alternative detection methods do exist. For example, esters, monosaccharides, disaccharides, and phosphates of o-nitrophenol (ONP) or p-nitrophenol (PNP) are frequently used as colorimetric enzyme substrates. Release of nitrophenol gives rise to an increase in absorbence at 405 mn and appearance of a yellow color. The absorbence of these products can be detected using, e.g., a GaN LED source. However, these products are not fluorescent, therefore the sensitivities are far less than 4-MU and 7-AMC derivatives. Aryl peptide derivatives of p-nitroanaline (p-NA) give similar appearance of yellow color. In this case, a substantial increase in sensitivity can be achieved by reacting the p-NA with a diazo dye, yielding blue to dark purple colors. Esters of indoxyl or 5-bromo-4-chloro-3-indolyl give rise to enzyme induced release of indoxyl, to form a blue color, but still do not result in sufficient fluorescence output that allows for more sensitive measurements.

Esters, monosaccharides, disaccharides, and phosphates of fluorescein (FL) and rhodamine (RH) dyes have been developed as fluorogenic enzyme substrates. Release of FL gives rise to an increase in fluorescence associated with the FL anion (excitation wavelength 490 nm, emission wavelength 514 nm). Release of RH gives rise to an increase in fluorescence associated with the RH anion (excitation wavelength 499 nm, emission wavelength 521 nm). The FL and RH anion fluorescences can easily be detected using bulky gas lasers as excitation sources, but there is currently no commercially available solid state light source for these materials. In addition, these classes of enzyme substrates are not typically autoclave stable and therefore are not appropriate for many applications. Finally, the Stokes shift (the difference between the absorbence and emission wavelength) for these materials is far less than that for the 4-MU and 7-AMC materials, requiring the use of more specialized optics to separate the emission signal from the excitation signal.

One particularly relevant application for enzyme substrate indicators is in the detection and differentiation of bacteria. Growing microcolonies will often secrete extracellular enzymes that can convert upwards of a million fluorescent indicator molecules per enzyme molecule. Because the fluorescence detection method is extremely sensitive, this provides a method to amplify the signal from a growing microcolony so that it can be detected in a shorter period of time. For example, a growing microcolony might be detected in 4 to 6 hours using fluorogenic enzyme substrates, whereas the microcolony may be detected in 24 to 48 hours using conventional chromogenic enzyme substrates. This would offer great benefit in the food processing industry, as contaminants could be discovered in eight hours or less.

An example where such methods would be useful is detection of E. coli or coliform. E. coli is an important indicator of fecal contamination in environmental and food samples, while coliform count is an important indicator of bacteriological contamination. In the quality control of water and food, it is highly important to examine both coliforms and *E. coli*. Testing procedures for coliforms commonly employ a 4-MU derivative specific for detecting β-D-galactosidase (β-Gal) activity. This substrate is 4-methylumbelliferyl-β-D-galactoside (MUGal), which is hydrolyzed by β-Gal, liberating blue fluorescent 4-MU. Testing procedures for *E. coli* commonly employ a 4-MU derivative specific for detecting β-D-glucuronidase (β-Gud) activity. This substrate is 4-methylumbelliferyl-β-D-glucuronide (MUGud), which is hydrolyzed by β-Gud, again liberating 4-MU. For selective detection of *E. coli* in primary isolation media, it is common to perform an aerobic incubation in a selective growth medium that inhibits growth of gram-positive strains. In this way, β-Gud activities from strains other than *E. coli* are suppressed. Additionally, incubation at 44° C. and detection of gas formation help in exclusive detection of *E. coli*.

Several MUGud and MUGal testing procedures have been employed for identifying and enumerating total coliforms and *E. coli*. These include most probable number, membrane filtration, presence absence test, agar plate, microtitration plate, paper strip, and related techniques. Because of the thermal stability of these dyes to autoclave, they can be incorporated directly into the growth media before autoclave sterilization. This is an important advantage for commercial test kits, which are sterilized and packaged in the factory.

In a related application, it has been desirable to use the autoclave stability of 4-MU derivatives to develop a biological indicator for monitoring the effectiveness of a sterilization procedure. In this case, a product sold under the trade name Attest™ Rapid Readout Biological Indicator (3M, St. Paul, Minn.) employs *Bacillus subtilis* or *Bacillus stearothermophilus* spores as the active biological agent. These are very resilient spores that are difficult to kill unless the sterilization conditions are rigorous. One way to test for them is to prepare a device containing *Bacillus stearothermophilus* spores in one compartment, and 4-methylumbelliferyl-α-D-glucoside (α-MUGlc) in a second compartment. The device is exposed to autoclave conditions, after which the spores and the enzyme substrate indicator are mixed. If the spores are killed, no 4-MU fluorescence is detected. If the spores are not killed, 4-MU fluorescence is observed to increase. Correspondingly, *Bacillus subtilis* activity is detected in a similar format using 4-methylumbelliferyl-β-D-glucoside (β-MUGlc) as the enzyme substrate indicator.

Another important application area involves the use of fluorogenic enzyme substrates in selective binding assays for clinical diagnostic and high throughput screening applications. In this format, a target biomolecule is detected using a primary or secondary detection reagent (e.g. an antibody or a DNA probe) that has been conjugated to an enzyme. The primary reagent binds selectively to the target. In certain cases, a secondary reagent is added that binds selectively to the primary reagent. After removing unbound reagents, the signal associated with the conjugated enzyme is developed by adding a suitable fluorogenic or chromogenic enzyme substrate. Again, the enzyme acts as an amplifier by cleaving one million or more dye molecules per enzyme molecule.

ELISA assays (Enzyme-Linked Immuno-Sorbant Assays) are one of the most common immunoassay formats used in clinical and research applications. In this case, antibodies bound to a solid support are used to selectively capture the biological target. Next, an enzyme conjugated antibody reporter probe is introduced that binds to the captured targets, forming a sandwich. After rinsing off unbound reporter, fluorescent indicator is introduced to develop the signal. A related assay for nucleic acid detection employs oligonucleotide capture probes bound to a solid support, and enzyme conjugated oligonucleotide reporter probes added to form the sandwich. In addition, enzyme-conjugated detection reagents can also be used to localize a signal in cells or tissue.

Homogeneous immunoassay techniques are generally more rapid and convenient than their heterogeneous counterparts. U.S. Pat. No. 4,259,233 teaches the use of β-galactosyl-umbelliferone-labeled protein and polypeptide conjugates in immunoassays. In these assay formats it is desirable to conjugate a fluorogenic enzyme substrate to a macromolecular substrate identical to the biological target molecule under assay. In this case, the sample target and conjugated target (having the fluorogenic enzyme substrate) compete for binding to a fixed pool of antibodies. Once the antibodies bind to the conjugated target, they inhibit access of added β-Gal enzyme, and the fluorogenic enzyme target is protected from cleavage. As the amount of sample target increases, the number of antibodies available to protect the conjugate target decreases, and the fluorescent signal from enzymatically cleaved conjugate increases.

Enzyme fragment recombination offers an alternative approach to homogenous assays. Genetically engineered fragments of β-galactosidase enzyme derived from *E. coli* are known to recombine in vitro to form active enzyme. This reaction can be used as a homogeneous signaling system for high-throughput screening. In this type of assay, a biological ligand such as a drug is conjugated to one of the enzyme fragments. The ligand alone does not adversely affect enzyme fragment recombination. However, if an antibody, receptor or other large biomolecule is added that specifically binds to the ligand, enzyme fragment recombination is sterically impeded and enzyme activity is lost. Receptor binding efficiency to the ligand is determined from the kinetics of enzymatic cleavage of added fluorogenic enzyme substrate. Again, enzymatic amplification is achieved by measuring the signal produced by the action of enzyme on fluorogenic compounds such as MUGal.

Thus, there is a need to develop new enzyme-linked assay formats that employ very small sample sizes, such as assays performed in microwell arrays, on microfluidic chips, and on the surface of micron scale bead carriers. There is also a need to develop rapid, compact, high-sensitivity readers that can detect and quantify the enzyme-linked fluorescent response. It would be highly desirable to interrogate the fluorescent response in these formats using inexpensive and compact solid state light sources, instead of bulky lamp sources. However, there is currently no solid state light source that can excite the 4-MU and 7-AMC products. It would be advantageous to develop a class of fluorogenic enzyme substrates that are spectrally compatible with a solid state light emitting diode or laser diode source. Also, in some of these applications, a need remains for improved fluorogenic enzyme substrates that are red-shifted, LED or laser diode compatible, and autoclave stable.

SUMMARY OF THE INVENTION

The present invention is directed to coumarins bearing, at the 7-position, an enzymatically-cleavable group and, at the 3-position, a 5-membered heterocyclic ring, wherein the coumarins are useful as fluorogenic enzyme substrates (FES) conveying improved properties for rapid microbial detection applications. Specifically, the coumarin-based FES so modified are substantially red-shifted in absorbence with respect to traditional 4-MU derivatives, making them compatible with the use of GaN LED and laser diode excitation sources having $\lambda_{emission}$ in the range of 390 to 540 nm. Furthermore, these molecules are typically autoclave stable, making them compatible with a variety of biological indicator assay formats for sterilization monitoring, sterilization processes applied in the manufacture of biological assay kits and materials, and laboratory protocols for sterilization of growth media and other materials used in biological research. In addition, in certain implementations, the pKa of the enzymatically cleaved products can be modulated in the range of 6.1 to 7.6 for a wide range of biological assays which perform optimally at or near physiological pH. The modulation is performed based upon the choice of the five membered heterocyclic substituents.

Accordingly, the present invention includes a fluorogenic compound of Formula (I), provided below:

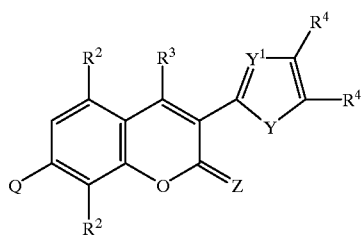

Formula (I)

wherein Q is selected from the group consisting of a glycone, a glycosyl phosphate, an ester, and a peptide; each $R^2$ independently is a sterically non-interfering group; $R^3$ is an electron withdrawing or non-electron withdrawing group; Z is O or $NR^5$, wherein $R^5$ is hydrogen or a hydrocarbyl-containing group; Y and $Y^1$ independently are O, S, $NH_x$, or $CH_y$, where x is 0 or 1 and y is 1 or 2, with the proviso that at least one of Y and $Y^1$ is O, S, or $NH_x$; and each $R^4$ independently is selected from the group consisting of hydrogen, halogen, a $C_1$–$C_{20}$ alkyl, a $C_1$–$C_{20}$ alkoxy, a $C_3$–$C_{18}$ cycloalkyl, a $C_6$–$C_{18}$ aryl, a $C_6$–$C_{18}$ aryloxy, a $C_6$–$C_{18}$ hydroxyaryl $C_6$–$C_{18}$ arylcarboxy, a $C_6$–$C_{18}$ carboxyaryl, a $C_2$–$C_{18}$ alkenyl, a $C_1$–$C_{20}$ hydrocarbylamino, a $C_6$–$C_{18}$ arylamino, a $C_6$–$C_{18}$ aminoaryl, a $C_2$–$C_{20}$ di(hydrocarbyl)amino, a heterocyclic group having at least three ring atoms, carboxyl, carboxamide, ester, keto-alkyl ester, sulfonic acid, amino, a pendant biological ligand such as a protein or polypeptide of molecular weight between 130 and 10,000,000, and, more specifically, an immunoglobulin, and a group of the formula $(CH_2A)_aE$ in which A is O, NH, or a single bond, E is a functional group that includes active hydrogen, and a is a whole number from 1 to 100, preferably from 1 to 25, and more preferably 1 to 10; or both $R^4$ groups together with the carbon atoms to which they are attached form a 5- or 6-membered aromatic ring which optionally can have one or more $R^4$ groups attached; or a salt thereof. Where this molecule is to be covalently attached to a support or a biological ligand, at least one of $R^2$, $R^3$, and $R^4$ typically includes a group having an active hydrogen.

In one embodiment, the present invention teaches a class of coumarin based fluorogenic enzyme substrates (FES). When the enzymatically hydrolyzable group on the fluorogenic substrate is selectively hydrolyzed by an enzyme, the properties of the fluorophor change in such a way that the enzyme activity can be detected visually through a color change or through a change in fluorescence. Further, the enzyme activity can be quantified for a particular sample by fluorometric or colorimetric analysis.

In a preferred embodiment, substituent groups and their positions on the coumarin ring have been chosen so as to ensure that the excitation (i.e. absorption) maximum of the enzymatically cleaved product is centered at a wavelength greater than 380 nm. This allows the ionophore of the present invention to be used with certain solid state light sources such as, for example, blue LEDs and lasers. Substituent groups and their positions are also preferably chosen to keep the pKa of the cleaved product below pH 7.6 so that the deprotonated fluorogenic cleavage product is present in detectable amounts when using the fluorogenic substrates in biological assays. Finally, substituent groups and their positions are preferably chosen to provide the option for covalent attachment to polymeric or ceramic supports, oligomers, biopolymers, biological ligands such as proteins and polypeptides, and the like. Preferably, the material to which the indicator is attached is chosen to support uniform and reproducible enzymatic response.

Another aspect of the present invention is found in a composite structure having a polymeric support and the fluorogenic compound of formula (I) bonded to the support through at least one of $R^2$, $R^3$, and $R^4$ by means of either a bond or a linking group, the linking group having functionalities at both ends, wherein the functionality at one end of the linking group is complementary to the functionality of $R^2$, $R^3$ or $R^4$ and the functionality at the other end is complementary to a functional group on the support.

The polymeric support can be in the form of a sensor disk, a polymeric fiber or microwell, or a component on the surface of a carrier bead suitable for interrogation by, for example, flow cytometry or microscopy. Suitable coupling agents for covalent attachment are described in U.S. Pat No. 5,053,520, which is herein incorporated in its entirety by reference. Homobifunctional and/or heterobifunctional coupling agents are described in PCT Pat. App. Nos. WO 96/07268 and WO 96/10747, also incorporated herein by reference in its entirety.

Still another aspect of the present invention is found in a fluorogenic macromolecular conjugate having a molecular ligand or macromolecular ligand and the fluorogenic compound of Formula (I) covalently linked through at least one $R^2$, $R^3$, and $R^4$ by means of one of a bond and a linking group, the linking group having functionalities at both ends, wherein the functionality at one end of the linking group is complementary to the functionality of $R^2$, $R^3$, or $R^4$, and the functionality at the other end is complementary to a functional group on the ligand.

In a further aspect, the present invention provides a sensing system that comprises a sensing element and an excitation assembly, wherein the sensing element comprises at least one of the fluorogenic enzyme substrates and a fluid handling architecture structured and adapted to support mixing or otherwise intimate interaction of one or more enzyme-containing samples with at least one of the fluorogenic enzyme substrates to enable enzymatic reaction to form a cleaved fluorescent product which, when exposed to light of a wavelength range centered around $\lambda_1$, is capable of emitting light of a wavelength range centered around $\lambda_2$, wherein $\lambda_1$ is at least 10 nm greater than $\lambda_1$, $\lambda_2$, is at least about 380 nm, more preferably at least about 425 nm, and most preferably at least about 450 nm. In one preferred embodiment, the excitation assembly comprises solid state GaN, InGaN, ZnSe, or SiC LED or laser diodes which excite the sensing element(s) at or near wavelength $\lambda_1$ for a time sufficient for the cleaved product to emit visible light of wavelength $\lambda_2$.

In specific implementations, a detection assembly is positioned and adapted to detect the intensity or location of emitted signal(s) centered at $\lambda_2$ from the sensing element. The output from the detection assembly is typically converted to a digital signal by an analog to digital (A/D) converter and transmitted to the processor assembly. A processor assembly is positioned and adapted to process and analyze the emitted signal(s) in determining the concentration, location, or enumeration of biomolecules, bio-macromolecules, or microorganisms. This processor assembly may be part of a stand-alone unit or may be part of a central computer or local area network. Optionally, the processor assembly may contain a relational data base which correlates the processed data for each sensing element with corresponding identifiers for samples or articles, e.g., a food sample, a drug sample, a clinical sample, a sterilized article, etc.

In one embodiment, the excitation and detection assemblies are integrated using bifurcated fiber-optics that direct light of wavelength $\lambda_1$ from an LED to one or more sensing elements or simultaneously to sensing elements and a reference channel. Return fibers direct emitted signals of wavelength $\lambda_2$ from the sensing elements and reference channels to optical detectors for analysis by the processor.

In a second embodiment, the excitation and detection assemblies are integrated using a beam splitter assembly and focusing optical lenses that direct light of wavelength $\lambda_1$ from an LED to a single location on a sensing element and direct emitted light of wavelength $\lambda_2$ from the sensing element to an optical detector for analysis by the processor. In this embodiment, the measurement can be made at one point on the sensing element, as for example in detecting emission from a cuvette, sensor disk, or a channel within a microfluidic chip. Also, the measurement can be made at multiple locations on the sensing element by moving or raster scanning the sensing element including a point light source and focusing optical lenses with respect to one another, as for example in detecting emission from multiple growing microcolonies on a planar growth medium configured to absorb a fluid sample containing viable microorganisms and to support the growth of the viable microorganisms, such as Petrifilm™ (3M, St. Paul, Minn.). In this case, the processor assembly optionally analyzes data from these multiple points on the sensing element to determine the concentration, location, or enumeration of the biomolecules, bio-macromolecules, or microorganisms corresponding to that sample.

In a third embodiment, the excitation and detection assemblies are integrated as a scanner comprising a bank of LED's or other suitable light sources adjacent to a CCD camera chip. The LED's direct light of wavelength $\lambda_1$ to an area on the sensing element. The CCD camera collects emitted light of wavelength $\lambda_2$ and provides a fluorescent image of the defined area to the processor for analysis. In this case, the processor is adapted to interpret the image in determining the concentration, location, enumeration or identity of the biomolecules, bio-macromolecules, or microorganisms corresponding to that sensing element. In some applications, it is desirable to print biological components in a predefined pattern such as a logo, indicia, barcode, or array and to interpret the resulting image after exposure to the fluorogenic enzyme substrate. For example, a microwell array may contain a panel of different drug candidates to be screened by an assay that involves using the fluorogenic enzyme substrate as an indicator. Or, a panel of several biological receptors may be printed on a support, exposed to a biological sample, and developed using a fluorogenic enzyme substrate. The resulting fluorescent image can be analyzed by the processor using image recognition software designed to orient, scale, and enhance the image so that it conforms to a standard form that can be interpreted.

In a further aspect, the present invention provides a method of detecting the presence of enzymatic activity comprising the steps of (a) contacting a fluorogenic enzyme substrate with an enzyme-containing medium and allowing or providing a means for the enzyme to act on the enzyme substrate (e.g., through diffusion) to release some or all of the cleaved fluorescent product, which when exposed to light of a wavelength range centered around $\lambda_1$ is capable of emitting light of a wavelength range centered around $\lambda_2$, wherein $\lambda_2$ is at least 10 nm greater than $\lambda_1$, $\lambda_1$ is at least about 380 nm, more preferably at least about 425 nm, and most preferably at least about 450 nm; and (b) interrogating the cleaved product with light of a wavelength range centered around $\lambda_1$ for a time sufficient for the product to emit visible light of wavelength $\lambda_2$ which is collected and detected. By means of suitable analysis algorithms, the amount, location, or rate of change of the emitted light can be correlated with the concentration or enumeration of biomolecules, biomacromolecules, or microorganisms in the enzyme-containing medium. Alternatively, the fluorogenic enzyme substrate can be located throughout the growth medium and the enzyme-containing sample can be contacted therewith. Diffusion of the enzyme into the medium allows the enzyme to act on the enzyme substrate to release some or all of the cleaved fluorescent product, and the light emitted therefrom is subsequently detected and analyzed, as described above.

BRIEF DESCRIPTION OF THE DRAWINGS

FIG. 17b shows a plot of initial rates of reaction vs. enzyme concentration derived from the fluorescence response data shown in FIG. 17a.

DETAILED DESCRIPTION OF THE INVENTION

Figure 1A:
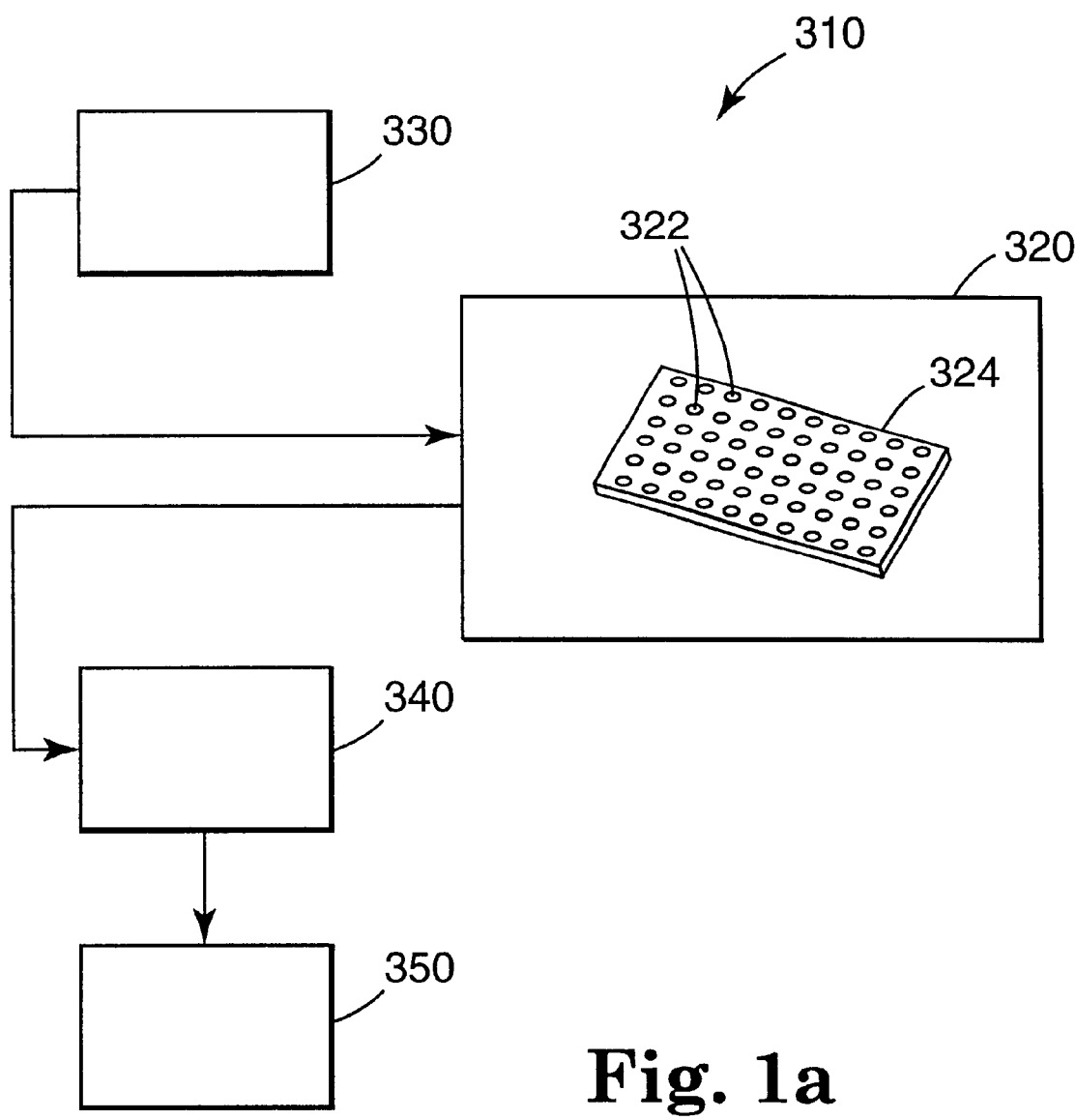
FIG. 1a shows a schematic diagram of a representative sensing system of the invention.

These definitions are used throughout this application.

The term "fluorogenic enzyme substrate" (FES) refers to a material that is selectively hydrolyzable by an enzyme to generate a fluorescently detectable product when cleaved.

The term "chromogenic enzyme substrate" refers to a material that is a selectively hydrolyzable by an enzyme to generate a chromometrically or colorimetrically detectable product when cleaved.

The term "fluorescent compound" refers to a material which fluoresces, or emits light, in passing from a higher electronic state to a lower electronic state in a short period of time in response to an exciting light signal.

The term "fluorogenic compound" refers to those compounds comprising a fluorescent compound bound to a cleavable group.

The term "enzymatically hydrolyzable linkage" refers to a linkage or bond that can easily be cleaved by an enzyme; particularly an enzyme of interest.

The term "sterically non-interfering" refers to substituent groups which are not of sufficient size or three dimensional shape to interfere with the enzyme's ability to cleave the linkage or bond.

The term "electron withdrawing group" refers to an atom or substituent group that has a relatively high electronegativity, or an ability to acquire electrons from other atoms or groups. Halogens, oxygen and sulfur are the most electronegative elements for purposes of the present invention.

The term "non-electron withdrawing group" refers to atoms or substituent groups with relatively low electronegativity. For example, hydrogen is a non-electron withdrawing group.

The term "stable (or stability) to steam sterilization (or autoclave) conditions" refers to the ability of a chemical compound to withstand a temperature of about 121° C. for at least 5 minutes, preferably for about 20 minutes, at a relative humidity of 100%, without degradation, including breaking of any chemical bonds.

Fluorogenic enzyme substrates are used in a wide variety of applications to assay for biological activity. Typically, a fluorescent dye is joined to a biological molecule of interest, which is cleavable, by an available enzyme. Subsequent cleavage by the enzyme releases the dye, allowing its detection by a change in fluorescence or color. The invention involves novel fluorogenic compounds of Formula (I):

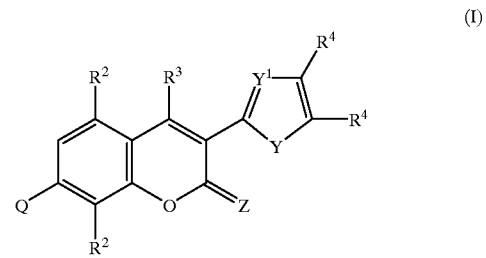

(I)

where the substituent groups are as previously defined. For example, 3-(2-thienyl)-umbelliferyl-β-D-galactoside can undergo hydrolysis via β-galactosidase to yield 3-(2-thienyl)-umbelliferone and β-D-galactose, as seen in Sequence (1):

Sequence 1

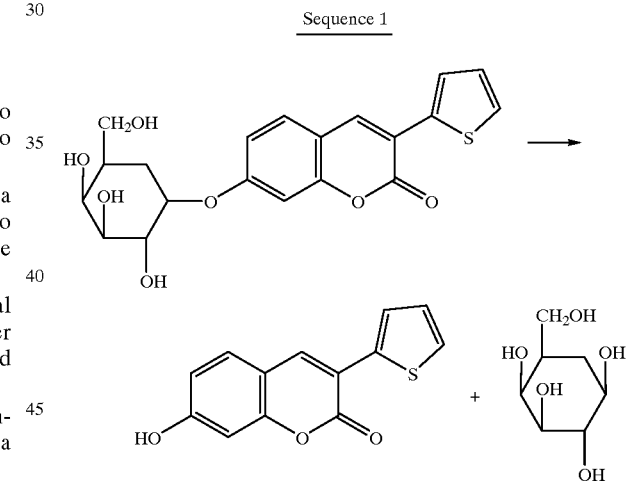

Sequence (1) shows the hydrolysis of a particular FES. Deprotonation of the cleaved product near neutral pH yields a 3-(2-thienyl)umbelliferyl anion which absorbs light near 450 mn and emits light near 500 nm. These wavelengths enable visualization using a filtered GaN, SiC or ZnSe LED light source.

Fluorescence Characteristics

In specific implementations, an important factor in developing a useful indicator dye is to red-shift the absorption and emission of the dye without losing the large Stokes shift (the difference between the absorbence and emission wavelength) and while providing high spectral resolution. In the present invention, enzymatic hydrolysis of 3-(2-thienyl)-umbelliferyl-β-D-galactoside (β-TUGal) yields the products 3-(2-thienyl) umbelliferone and β-D-galactose (Sequence 1). Importantly, β-TUGal and β-TUG1c display absorption and emission maxima at 380 and 450 nm, respectively while the 3-(2-thienyl)-umbelliferone anion product exhibits absorption and emission maxima at 450 nm and 502 nm respectively. The large shift in both the excitation and emission wavelengths, relative to MU and MUGal, confers excellent performance as a fluorogenic enzyme substrate.

For bacterial detection, the sample can be excited at 450 nm using a compact GaN LED light source. β-TUGal or β-TUGlc do not absorb at this wavelength and therefore do not fluoresce. However, as the 3-(2-thienyl) umbelliferone product forms, emission is observed at 502 nm. Because the enzyme substrates have no background fluorescence at this wavelength, very small amounts of hydrolysis product can be detected. Also, because these dyes can be excited with pulsed or modulated solid state light sources, system noise can be greatly reduced. These two factors offer the potential for greatly improved sensitivity and rapid detection.

Another important factor in developing a useful indicator is to choose a red-shifting substituent at C-3 that supports a relatively low pKa for the umbelliferone hydrolysis product, such that the spectroscopically distinct anion form is present at physiological pH. This feature allows for continuous measurement of enzymatic activity, which the use of MUG does not offer.

The following list gives representative examples of hydrolysis products and shows how their properties can be manipulated to provide desirable properties for biodetection applications.

| Compound | $\lambda_{ex}$ (nm) | $\lambda_{em}$ (nm) | $pK_a$ |
|---|---|---|---|
| 3-(2-thienyl) umbelliferyl anion | 410 | 502 | 7.57 |
| 3-(2-benzothiazolyl) umbelliferyl anion | 447 | 488 | 6.79 |
| 3-(2-benzoxazolyl) umbelliferyl anion | 425 | 471 | 6.56 |
| 3-(2-benzoimidazolyl) umbelliferyl anion | 420 | 477 | 7.01 |

Compounds

The invention involves novel compounds of Formula (I) as defined above. In one embodiment, each $R^2$ is independently selected from the group consisting of hydrogen, halogen, a $C_1$–$C_{20}$ alkyl, a $C_1$–$C_{20}$ alkoxy, a $C_2$–$C_{18}$ alkenyl, a $C_1$–$C_{20}$ hydrocarbylamino, a $C_2$–$C_{20}$ di(hydrocarbyl) amino, and a functional group having the formula $(CH_2A)_aE$ in which A is O, NH, or a single bond, E is a functional group that includes active hydrogen, and a is a whole number from 1 to 100, preferably from 1 to 25, and more preferably 1 to 10. Examples of the functional group are an amine, amide, ester, oxirane, olefin, urea, silanol, carbamate, isocyanate, thioisocyanate, sulfonamide, sulfonyl chloride, sulfonic acid, carboxylic acid, carboxyl, chlorotriazine, hydrazine, hydrazide, or aldehyde.

$R^3$ is preferably selected from the group consisting of hydrogen, a $C_1$–$C_{20}$ alkyl, a $C_3$–$C_{18}$ cycloalkyl, a $C_6$–$C_{18}$ aryl, a $C_6$–$C_{18}$ aryloxy, a $C_6$–$C_{18}$ hydroxyaryl, a $C_6$–$C_{18}$ arylcarboxy, a $C_6$–$C_{18}$ carboxyaryl, a $C_2$–$C_{18}$ alkenyl, a $C_2$–$C_6$ alkynyl, a halogen selected from the group consisting of F, Cl, Br, and I, a $C_1$–$C_4$ haloalkyl, a cyano, a $C_1$–$C_6$ cyanoalkyl, a carboxylate, a $C_1$–$C_6$ carboxylalkyl, and a group having the formula $(CH_2A)_aE$ in which A, E, and a are defined as above. In another embodiment, compounds of Formula (I) may be further defined in that Z is O or $NR^5$, where $R^5$ is hydrogen or a $C_1$ to $C_4$ alkyl group. Preferably, each $R^2$ and $R^3$ is hydrogen.

Preferably, compounds of Formula (I) may be further defined in that each $R^4$ is independently selected from the group consisting of hydrogen, halogen, carboxyl, carboxamide, ester, keto-alkyl ester, sulfonic acid, amino, and a group of the formula $(CH_2A)_aE$ in which A is O, NH, or a single bond, E is a functional group that includes active hydrogen, and a is a whole number from 1 to 100, preferably from 1 to 25, and more preferably 1 to 10; or both $R^4$ groups together with the carbon atoms to which they are attached form a 6-membered aromatic ring which optionally may have one or two $R^4$ groups attached.

In a preferred embodiment, compounds of Formula (I) may be further defined in that Z is O; each $R^2$ and $R^3$ is hydrogen; and each $R^4$ is independently selected from the group consisting of hydrogen, halogen, carboxyl, carboxamide, ester, keto-alkyl ester, sulfonic acid, amino, and a group of the formula $(CH_2A)_aE$ in which A may be O, NH, or a single bond, E is a functional group that includes active hydrogen, and a is a whole number from 1 to 100, preferably from 1 to 25, and more preferably 1 to 10; or both $R^4$ groups together with the carbon atoms to which they are attached may form a 6-membered aromatic ring which optionally may have one or two $R^4$ groups attached.

In addition to the substituent groups on the coumarin moiety as defined above (e.g., $R^2$ and $R^3$), compounds of the present invention include enzymatically hydrolyzable groups. In broad terms, it is preferred that the hydrolyzable linkage or group, Q, includes a glycone, a glycosyl phosphate, an ester, or a peptide.

Q can be a glycone or glycosyl phosphate such as one selected from the group consisting of α- and β-D-galactopyranosyl, α- and β-D-glucopyranosyl, N-acetyl-α- and β-D-galactosaminyl; N-acetyl-α- and β-glucosaminyl; β-D-glucuronyl, α-L-arabinopyranosyl, α-L-arabinofuranosyl, β-D-facopyranosyl, α- and β-L-fucopyranosyl, α-D-mannopyranosyl, β-D-xylopyranosyl, α-D-maltosyl, β-D-lactopyranosyl, β-D-cellobiosyl, α-D-N-acetylneuraminyl, and myoinositol-1-yl phosphate. More preferably, Q is α- or β-D-galactopyranosyl, α- or β-D-glucopyranosyl, or β-D-glucuronyl. In a more preferred embodiment, Z is O and Q is β-D-galactosyl or β-D-glycosyl.

Q may be a carboxy terminal-linked amino acid or an acid addition salt thereof. Such amino acids typically include N-acetyl-L-lysine, L-alanine, L-arginineL-aspartic acid, N-alpha-benzyloxycarbonyl-L-arginine, L-citrulline, gamma-L-glutamic acid, L-glycine, L-histidine, L-hydroxproline, L-isoleucine, L-leucine, L-lysine, L-methionine, L-ornithine, L-phenylalanine, L-proline, L-pyroglutamic acid, L-serine, L-tryptophan, L-tyrosine, and L-valine.

Q may also be a carboxy terminal-linked peptide having 1 to 4 amino acids or an addition salt thereof. Such peptides typically include L-arginyl-L-arginine, N-benzyloxycarbonyl-glycyl-L-proline, L-glutaryl-glycyl-arginine, glycyl-glycine, glycyl-L-phenylalanine, glycyl-L-proline, and L-seryl-L-tyrosine.

More preferably, Q is a carboxy terminal-linked peptide having 1 to 4 amino acids, wherein free amino groups optionally have a protective group, or an acid addition salt thereof.

Q may also be an ester, such as one selected from the group consisting of butyrate, valerate, hexanoate, caprylate, octanoate, nonanoate, and palmitate.

In a preferred embodiment, each moiety Q, Z, Y, $Y^1$, $R^2$, $R^3$, and $R^4$ is chosen such that the specific chemical compound in Formula I is stable to steam sterilization conditions.

Composite Structure

The fluorogenic compounds described by Formula (I) can be used in an enzyme sensing composite structure which include a support; wherein the compound of Formula (I) is covalently bound to the support through at least one of $R^2$, $R^3$ or $R^4$ by means of one of a bond and a linking group, the linking group having functionalities at both ends, the functionality at one end of the linking group being complementary to the functionality of $R^2$, $R^3$ or $R^4$ and the functionality at the other end being complementary to a functional group on the support. Typical functionalities of the linking moiety include amine, amide, ester, oxirane, olefin, urea, silanol, carbamate, isocyanate, thioisocyanate, sulfonamide, sulfonyl chloride, sulfonic acid, carboxylic acid, carboxyl, chlorotriazine, hydrazine, hydrazide, or aldehyde.

The fluorogenic compound used in the composite structure can be further defined in that Z is O, each $R^2$ and $R^3$ is hydrogen, and each $R^4$ is independently selected from the group consisting of hydrogen, halogen, carboxyl, carboxamide, ester, keto-alkyl ester, sulfonic acid, amino, and a group of the formula $(CH_2A)_aE$ in which A is O, NH, or a single bond, E is a functional group that includes active hydrogen, and a is a whole number from 1 to 100, preferably from 1 to 25, and more preferably 1 to 10; or both $R^4$ groups together with the carbon atoms to which they are attached form a 6-membered aromatic ring which optionally has at least one $R^4$ groups attached.

In a preferred embodiment, the fluorogenic compounds of Formula (I) used with the composite structure are further defined in that Z is O and Q is β-D-galactosyl or β-D-glycosyl. Preferably, the linking group present in the composite structure is hydrophilic. More preferably, the linking group is selected from the group consisting of 2-(5-carboxyfuryl) and 2-(5-carboxythienyl). Optionally, the support can be a polymeric material selected from the group consisting of polyethylene glycol, polyvinyl alcohol, polyvinylacetate, polymers and copolymers of cellulose, vinylalkyl and -dialkyl azlactone, and copolymers of one of acrylate esters, methacrylate esters, acrylamides, and methacrylamides with one of acrylic acid and methacrylic acid. Preferably, the polymer is water-swellable. Such polymer supported fluorogenic enzyme substrate composite structures are useful as sensors that prevent migrating or diluting of the enzyme cleaved fluorescent product and localize it to a particular location such as, for example, at the bottom of an assay micro-well, at the site of growing microcolony, on the tip of a fiber optic probe, or on a defined location in a flow-through cassette or microfluid channel, so as to remain in registration with an excitation and/or detector assembly and also to provide a higher signal density.

Optionally, the support can be a polymeric or ceramic bead. Such bead supported fluorogenic enzyme substrate composite structures are useful, for example, in flow cytometry based biological detection systems. Beads can be color-coded such that beads of specified colors contain polymer supported fluorogenic enzyme substrates for specific enzymes. Such beads are useful as sensors that localize and partition the enzyme cleaved fluorescent products derived from several different enzymes present in the same solution. Bead colors and fluorescent return signals can be correlated to indicate the relative activity of the enzymes present in a sample.

Where the fluorogenic enzyme substrate of the invention is to be immobilized on a support (i.e. either directly by adsorption or through a linking group) to form a sensing composite structure, supports of various forms can be employed. Where the sensing composite structure is to be used in a flow-through cassette, in a microwell, or as a free standing micro-compartment on a carrier, a planar substrate may be used. Examples of planar substrates, or substrates that can readily be made planar, include free-standing polymers in the form of a membrane or film, and coatable polymers (i.e. polymers that can be coated on a free support). Free-standing membranes may be formed from various polymers including polyethylene, polypropylene, polyvinylidene chloride, polyvinyl chloride (PVC), polysulfone, cellulose, functionalized cellulose, and nylon, and from silica, such as a silica xerogel or porous glass. Useful substrates are preferably permeable to ions and to the enzymes of interest and optionally are functionalized with, or have been treated (e.g. air oxidized) so as to intrinsically carry groups that are complimentary to and react with functionality of the R group. One example of a preformed support is alpha cellulose in the form of a cotton lint paper. A second example of a support is hydrophilic porous polypropylene coated with PVC as described in PCT patent publication WO 92/07899, which is herein incorporated by reference in its entirety. A third example is hexanediamine-functional cellulose as described in U.S. Pat. No. 5,958,782, which is herein incorporated by reference in its entirety.

In some cases it is advantageous to prepare sheets of the preformed support containing the fluorogenic enzyme substrate of this invention and optionally containing dried reagents such as growth nutrients, promoters, and gelling agents useful in optimizing a biological assay. These sheets can be made to have an adhesive backing. By cutting, stamping or otherwise segmenting the sheets, sensor disks of well-defined dimensions or fluid capacity can be prepared and laminated onto the carrier substrate. One preferred embodiment incorporates sensor disks into a plurality of test wells of a traditional microwell tray. A second preferred embodiment incorporates a plurality of sensor disks onto a flexible or rigid planar carrier. Suitable carriers include polyethylene, polypropylene, polyvinyl chloride, acrylonitrile butadiene-styrene, fluoropolymers, polycarbonates, and acrylates. For certain applications involving the differentiation or enumeration of microorganisms, it is preferred that the sensor disks have a surface-to-volume ratio sufficient to retain an effective amount of bound fluorophore and preferably to receive a known volume of a sample solution or suspension useful for the analysis. In general, a thickness of from 0.10 mm to 2.00 mm is suitable. The thickness, in cooperation with the surface area, determines the volume of fluid required to completely wet the sensor disk.

Macromolecular Conjugates

In another embodiment, the fluorogenic compounds of Formula (I) can be chemically bonded to a biomolecule ligand, wherein the compound of Formula (I) is covalently bound to the biomolecule ligand through at least one of $R^2$, $R^3$, or $R^4$ by means of one of a bond and a linking group, such as described above for the composite structure.

Such macromolecular conjugates are useful, for example, in homogeneous drug immunoassays, for drug receptor assays, or for the detection of any biomolecule for which there is a specific binding partner. The biomolecule ligand can be a polypeptide, protein, carbohydrate, glycoprotein, steroid, or any organic molecule for which a specific binding partner exists in biological systems or can be synthesized. The biomolecule ligands in functional terms are selected from the group consisting of antigens and antibodies thereto; haptens and antibodies thereto; and hormones, vitamins, metabolites and pharmacological agents, and their receptors and binding substrates.

In practice, the fluorogenic enzyme substrates (FES) of the invention may be conjugated to a biomolecule identical to the biological target under assay, such as a drug. The FES-labeled biomolecule and the biological target can be mixed into a solution containing an antibody that binds competitively to both the biomolecule and the FES-labeled biomolecule. Once the antibody binds to the FES-labeled biomolecule, the FES becomes protected and cannot be cleaved by added enzyme. However, as the assayed biomolecule concentration increases, the FES label becomes more exposed as more cleaved FES product is generated. The reaction rate is proportional to the concentration of the assayed drug.

Conjugates for haptens of molecular weight between 100 and 1000, or an analog thereof, particularly a drug or drug analog, find application in the detection of anticonvulsants such as diphenylhydantoin, phenobarbital, primidone, carbamazepine, ethosuximide, and sodium valproate, and particularly for detecting aminoglycoside antibiotics such as gentamicin, tobramycin, amikacine, kanamycin, sisomicin, and netilmicin, as well as others. The linking group can be a single bond or a chain containing 1 to 10 carbon atoms and 0 to 5 heteroatoms selected from nitrogen, oxygen and sulfur. Where the binding component has an available primary amino group, the linking group may be carboxyl, forming an amide bond between the FES residue and the binding component.

Additional examples of desirable conjugates include those for hormones such as insulin, chorionic genadotropin, thyroxine, lithyromine, and estriol; antigens and haptens such as ferritin, bradykinin, prostaglandins, and tumor specific antigens; vitamins such as biotin, vitamin $B_{12}$, folic acid, vitamin E, vitamin A, and ascorbic acid; metabolites such as 3',5'-adenosine monophosphate and 3',5'-guanosine monophosphate; pharmacological agents or drugs, particularly those described below; antibodies such as microsomal antibody and antibodies to hepatitis and allergens; and specific binding receptors such as thyroxine binding globulin, avidin, intrinsic factor, and transcobalamin.

The present assay is particularly useful for the detection of haptens (and analogs thereof) of molecular weight between 100 and 1000, particularly drugs and their analogs, including the aminoglycoside antibiotics such as streptomycin, neomycin, gentamicin, tobramycin, amikacin, kanamycin, sisomicin, and netilmicin; anticonvulsants such as diphenylhydantoin, phenobarbital, primidone, carbamazepine, ethosuximide, and sodium valproate; bronchodialators such as theophylline; cardiovascular agents such as quinidine and procainamide; drugs of abuse such as morphine, barbiturates and amphetamines; and tranquilizers such as valium and librium.

The molecular weight of the proteins or polypeptides can be between 130 and 10,000,000, preferably between 1,000 and 1,000,000. Particular polypeptides that can be conjugated according to the present invention include angiotensin I and II, C-peptide, oxytocin, vasopressin, neurophysin, gastrin, secretin, glucagon, bradykinin and relaxin. Proteins that can be conjugated include the classes of protamines, mucoproteins, glycoproteins, globulins, albumins, scleroproteins, phosphoproteins, histones, lipoproteins, chromoproteins, and nucleoproteins. Examples of specific proteins are prealbumin, $a_1$-lipoprotein, human serum albumin, $a_1$-acid glycoprotein, $a_1$-antitrypsin, $a_1$-glycoprotein, transcortin, thyroxine binding globulin, haptoglobin, hemoglobin, myoglobin, ceruloplasmin, $a_2$-lipoprotein, $a_2$-macroglobulin, $\beta$-lipoprotein, erythropoietin, transferin, homopexin, fibrinogen, immunoglobulins such as IgG, IgM, IgA, IgD, and IgE, and their fragments, e.g., $F_c$ and $F_{ab}$, complement factors, prolactin, blood clotting factors such as fibrinogen and thrombin, insulin, melanotropin, somatotropin, thyrotropin, follicle stimulating hormone, leutinizing hormone, gonadotropin, thyroid stimulating hormone, placental lactogen, intrinsic factor, transcobalamin, serum enzymes such as alkaline phosphatase, lactic dehydrogenase, amylase, lipase phosphates, cholinesterase, glutamic oxaloacetic transaminase, glutamic pyruvic transaminase, and uropepsin, endorphins, enkephalins, protamine, tissue antigens, bacterial antigens, and viral antigens such as hepatitis associated antigens (e.g., $HB_1Ag$, $HB_cAg$ and $HB_eAg$).

Methods and Devices for Detecting and Enumerating Microorganisms

Fluorogenic enzyme substrates of the invention can be used to detect the presence of enzyme activity, including enzyme activity associated with specific enzymes in the general enzyme classes glycosidases, esterases, peptidases, and others that support specific hydrolytic cleavage of the bond between the coumarin and the substrate. Enzymes for which fluorogenic enzyme substrates of Formula I may be generated include, without limitation, the following.

| | |
|---|---|
| α-L-arabinosidase | Q = α-L-arabinopyranoside |
| β-cellobiosidase | Q = β-D-cellobioside |
| α-L-fucosidase | Q = α-L-fucopyranoside |
| β-D-fucosidase | Q = β-D-fucopyranoside |
| β-L-fucosidase | Q = β-L-fucopyranoside |
| α-galactosaminidase | Q = N-acetyl-α-D-galactosaminide |
| β-galactosaminidase | Q = N-acetyl-β-D-galactosaminide |
| α-galactosidase | Q = α-D-galactopyranoside |
| β-galactosidase | Q = β-D-galactopyranoside |
| α-glucosaminidase | Q = N-acetyl-α-D-glucosaminide |
| β-glucosaminidase | Q = N-acetyl-β-D-glucosaminide |
| α-glucosidase | Q = α-D-glucopyranoside |
| β-glucosidase | Q = β-D-glucopyranoside |
| β-glucuronidase | Q = β-D-glucuronic acid |
| β-lactosidase | Q = β-D-lactopyranoside |
| α-maltosidase | Q = β-D-maltopyranoside |
| α-mannosidase | Q = α-D-mannopyranoside |
| β-mannosidase | Q = β-D-mannopyranoside |
| β-xylosidase | Q = β-D-xylopyranoside |
| carboxyl esterase | Q = butyrate; caprylate |
| esterase (misc) | Q = nonanoate; palmitate |
| cathepsin | Q = L-arginine amido |
| dipeptidyl aminopeptidase II | Q = L-lysyl-L-alanine amido- |
| γ-glutamyl transpeptidase | Q = γ-L-glutamic acid amido- |
| pyroglutamyl peptidase | Q = L-pyroglutamic acid amido- |
| peptidases (various) | Q = N-acetyl-L-lysine amido-; L-alanine amido-; L-arginyl-L-arginine amido-; L-aspartic acid amido-; N-α-benzyloxycarbonyl-L-arginine amido-; N-benzyloxycarbonyl-glycyl-L-proline amido-; L-citrulline amido-; γ-L-glutamic acid amido-; L-glutaryl-glycyl-arginine amido-; L-glycine amido-; glycyl-glycine amido-; glycyl-L-phenylalanine amido-; glycyl-L-proline amido-; L-histidine amido-; L-hydroxyproline amido-; L-isoleucine amido-; L-leucine amido-; L-lycine amido-; L-methionine amido-; L-ornithine amido-; L-phenylalanine amido-; L-proline amido-; L-pyroglutamic acid amido-; L-serine amido-; L-serine-L-tyrosine amido-; L-tryptophan amido-; L-tyrosine amido-; L-valine amido- |
| urokinase | Q = L-glutaryl-glycyl-arginine amido- |

A panel of one or more fluorogenic enzyme substrates of the present invention may also be used to advantage to detect or identify an unknown microorganism based on a determination of its enzyme activity profile. Many enzymes have been identified which are specific to particular groups of bacteria, and it is likely that other enzymes will be identified in the future that demonstrate such specificity (see generally, *Bergey's Manual of Systematic Bacteriology*, 1989, Williams and Wilkins, U.S.A.). For example, most gram-negative bacteria exhibit L-alanine aminopeptidase activity. Coloform bacteria (a group of gram negative bacteria) additionally express galactosidase activity. *E. coli* bacteria (a species in the Coliform group) additionally express β-D-glucuronidase activity. The enzyme β-D-glucosidase is found in the Enterococcus group of bacteria. The *Candida albicans* yeast pathogen exhibits N-acetyl-β-D-glucosaminidase activity.

Panels of fluorogenic enzyme substrates of Formula I can be used to test for a large number of common microorganisms, including without limitation the following microorganisms: *Aeromonas hydrophilia, Aeromonas caviae, Aeromonas sobria, Bacillus cereus, Bacillus stearothermophilus, Bacillus subtilis, Bacillus sphaericus, Bacteroides fragilis, Bacteroides intermedium, Candida albicans, Citrobacter freundii, Clostridium perfringens, Enterobacter aerogenes, Enterobacter cloacae, Enterococcus faecium, Enterococcus faecalis, Escherichia coli, Haemophilus influenzae, Haemophilus parainfluenzae, Klebsiellapneumoniae, Lactococcus lactis, Mycobacterium fortuitum, Neisseria gonorrhoeae, Organella morganii, Peptostreptococcus anaerobius, Peptococcus magnus, Proteus mirabilis, Pseudomonas aeruginosa, Pseudomonas fluorescens, Pseudomonas pudita, Salmonella typhimurium, Serratia liquefaciens, Serratia marcescens, Staphylococcus aureus, Staphylococcus epidermidis, Staphylococcus hominis, Staphylococcus simulans, Streptococcus agalactiae* B, *Streptococcus anginosus, Streptococcus constellatus, Streptococcus faecalis* D, *Streptococcus mutans, Streptococcus pyogenes, Streptococcus uberis*, and *Xanthomonas maltophilia*.

Fluorogenic enzyme substrates of the present invention can provide for the rapid identification of microorganisms or enzymes isolated from clinical samples, food samples, cosmetics, beverage samples, water and soil samples. Clinical samples may include urine, stools, wound, throat, genital samples, or normally sterile body fluids such as blood or cerebral spinal fluid. The microorganisms are usually isolated from the specimen prior to identification. In antibiotic susceptibility and minimum inhibitory concentration testing, an absence of enzyme activity in the presence of antibiotics, as compared to the presence of enzyme activity of a control sample, is indicative of antibiotic effectiveness. The compositions, articles and systems are useful to screen for disease states (e.g. excessive alkaline phosphatase in seminal fluid is indicative of prostate cancer; also, the activity of urinary N-acetyl-β-D-glucosaminidase provides a sensitive measure of renal health). They are also useful for identification of an organism in a specimen. In most cases, the organisms being determined will be bacteria. However, other microorganisms such as fungi, can also be identified.

A test card, microwell array, capillary array, microfluidic device, sensor disk array, or other apparatus is provided having a plurality of wells, compartments, or isolated supports which separately contain specific, unique fluorogenic enzyme substrates according to Formula (I) for each of the enzyme tests together with other reagents for the tests. A support containing multiple sensor disks of the present invention is particularly useful for this application. In use, a sub-sample of the bacterial suspension is added to each compartment and a detectable product is typically developed after a relatively short incubation period of 2–30 minutes. The amount of the corresponding enzyme in each sub-sample is then determined by spectrophotometric analysis.

The number of fluorogenic enzyme substrates required to identify a particular microorganism will depend on the microorganism. In some cases, a single compartment may be enough. In other cases, multiple compartments, each containing a specific fluorogenic enzyme substrate or concentration of the substrate will be required to differentiate one microorganism from another having a very similar profile. Example profiles are outlined in U.S Pat. No. 4,591,554 and U.S. Pat. No. 5,236,827, incorporated herein by reference in their entirety.

The degree of reaction of an enzyme with each of the substrates may be determined by examination of each reaction compartment with a fluorescence detection system. In specific implementations an initial fluorescence reading is taken as soon after inoculation as convenient. Subsequent readings are taken at periodic intervals and used to calculate rates of reaction or to determine the onset of detection for each reaction compartment. This information is transmitted to a processor assembly, which compares the data to a set of standard rate data for microorganisms and determines an identification.

In one preferred embodiment, a compact solid-state fluorescence detection system is used, comprising a GaN or SiC LED source, a compact Photomultiplier Tube (PMT) or photodiode detector, and excitation and emission filters selected for the particular fluorophors of the present invention. The compact, solid state scanner format is enabled by the use of the red-shifted fluorogenic enzyme substrates of the present inventions. Such compact, portable formats make possible detection systems for use in a variety of settings other than a central laboratory, such as in a doctor's office, a food processing plant, or in the field.

Alternatively, a presence/absence test can be performed in each of several compartments of a test card, microwell array, capillary array, microfluidic device, sensor disk array, or other apparatus. These tests can be suitable for applications that inoculate specific compartments with pre-determined doses of a bacterial culture to perform a most probable number analysis. In these implementations, incubation times often range from 30 minutes to 72 hrs. World Patent Application 96/40980 and World Patent Application 99/06589 are hereby incorporated by reference in their entirety.

In one preferred embodiment, a carrier or microwell tray is provided having a plurality of sensor disks with immobilized assay reagents, optional growth nutrients and fluorogenic enzyme substrates specific to the microorganism of interest. The carrier or microwell tray may comprise a plurality of sets of sensor disks, each set having a uniform volume and the sets varying in volume. Each sensor disk takes up a defined volume of liquid. Preferably the sensor disks take up from about 0.01 to about 25 microliters of liquid. During use a specimen to be analyzed is diluted in an appropriate growth medium or buffer solution and applied to sensor disks or microwells. The sensor disks or microwells are then covered to prevent evaporation, and the microorganisms contained therein are allowed to incubate at elevated temperature until at least one cell division process is completed. Viable organisms in a given sensor disk give rise to enzymatic cleavage of the fluorogenic enzyme substrate of this invention. An initial fluorescence reading is taken as soon after inoculation as convenient. Subsequent readings are taken at periodic intervals and used to determine the onset of detection for each compartment. This information is transmitted to a processor assembly that uses a statistical formula, based on the number of positive and negative results for each set of sensor disks, to estimate the number of organisms present in the initial sample.

Fluorogenic enzyme substrates of the present invention, and composite structures derived therefrom can also be mixed with hydratable gelling agents and growth media and coated uniformly into a Petri dish or microwell. In these methods, a specimen to be analyzed is diluted in an appropriate growth medium or buffer solution and applied evenly to the gel coating containing the fluorogenic enzyme indicator. The inoculated gel coating is then covered to prevent evaporation, and the microorganisms contained therein are allowed to incubate at elevated temperatures until at least one cell division process is completed. Growing microcolonies cause enzymatic cleavage of the fluorogenic enzyme substrate of this invention, creating fluorescent spots in the coating. In one embodiment, the fluorescent spots are detected using a fluorescence detection system comprising a compact blue LED light source. This information is transmitted to a processor assembly that comprises image processing software that optionally counts the spots to generate a microbial count, and optionally correlates this count with the sample number.

Methods and Devices for Detecting Intracellular Reporters

Fluorogenic enzyme substrates of the present invention can also be used to detect enzyme markers and reporters in cells. Glycosidases are important reporter gene markers. Specifically, lacZ, which encodes β-galactosidase, is extensively used as a reporter gene in animals and yeast, whereas the β-glucuronidase (GUS) gene is a popular reporter gene in plants. Phosphatases serve as enzyme markers, allowing researchers to identify primordial germ cells, to distinguish sub-populations of bone marrow stromal cells and to investigate in vitro differentiation in carcinoma cell lines. P ALP-1, the gene for human placental alkaline phosphatase, has been used as a eukaryotic reporter gene, and is particularly effective for lineage studies in murine retina. The P ALP-1 gene has also been engineered to produce a secreted alkaline phosphatase, allowing quantitation of gene expression without disrupting the cells. In one preferred embodiment, fluorescent signals produced by the action of enzymes such as those described above may be detected using a fluorescence detection assembly comprising a compact blue LED light source.

Fluorogenic enzyme substrates of Formula (I) can be used to detect, count or sort cells by epifluorescence microscopy or flow cytometry based on the presence of specific enzyme markers. The compounds of Formula (I) possess the distinct advantage of not requiring excitation illumination in wavelength ranges of 200–400 nm that damage genetic material and cells. In addition, the bulky Ar ion lasers typically used for flow cytometric analysis can be replaced by compact GaN, SiC or ZnSe LED or laser diode sources.

In the case of detecting cells by flow cytometry, cells are treated with fluorescent enzyme substrates in an aqueous suspension and are then passed across a sample detector under conditions wherein only about one individual cell is present in a sample detection zone at a time. A light source, preferably a solid state GaN, SiC or ZnSe laser or light emitting diode configured to excite the fluorogenic hydrolysis products, illuminates each cell. A detector, typically a photomultiplier or photodiode, detects emitted radiation from the treated cells. For cell sorting applications, the detector controls gating of the cell in the detection zone into one of a plurality of sample collection regions on the basis of the signal(s) detected. General descriptions of such cell sorting apparatus are provided in U.S. Pat. Nos. 4,172,227; 4,347,935; 4,661,913; 4,667,830; 5,093,234; 5094,940; and 5,144,224, incorporated herein by reference in their entirety.

Methods and Devices for Evaluating Sterilization Efficacy

Another use for the present invention is to evaluate sterilization efficacy. Sterilization cycles are effective against a wide range of microorganisms, but are not infallible. Sterilization cycles may include ethylene oxide, steam, dry heat, radiation, propylene oxide, methyl bromide, ozone, chlorine dioxide, formaldehyde, and other gaseous and liquid agents. Sterilization may also include hydrogen peroxide and peracetic acid. It may occur in the gaseous, liquid, and plasma phases.

It is important to be able to test the effectiveness of a sterilization cycle. One way of doing so is to use a sample of resistant enzymes or resistant spores that produce enzymes. In accordance with a method of the invention, a sample is placed into the structure undergoing sterilization, and is exposed to the sterilization cycle. After completion of the cycle, the sample bearing the resistant enzymes or spores is tested for any remaining viable enzymes. If the sterilization cycle was effective, there should be no viable enzyme activity remaining.

The enzymes or spores can be tested for viability by exposing them to a compound of Formula (I), since any remaining viable enzyme activity will cleave the molecule, producing a cleaved fluorescent product, which is then easily detected. Optionally, the enzyme sample can undergo an incubation period after sterilization and before testing, in order to amplify remaining viable enzyme activity.

Microorganisms suitable for monitoring sterilization conditions according to the present invention include *Bacillus stearothermophilus* and *Bacillus subtilus*. *Bacillus stearothermophilus* is particularly useful to monitor sterilization under steam sterilization conditions. *Bacillus subtilis* is particularly useful to monitor conditions of gas and dry heat sterilization. Preferred enzymes for monitoring sterilization conditions using the fluorogenic enzyme substrates derive from spores of *Bacillus stearothermophilus* and *Bacillus subtilis*. Useful enzymes from *Bacillus stearothermophilus* include (α-D-glucosidase, β-D-glucosidase, alkaline phosphatase, acid phosphatase, butyrate esterase, caprylate esterase lipase, leucine aminopeptidase, chymotrypsin phosphohydrolase, α-D-galactosidase, β-D-galactosidase, alamine aminopeptidase, tyrosine aminopeptidase, and phenylalanine aminopeptidase. Useful enzymes from *Bacillus subtilis* include α-L-arabinofuranoside, N-acetyl-β-glucosaminidase, β-D-cellobiosidase, β-D-glucosidase, leucine aminopeptidase, alanine aminopeptidase, tyrosine aminopeptidase, phenylalanine aminopeptidase, and proline aminopeptidase.

The fluorogenic enzyme substrate and the resistant spore or enzyme can be co-located in a sensing element designed to expose the biological, and/or the indicator separately to the sterilization cycle and then to provide a means to bring them into intimate contact only after sterilization is complete. One particularly useful sensing element configuration is disclosed in U.S. Pat. No. 5,418,167, incorporated herein by reference. This sensing element comprises a compressible outer plastic vial containing resistant spores or enzyme and a breakable inner glass vial containing a solution of a suitable substrate. After completion of the sterilization cycle, the top of the outer vial is sealed, the vials are compressed to break the inner glass vial, releasing the substrate to mix with the resistant spores or enzyme. Efficacy of the sterilization procedure is determined by performing a fluorescent analysis of the enzyme substrate in the vial after mixing. Fluorogenic enzyme substrates of the present invention are particularly useful in this type of application because they are chemically stable tinder the harsh conditions present in commercial sterilization processes, yet are still susceptible to enzymatic hydrolysis.

Another method and apparatus of the invention involves printing or coating in a discontinuous pattern (e.g., indicia or barcode) onto a test strip, where the printed material contains a resistant enzyme or spore. The enzyme may be covalently attached or otherwise bound to the printed material and does not bleed or migrate in the presence of buffer solutions. In use, this strip is exposed to the conditions of sterilization, after which it is dipped into a buffer solution containing an FES of the present invention. Efficacy of the sterilization procedure is determined by performing a fluorescent analysis of the printed or coated pattern. If enzyme activity is present, the pattern becomes detectable using a scanner configured to detect fluorescence of the FES hydrolysis product. This enzyme based method can be used in conjunction with a chemical indicator that turns black under the conditions of sterilization. In this case, successful sterilization is positively indicated by the growth of the chemical indicator pattern and the absence of an FES fluorescence pattern. Other useful discontinuous coated patterns on a substrate can include, for example, an alphanumeric string, a design, and a machine-readable pattern.

The printed enzyme or spore carrier is typically capable of being hydrated and is capable of retaining the enzyme through covalent attachment or physical adsorption, without adversely affecting enzyme activity. Photocrosslinkable azlactone hydrogel materials are preferred carriers for this application. Azlactone functional groups on these polymers are reactive with amine or thiol residues on proteins and enzymes through a simple addition reaction. Enzyme functionalized polymers and films retain a high enzyme activity. These gels also contain photo-crosslinkable side chains and can be photo-lithographically patterned onto substrates without loss of enzyme activity. Also, they can be patterned onto substrates using the method of laser induced thermal imaging (LITI) without loss of enzyme activity. U.S. patent application Ser. No. 09/183,197, filed Oct. 30, 1998, teaches how to prepare and utilize these materials and is herein incorporated by reference.

The cleaved fluorescent indicator molecules require incident light to cause fluorescence. Traditionally, bulky lamps are needed to provide incident light of an appropriate wavelength to cause fluorescence. However, molecules according to Formula (I) fluoresce when irradiated with GaN-, SiC-, or ZnSe-based LEDs that emit light of approximately 450–470 nm.

Capturing Biologically Active Molecules

Another use for compounds of Formula (I) is in capturing, or selectively binding, desired biologically active molecules. Typically, this is done by applying a biologically receptive gel to a polymeric support. Preferably, the gel is such that it permits bound molecules to undergo electrophoresis. Once the bound molecules are separated, a fluorescent indicator such as that described by Formula (I) can be used to show their presence.

Methods and Devices for Detecting Enzyme-Conjugated Secondary Detection Reagents Fluorogenic enzyme substrates of the present invention can also be used to detect enzyme-conjugated secondary detection reagents. Conjugates of glycosidases and conjugates of phophatases are widely used as secondary detection reagents in enzyme-linked immunosorbent assays (ELISAs); inumunohistochemical techniques; and Northern, Southern, and Western blot analysis. In one preferred embodiment, the fluorescent signals are detected using a fluorescence detection assembly comprising a compact blue LED light source. Fluorescent enzyme substrates may be used as indicators in ELISA assays, where the enzyme is attached to an antibody or DNA reporter probe used in a sandwich assay. After forming the sandwich and rinsing off unbound reporter, the fluorescent indicator is introduced. The enzyme serves as an amplifier by cleaving as many as one million dye molecules.

Instrumentation Overview

In interrogating a cleaved product, fiber-optic bundles can be used to direct light from an LED to multiple samples or simultaneously to a sample and a reference channel. Alternatively, fiber optic routing bundles can be used to direct emission light from multiple samples to one detector. In the event that an expensive detector is used, a multiplexed emissions format can offer cost advantages. Each sample can be sequentially addressed with its own LED so that the detector only receives a signal from one sample at a time. Both the excitation and emission routing can be used together, and the output from the sample and reference channels can be digitized then normalized to correct for instrument and temperature variations.

In specific implementations of the invention the LEDs and photodiodes are housed in a single block, while the filters and focusing lenses are housed in an optics block. These two blocks are mated together, then mated to an optical routing block that consists of bifurcated fiber bundles. Bifurcated fiber bundles enable multiplex detection architectures and referencing schemes. These can be extended to any number of samples, each individually addressable with GaN, InGaN, ZnSe, or SiC LED or laser diode sources.

In a related format, light sources and detectors can be mounted directly to the individual samples, without the need for a routing block. Alternatively, fiber routing can be employed for only the excitation, or only the emission channels. Whether using a lamp source or LED sources, a digitized and normalized output from each channel can be monitored as a function of time to track the onset of an emission change associated with the biological indicator.

Compounds of Formula (I) can be used in a variety of applications where the detection of enzyme activity is important or advantageous. In particular, these compounds are useful for detecting endogenous enzyme activity in biological systems or as reporters for enzyme-linked diagnostic assays. While prior art lamp based fluorescence detection systems have proven commercial utility, solid state LED and laser diode sources are preferred. These solid state sources generally increase reliability, reduce cost and size, and improve noise/drift characteristics of the opto-electronics system. GaN blue LED's introduced by Nichia Chemical Industries of Japan have enabled the development of a practical LED-based opto-electronics system for polyaromatic hydrocarbon based fluorescence indicator systems. World Patent Application WO 98/37802 is hereby incorporated by reference. In particular, the GaN LED emission (maximum at 450–470 nm) can be mated to the absorbence maxima of the fluorogenic enzyme substrates of Formula (I). This attribute enables the design of compact, portable detection devices for a variety of assays that involve the interrogation of enzyme activity.

FIG. 1a is a block diagram illustrating a representative optical and electronic sensing system 310 for performing a biological analysis of the present invention. A sensing system of the present invention minimally comprises sensing element 320 and excitation assembly 330 for performing a biological analysis. This configuration enables visual detection of enzyme activity using, for example, a battery powered GaN LED pointer as the excitation assembly and using, for example, an assay vial or test strip containing a fluorogenic enzyme substrate as the sensing element. The system optionally comprises detection assembly 340 and processor assembly 350 for performing automated analysis and for storing, retrieving, and transmitting data electronically. The excitation, detection and processor assemblies may be adapted to interrogate one sensor element or an array or combination of sensor elements as required to perform the biological analysis of interest.

Sensing elements 320 of the present invention may comprise one or more fluorogenic enzyme substrates 322 of the present invention and fluid handling architecture 324 structured and adapted to support mixing or otherwise intimate interaction of one or more biological samples with at least one of the fluorogenic enzyme substrates of the sensing element. The fluid handling architecture of the sensing element may comprise a cuvette, capillary, absorbent test strip, one or more microlocations, one or more microwells, an absorbent sensor disk, hydratable gel pad, optode, or microfluidic chip that comprises an FES of the present invention.

Multiple sensing elements 320 may be combined or arranged into arrays, depending on the nature of the analysis, without deviating from the scope or spirit of the invention. For example, an array of sensor disks of the present invention, each with the capacity to absorb a certain volume of sample fluid, can be used to perform a microbial most probable number analysis. Alternatively, an array of sample wells or sensor disks can be used to perform an enzyme rate-of-reaction profile analysis for an unknown microorganism.

A single sensing element 320 may give rise to an array of distinct and measurable signals. For example, the sensing element made by impregnating a Petri dish gel with an FES of the present invention, when inoculated with a dilute sample containing microbial contaminates, will give rise to a number of distinct fluorescent spots at the sites of growing colonies.

A sensing element 320 may be configured in such a way as to require external forces to enable mixing of the FES and the sample. For example, a sterilization indicating sensing element may be made of a compressible outer plastic vial containing resistant spores or enzyme, and a breakable inner glass vial containing a solution of the FES of the present invention. After completion of the sterilization cycle, the top of the outer vial is sealed, the vials are compressed to break the inner glass vial, releasing the FES to mix with the resistant spores or enzyme.

A microfluidic chip or a capillary channel may require external forces (e.g. electrical, centrifugal, pressure) to enable mixing or flow of sample and/or FES. LED optics can also be used to detect enzymatic cleavage of, for example, TUGlc, when an enzyme-containing sample is mixed with an FES on a microfluidic chip via electro-osmotic pumping or mechanical pumping. Solutions of enzyme-containing sample and FES can be placed in two reservoirs connected by microfluidic channels. When the fluids in the channels are driven together, a fluorescent signal can be generated by the enzyme cleavage reaction. This can be used as a means to measure sterilization. It may also be possible to mix the samples using an active microelectromechanical (MEMS) element imbedded in the chip and activated by a radio frequency signal. This embodiment is described in a copending U.S. patent application, U.S. Ser. No. 09/099562, filed Jun. 18, 1998, incorporated herein by reference in its entirety.

Figure 1B:
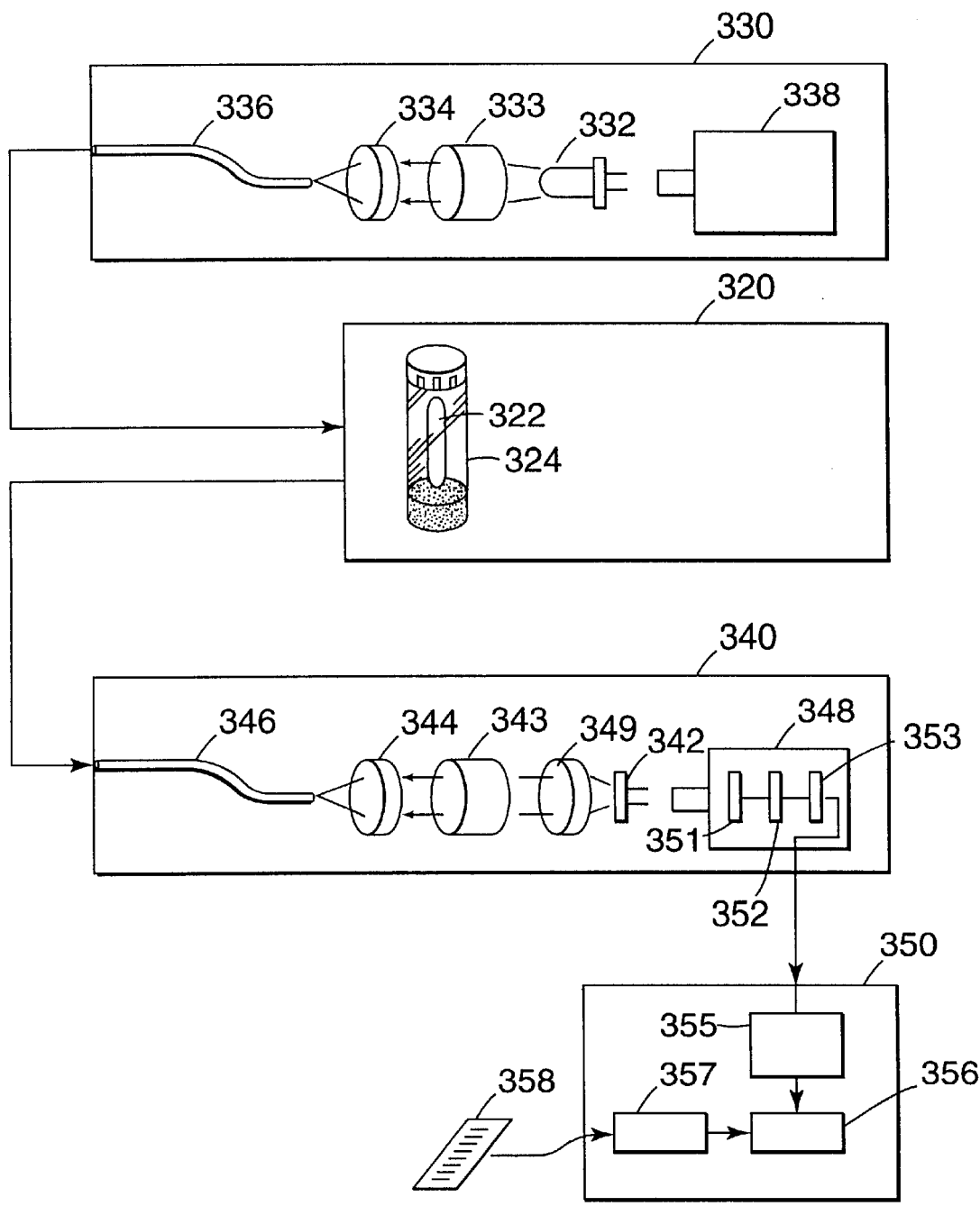
FIG. 1b shows an expanded view of subassemblies of the representative sensing system of the invention.

FIG. 1*b* provides a more detailed view of the subassemblies of sensing system 310 according to one implementation of the invention. The enzymatically cleaved FESs of sensing element 320 have an excitation band centered at $\lambda_1$ and an emission band centered at $\lambda_2$. For this new class of FESs, $\lambda_1$ is at least about 380 nm, more preferably at least about 425 nm, and most preferably at least about 450 nm. Emission wavelength $\lambda_2$ is at least 10 nm greater than $\lambda_1$ and is preferably less than 700 nm. Excitation assembly 330 provides light to the sensing element at the desired band of excitation wavelengths. Excitation assembly 330 is comprised of light source 332, excitation optical filter 333, focusing optics 334, optional light guiding elements 336, and control electronics 338 to drive the light source.

Light source 332 may be a visible laser diode, visible light emitting diode (LED), an incandescent filament, or any other suitable source. Excitation optical filter 333 should have high transmissibility in the excitation wavelength range and low transmissibility in undesirable wavelength ranges. Undesirable transmission wavelengths include the range 200–380 nm which might produce detectable sample autofluorescence, the range within about 25–100 nm of the desired excitation wavelengths which are potential sources of background noise from scattered excitation light, or those which overlap with desired emission wavelengths centered at $\lambda_2$. Focussing optics 334 may be interposed to increase the light intensity at sensor element 320 or to focus the light into light guiding element 336, which in turn transmits light to sensor element 320. Light guiding element 336 may be a single optical fiber, a fiber bundle, a segment of a bifurcated fiber bundle, a large diameter light pipe, a planar waveguide, attenuated total reflectance crystal, dichroic mirror, plane mirror or other light guiding apparatus. Light guiding element 336 and/or focusing optics 334 may serve as common elements of both excitation assembly 330 and detection assembly 340, serving to direct excitation light to the sensor element and to collect return fluorescence from illuminated sensor element 320.

Excitation assembly 330 may be configured to illuminate multiple sensing elements in a sensor array. For example, the excitation assembly may be configured to include an array of light sources, excitation optical filters, focusing optics, and optional light guiding elements configured to provide multiple excitation signals specific to each FES in a sensor array. In this way, arrays containing multiple FES's having specific excitation wavelength bands can be illuminated at their excitation frequencies serially or in parallel. Also, filtered and focused excitation light from a light source can be launched into the proximal end of a bifurcated light guiding element having multiple distal ends positioned such that light is directed to two or more sensing elements in the array.

Control electronics block 338 drives the light source(s) and coordinates the timing of the excitation signals as desired in the periodic measurement of fluorescent signals in a enzyme kinetics profiling experiment, or in the rastor scanning of a sensing element array. Control electronics block 338 can optionally provide timing signals to detection assembly 340 and to mechanical motors, shutters, filter wheels, etc. (not shown) that may be required to perform the analysis. Illumination may be continuous, or amplitude modulated (e.g. pulsed, sine-wave modulated, or combinations thereof). Flash lamps can be pulsed to increase the signal to noise ratio vs. continuous operation. However, these lamps are bulky, require high voltages for operation, require large heat sinks, and introduce shot-to-shot noise variations. Unlike conventional lamps, GaN, InGaN, SiC, or ZnSe LEDs and laser diodes can be sine-wave modulated or pulsed and used in conjunction with the red-shifted FESs of the present invention to offer advantages for multiplexing and signal-to-noise discrimination. Diode laser and light emitting diode intensity can be modulated directly through modulation of the drive current. This can be accomplished with a waveform generator incorporated as part of control electronics block 338. This allows modulation of the light for time-gated or phase-sensitive detection techniques.

Detection assembly 340 serves to collect and detect light from sensing element 320 at the desired fluorescent emission wavelength range centered around $\lambda_2$, wherein $\lambda_2$ is at least 10 nm greater than the center of excitation wavelength range, $\lambda_1$. Detection assembly 340 includes detector 342, emission optical filter 343, collection optics 344, optional light guiding elements 346, optional focusing lens 349, and detection electronics 348, which provide an output electrical signal to processor assembly 350. Collection optics 344 collect induced fluorescent return signals from sensor element 320 or collect these return signals from light guiding element 346, which in turn collects them from sensor element 320. The collection optics may comprise a lens, graded index (GRIN) lens, a collimating lens, mirror or other optical element(s) needed to optimize the collection of return fluorescent light from the sensing element or light guiding element. Light guiding element 346 may be a single optical fiber, a fiber bundle, a segment of a bifurcated fiber bundle, a large diameter light pipe, a planar waveguide, attenuated total reflectance crystal, dichroic mirror, plane mirror or other light guiding apparatus. Collimating lenses, focusing lenses, and/or mirrors can be interposed in the excitation or emission optical trains to enhance the optical throughput or collection efficiencies. In some cases, the excitation and emission optical trains may share common elements as discussed above. The fluorescent return signals are then passed though emission optical filter 343. This filter should have high transmissibility in the emission wavelength range centered around wavelength $\lambda_2$ and low transmissibility in undesirable wavelength ranges. Undesirable wavelengths include the range 200–400 nm where sample auto-fluorescence can occur or wavelengths that overlap the excitation wavelength band centered at $\lambda_1$ where background signals from scattered excitation light can interfere. The filtered fluorescent return signal is then focused onto the active elements of detector 342. Detector 342 converts optical signals into electrical signals, which are transmitted to detection electronics 348. Detector 342 may be a photomultiplier tube, avalanche photodiode, charge coupled device (CCD), photodiodes or other active device. Detection electronics block 348 may include amplifiers 351, band bass filters 352, time gating electronics, frequency gating electronics, mixers, integrating circuits, analog to digital converters 353, or other elements that enhance the electrical signals before transmission to processor assembly 350. The output of detector assembly 340 may be a digital signal that is transmitted to processor assembly 350.

Detection assembly 340 may be configured to receive light signals from multiple sensing elements in a sensor array. For example, the excitation assembly may be configured to include an array of detectors, emission optical filters, collection optics, focusing optics, and optional light guiding elements configured to receive multiple emission signals specific to each FES in sensor array 320. In this way, arrays containing multiple FES's having specific emission wavelength bands can be detected at their emission wavelengths serially or in parallel. Also, filtered and focused emission light from more than one sensing element can be received from the proximal end of bifurcated light guiding element 346 having multiple distal ends positioned such that light is received from two or more sensing elements in the array. Signals from these multiple sensing elements can be discriminated by serially time-gating the excitation and detection or frequency-gating the excitation and detection.

Detection can employ time-gated and/or frequency-gated light collection for rejection of residual background noise. Time-gated detection can be produced either by specified periodic mechanical blocking by a mechanical chopper or switch, or through electronic means. Frequency-gated detection can be produced through electronic means in detection electronics 348 and by digital signal processing techniques in processor assembly 350. Since the FESs of the present invention resist photobleaching, very weak fluorescent emissions can be collected and integrated over very long detection times (continuous illumination or multiple pulsed illumination) to increase sensitivity of detection. Such time integration can optionally be performed electronically in detection electronics 348 or in processor assembly 350 or by chemical integration methods (e.g. photographic film).

Processor assembly 350 is positioned and adapted to process and analyze the emitted signal(s) to determine the concentration, location, or enumeration of biomolecules, bio-macromolecules, or micro-organisms in sensing element 320. This processor may be part of a stand alone unit or may be part of a central computer or local area network. The processor may have software to further refine the signals received from the detection assembly. For example, digital signal processing software 355 may be used to box-car average multiple signals, time-gate the collection and averaging of pulsed return signals, digitally filter white noise from a frequency modulated return signal, or discriminate or differentiate multiple return signals based on carrier frequency, detection sequence, or other factors. The processor assembly may have associated with it relational database 356 which correlates the processed data for each sensing element with corresponding identifiers for the sensing element or sample being tested. The processor assembly may have associated with it alternate means to provide identification codes, such as bar-code scanner 357 to read bar-codes 358 that are attached to the sample container or the sensing element.

Figure 1C:
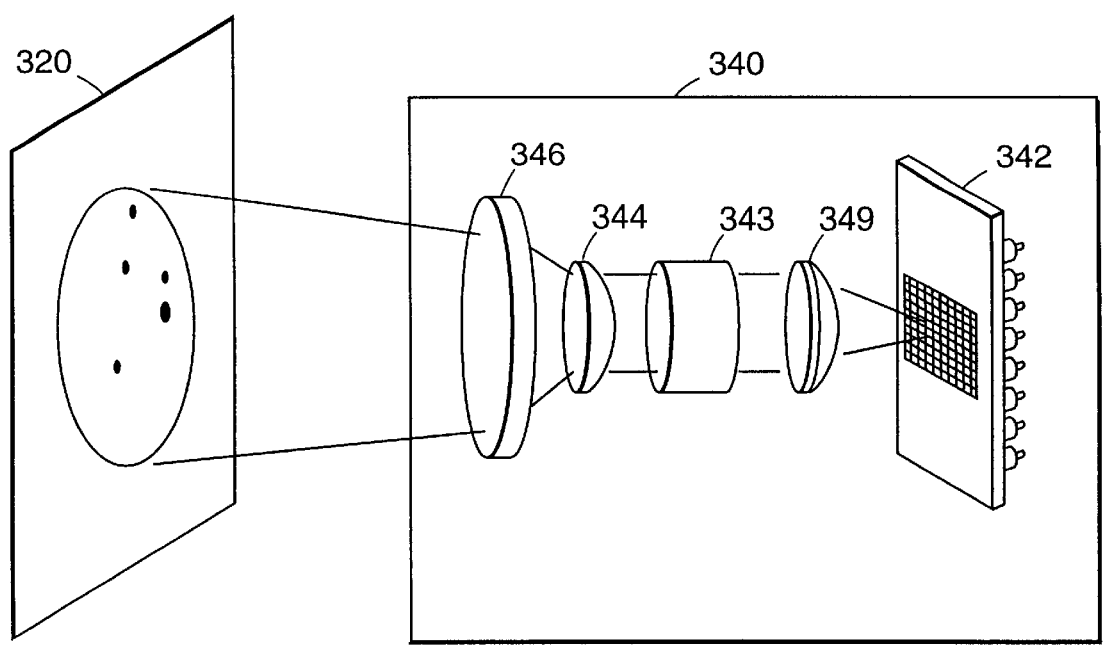
FIG. 1c shows an expanded view of a detection assembly for a representative sensing system of the invention that employs a charge-coupled device (CCD) detector for imaging the sensing element(s).

In one preferred embodiment, the detection assembly comprises a charge coupled device (CCD) as the detector for analyzing a two dimensional FES based sensing element or sensing element array deposited on a planar support. FIG. 1c illustrates one such embodiment of detection assembly 340. The CCD has a number of individually addressable photosensitive detector elements which enable the collection of fluorescent data from the sensor or sensor array on a pixel by pixel basis. This array can be used in combination with an illumination source and proper collection optics to obtain an image of, for example, sites of growing microbial colonies on an inoculated Petrifilm™ having an FES of the present invention. The resulting electronic image can be transmitted to the processor assembly, where image analysis software can be used to enhance the contrast of the image and to count the number of fluorescent spots automatically.

Figure 2A:
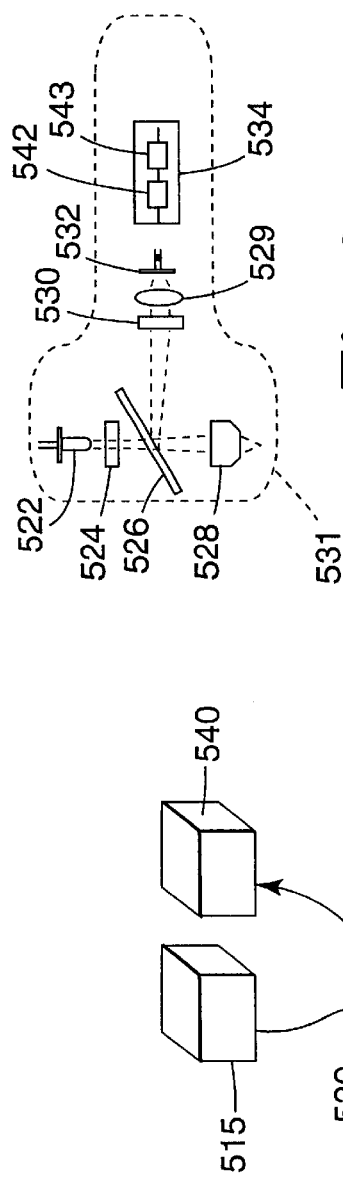
FIG. 2 is a perspective view illustrating a representative sensing system of the invention that employs a detection block for raster scanning of sensing elements.
Figure 2:
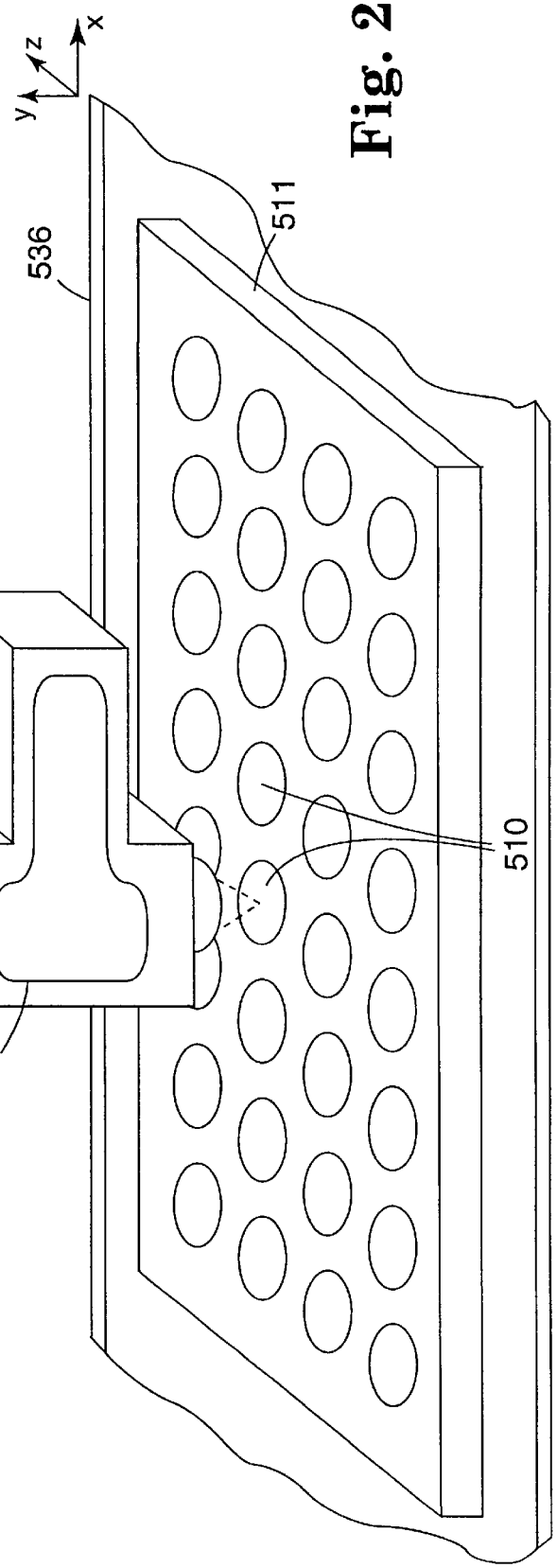

In another preferred embodiment a dichroic beam splitter serves as a common light-guiding element for both excitation and emission signals. Furthermore, a single focussing lens transmits excitation light to the sensor and collects fluorescent light from the sensor. For example, referring to FIG. 2, epifluorescence detection block 520 is provided comprising light source 522, excitation filter 524, dichroic beam splitter 526, focusing lens 528, emission filter 530, and detector 532. Control electronics 515 drive the light source. In one preferred embodiment, the epifluorescence detection block is mounted on X-Y-Z translation mount such that it can be repeatedly and reproducibly positioned in turn over each of several sensing elements or micro-locations 510 of array 511 (e.g., an enzyme kinetics profiling array).

Alternatively, detection block 520 can be made to remain stationary while the sensing elements are repositioned by means of X-Y-Z translation stage 536. Epifluorescence detection block 520 serves to provide light to the sensing elements at the desired excitation wavelengths, to detect light from the sensing elements at the desired emission wavelengths, and to convert detected light signals into electrical signals. These electrical signals are transmitted to detection electronics block 534 and then to processor assembly 540. In one preferred embodiment, detection electronics block 534 and epifluorescence detection block 520 are both compact and can be co-located. For example, light source 522 may be a GaN LED such as part no. NLPB-500 from Nichia Chemical Industries, Anan, Japan. Detector 532 may be a photodiode such at part no. S1133-14 from Hamamatsu Corporation, Bridgewater, N.J., or a compact solid state Photomultiplier tube such as PMT Model H5783, also available from Hamamatsu Corporation. The photodiode may be electrically connected to analog-to-digital converter 543. A suitable single chip analog-to-digital converter is available as catalog no. DDC101 from Burr-Brown Corp., Tucson, Ariz. Signal amplifier 542 (such as catalog no. AD795 from Analog Devices Inc., Norwood, Mass.) may be interposed in the electrical lead between the photodiode and the converter. Digital signals from the converter can be transmitted to processor assembly 540 for further analysis. This type of rastor scanning apparatus finds many applications in the imaging of electrophoresis gels, Northern blots, Southern Blots and Western blots, and in the imaging of microarrays, fluid channels or reaction compartments on a chip.

Preferably the FESs at each microlocation on the sensing element or array differ only in the choice of the substituent Q in Formula (I), such that upon enzymatic cleavage, each FES has the same characteristic absorption and emission spectrum. In this case, the epifluorescence detection block can be used to rastor scan any and all microlocations on the substrate and provide data to the processor assembly on a pixel-by-pixel basis for further analysis. In some situations it is desirable to use different detector gains at different microlocations, for example when collecting data for enzyme kinetic profile analysis.

Figure 3:
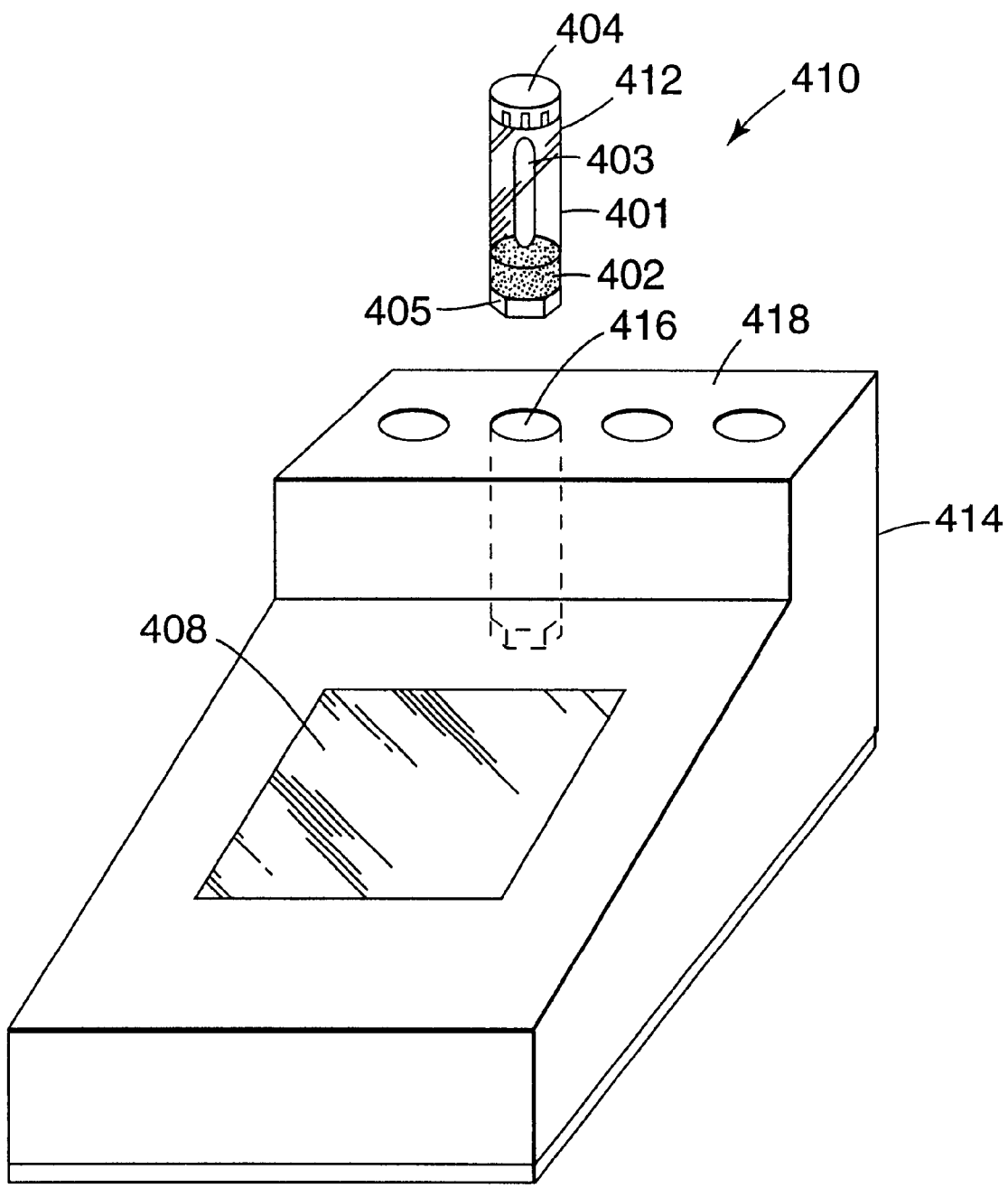
FIG. 3 is a perspective view of a sterilization monitoring apparatus of the invention, showing an example of how a sensing element and the measuring device can be oriented with respect to each other before being coupled together.
Figure 4:
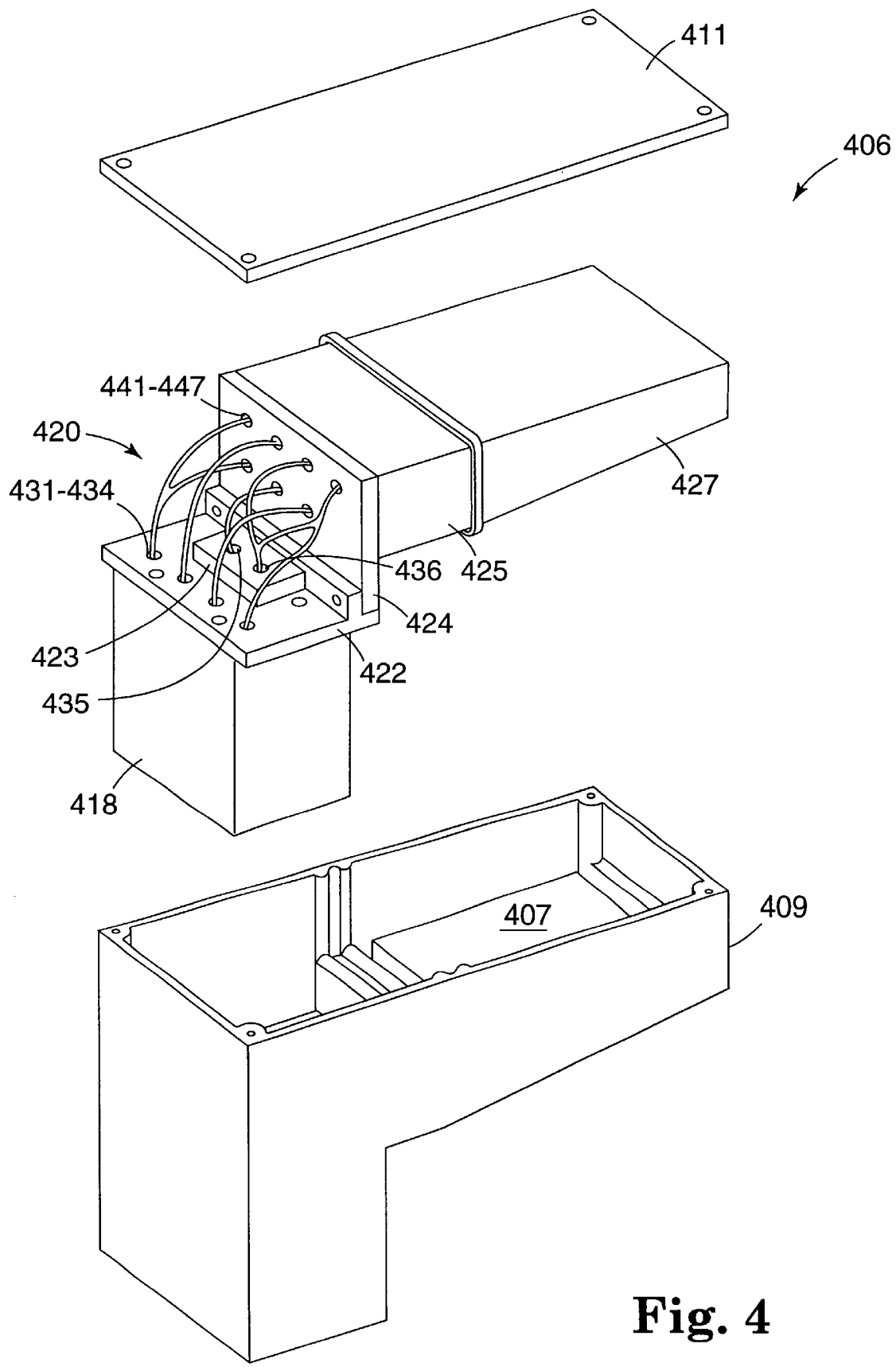
FIG. 4 is an exploded perspective view of the measuring device of FIG. 3, viewed from the bottom.
Figure 5:
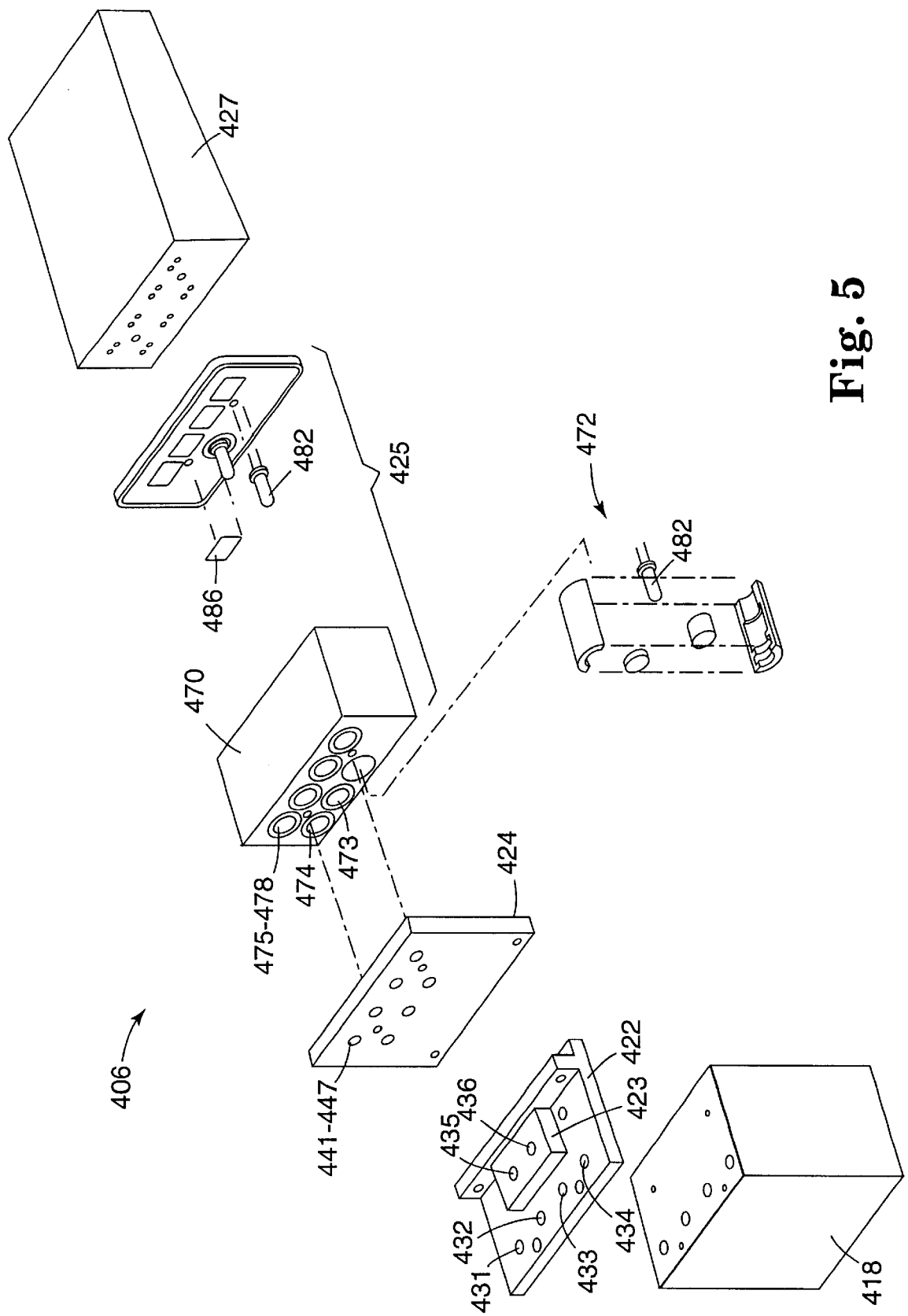
FIG. 5 is an enlarged, exploded perspective view of the measuring device of FIG. 3, except that the housing, base, and processor assembly are removed.

FIGS. 3, 4 and 5 provide perspective views showing the optical train of a particular embodiment of apparatus for carrying out the present invention on multiple sensor elements. This embodiment uses a multiplexed optical train comprising multiple LED light sources, bifurcated fiber-optic cables, and multiple detectors. Sensing system 410 includes measuring device 414 and a plurality of sensing elements 412 for measuring enzyme activity. In a preferred embodiment, each sensing element 412 is a sterilization indicator vial having compressible outer plastic shell 401 that is optically transparent or translucent in the range of 390 –700 nm. Resistant spores or enzyme are adsorbed on non-woven sensor disk 402 at the bottom of the tube. Breakable inner glass vial 403 is situated above the sensor disk and contains a solution of the FES of the present invention. After completion of the sterilization cycle, cap 404 of the outer vial is sealed, the vial is compressed to break inner glass vial 403, releasing the FES solution, which is adsorbed by sensor disk 402 containing the resistant spores or enzyme. Efficacy of the sterilization procedure is determined by placing the vial into chamber 416 of measuring device 414 and performing a fluorescent analysis for a period of minutes to hours to determine if there is any residual biological activity. In a hospital setting, it is advantageous to provide a measuring device that can monitor multiple indicators at one time. For purposes of illustration only, the device described here accepts four sensing elements at one time.

Each chamber 416 is machined into heating block 418, which controls the temperature of the vials. The sensor block is heated uniformly. Depending on the spore, temperatures in the range of 25–60° C. speed the kinetics of spore growth and enzymatic cleavage of the FES. One or more thermocouples (not shown) and heaters (not shown) are used to monitor and control the temperature.

Preferably, the chambers and vials are sized and shaped so as to provide intimate thermal and optical contact with measuring device 414 and to lock the vial into a fixed orientation in the chamber. This is achieved for example by providing molded hexagonal bight 405 to the base of both outer plastic shell 401 and chamber 416 that enable the vial to snap into position. In one embodiment, the base of chamber 416 is open such that the base of installed vial 401 becomes flush with the bottom of heater block 418. This enables fluorescent detection through the bottom surface of the vial.

Measuring device 414 includes integrated excitation and detection assembly 406, processor assembly 407 with optional display 408, housing 409 and base-plate 411. A communications port allows communication between the processor assembly and other network devices such as a computer, or a database, or other networks such as an ether-net, LAN, etc. Excitation/detection assembly 406 includes fiber terminal block assembly 420, optics assembly 425, electrical assembly 427, and heater block 418.

Fiber block assembly 420 includes a number of bundles of optical fibers that route light between optics assembly 425 and either sensing elements 412 or optical reference materials 426. Fiber block assembly 420 includes fiber block insert plate 422, which mates with heating block 418, and fiber block end plate 424 which mates with optics assembly 425. Preferably, insert plate 422 is made of polycarbonate and end plate 424 is made of aluminum to provide thermal isolation between heater block 418 and optics assembly 425. Insert plate 422 is joined to heater block 418 such that fiber insert holes 431, 432, 433, and 434 in insert plate 422 align with the four vial chamber holes in heater block 418. In addition, the backside of insert plate 422 includes raised platform 423 into which two additional holes 435 and 436 are drilled. Disk 426, made of an optical reference material, is placed into each of these holes and secured with a set screw. Optical reference disk 426 preferably comprises a fluorescing material such as "MACROLUX™ 10GN" brand fluorescently doped polycarbonate film, commercially available from Bayer AG, Leverkusen, Germany. The six holes in insert plate 422 are each adapted to receive a ferrule surrounding an end of a bundle of optical fibers. Likewise, end plate 424 of fiber block assembly 420 has seven holes 441–447 arranged in an array and adapted to receive ferrule-terminated optical fiber bundles. The seven holes in end plate 424 are positioned to align with optical excitation subassemblies and optical detection subassemblies housed within optics assembly 425. FIG. 4 shows a simplified representation of the paths of optical fiber bundles 451–462 between the six holes in insert plate 422 and the seven holes in end plate 424. A preferred routing of the optical fiber bundles is shown in detail in FIG. 6. A suitable optical fiber for each of the various bundles 451–462 is a fiber having a nominal outer diameter of 56 microns, with core glass of Schott LF5, clad glass of Schott 8250, Corning 7056 or 7052, and a clad thickness of 2–3 microns. An optical adhesive is used to secure bundled ends of the fibers into the ferrules. The bundles are preferably coated with optically opaque stiff plastic or rubber sheaths. The ends of bundles 451–462 are intermixed to present bifurcated sections such that the optical fibers received in one ferrule may lead to different ferrules at the opposite ends of the fibers, as depicted schematically in FIG. 6. Moreover, the optical fibers of each optical aperture are spatially randomized in the ferrule. Finally, the number of optical fibers allocated to each channel of a bifurcated cable preferably is greater than 100 and less than 2000, depending on the relative excitation or emission signal strengths handled by each fiber bundle during a typical operation.

Figure 6:
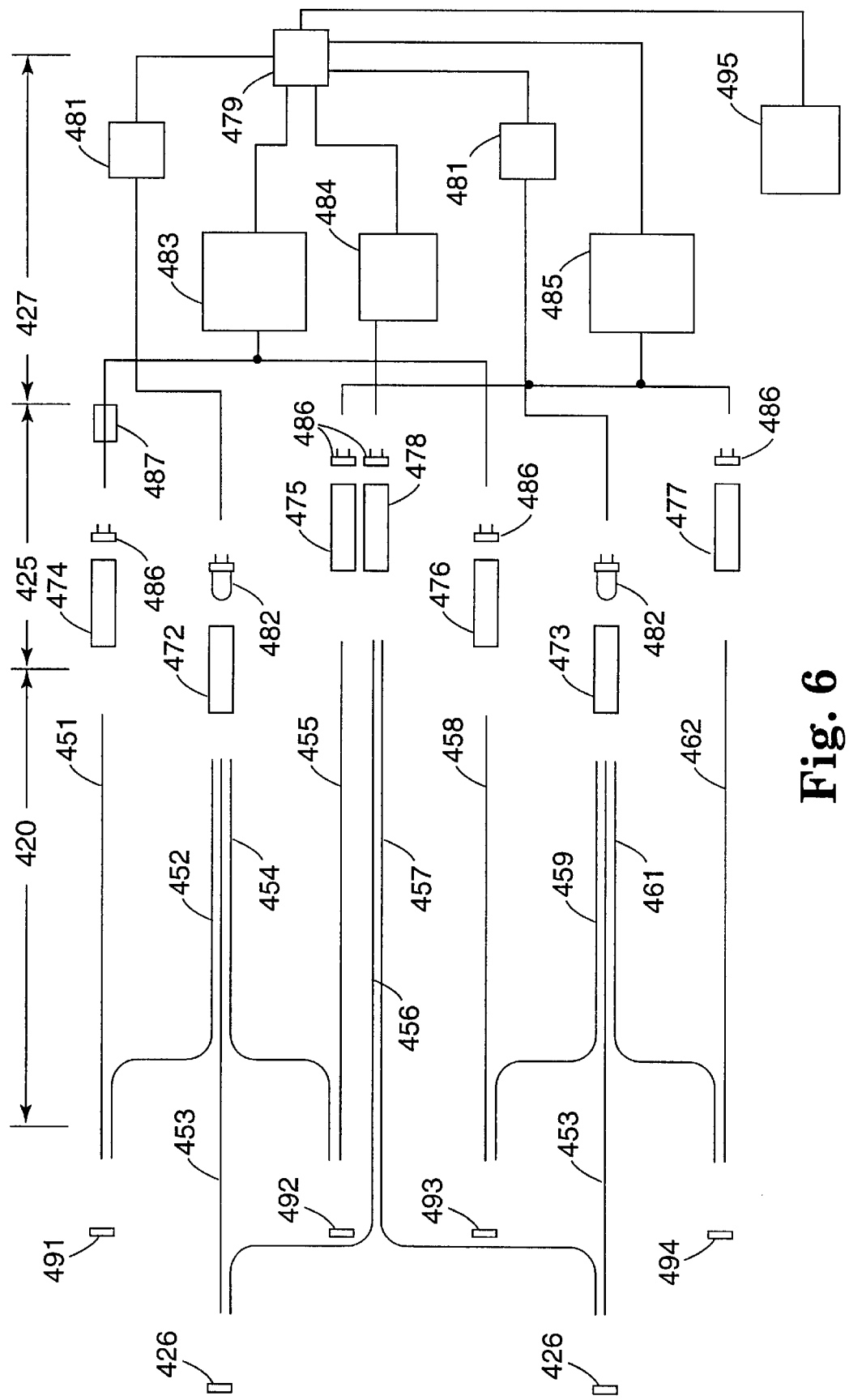
FIG. 6 is a schematic illustration showing among other things the various paths of optical fiber bundles of the measuring device illustrated in FIG. 3.

Measurement device 414 also contains optics assembly 425 which includes block 470 having cylindrical cavities that receive seven optical subassemblies 472–478, shown in FIG. 5. The cylindrical cavities contain optical retainers with ribs that support concentric stacking of optical elements at predefined separation distances for maximum optical efficiency. Optic subassemblies 472, 473 are excitation optic subassemblies, each comprising an optical stack consisting of (back to front) light emitting diode source 482 (such as a GaN LED part no. NLPB-500 from Nichia Chemical Industries), an excitation optical filter, and a focusing lens. With reference to FIG. 6, subassemblies 472 and 473 direct excitation light to bifurcated fiber optic bundles mounted in end plate 424 of fiber terminal block assembly 420. Optic subassemblies 474–478 are emission optic subassemblies, each comprising an optical stack consisting of (back to front) a photodiode detector (such at part no. S1133-14 from Hamamatsu, Bridgewater, N.J.), a focusing lens, an emission optical filter, and a collimating lens. With reference to FIG. 6, subassemblies 474–478 collect fluorescence return signals from bifurcated fiber optic bundles mounted on end plate 424, filter the emission and focus the filtered light signal onto the active region of the photodiode detector. Emission optic subassembly 478 is the same as that for emission subassemblies 474–477 except for the characteristics of the optical filter. Subassemblies 474–477 have optical filters chosen to match the emission profile of the FESs of the present invention after enzymatic cleavage in the sensor vial. Subassembly 478 has an optical filter chosen to match the emission profile of optical reference material 426.

Measurement device 414 also includes electrical assembly 427 that is in electrical communication with LEDs 482 and photodiode detectors 486 of optic assembly 425. Electrical assembly 427 includes controller 479 that provides clock timing and instructional signals to each of two drivers 481 that in turn energize LEDs 482 in sequence. Electrical assembly 427 includes three analog-to-digital converters 483, 484, and 485, shown in FIG. 6. A suitable analog-to-digital converter is catalog no. DDCl O1 from Burr-Brown Corp., Tucson, Ariz. Converter 483 is electrically connected with photodiodes 486 associated with optic subassemblies 474 and 476. Likewise, converter 485 is electrically connected to photodiodes 486 associated with optic subassemblies 475 and 477. Converter 484 is electrically connected to photodiode 486 associated with reference optic subassembly 478. Signal amplifier or opamp 487 (such as catalog no. AD795 from Analog Devices Inc., Norwood, Mass.) may be interposed in the electrical lead between any photodiode 486 and converters 483, 484, 485.

In use, controller 479 directs a signal to drivers 481 that, in turn energize corresponding LEDs 482. The light then travels from LED 482 through the adjacent fibers of fiber block assembly 420 to the corresponding sensing element, where it is absorbed. The sensing element then emits light at a different wavelength. The amount of emitted light is determined by the amount of fluorogenic enzyme substrate that has been cleaved by the enzyme. Light emitted from such a sensing element is directed through another optical fiber of fiber block assembly 420 to photodiode 486. The converter that is electrically connected to the photodiode provides a digital output signal that is representative of the amount of light flux detected. Controller 479, in accordance with a pre-selected time delay interval, reads data received from the appropriate converter and passes such data to processing unit 495.

As shown in FIG. 6, the light emitted from LED 482 and received in subassembly 472 is simultaneously directed to sensing elements 491 and 492 and to reference element 426. Light emitted from sensing element 491 is detected by photodiode 486 of subassembly 474 and converted to a digital signal by converter 483. Light emitted from reference disk 426 is detected by photodiode 486 of subassembly 478 and is converted to a digital signal by converter 484. Light emitted from sensing element 492 is detected by photodiode 486 of subassembly 475 and converted to a digital signal by converter 485. The digital data stream from converters 483–485 is received by controller 479 and forwarded to processor assembly 495.

In a similar fashion, light emitted from LED 482 of subassembly 473 is simultaneously directed to sensing elements 493 and 494 and to associated reference element 426. Light emitted from sensing element 493 is detected by photodiode 486 of subassembly 476 and converted to a digital signal by converter 483. Light emitted from reference disk 426 is detected by photodiode 486 of subassembly 478 and is converted to a digital signal by converter 484. Light emitted from sensing element 494 is detected by photodiode 486 of subassembly 477 and converted to a digital signal by converter 485. The digital data stream from converters 483–485 is received by controller 479 and forwarded to processor assembly 495.

The scheme shown in FIG. 6 enables the use of only three converters 483–485 even though four sensing elements and two reference elements 426 are in use. It also enables the use of only two LEDs 482. Such a time sharing or multiplexing arrangement conserves the number of components needed and conserves space so that the housing can be made small and the sensing elements can be more closely spaced. This is particularly advantageous for hand-held devices, where it may be desired to co-locate the sensing element, excitation assembly and detection assembly while providing a data link (electrical cable, wireless transmission etc.) to a processor assembly or a central data base.

The particular configuration shown in FIG. 6 illustrates the concept of using bifurcated fiber bundles as light guiding element 346 (FIG. 1*b*) when carrying out multiplexed detection of sensing elements of the present invention. There are many ways to configure such routing systems without deviating from the claimed invention. For example, the distal end of a bifurcated fiber-optic bundle, similar to one of the sample channels in FIG. 6, may be housed in a hand-held probe. This hand-held probe may be used to manually scan a fluorescent bar code generated by reacting an FES of the present invention with a pre-printed barcode mark containing a sterilization indicating spore or enzyme. In addition, there are many types of sensing elements for which bifurcated fiber bundling offers advantage. For example, optical routing of this type offers advantages for routing light to and from an array of sensor disks or micro-wells provided for a most microbial probable number analysis or for an enzyme kinetics profiling experiment.

Working Examples

The following examples are intended to farther illustrate, but not limit, the invention. All materials were obtained from, or are available from, Aldrich Chemical Co., Milwaukee, Wis., unless otherwise indicated.

Example 1

This example describes the synthesis of TUGal, as seen in Sequence 2 below. The 3-(2-thienyl) umbelliferone (II) can be reacted with acetobromo-α-D-glucose to yield β-TUGlc after removing protective groups.

acetic anhydride (61.3 mL). The solution was refluxed on an oil bath at 160° C. for 2 hours. After cooling, the mixture was poured into ice cold water. Light yellow solids immediately precipitated and were collected by filtration. Recrystallization from acetone gave compound I as pale yellow needles (19.72 g). The structure of the product was confirmed by NMR.

3-(2-thienyl) umbelliferone (II)

To a solution of 3-(2-thienyl)-7-umbelliferyl acetate (compound I, 19.19 g) in methanol (250 mL), was added an 18% aqueous solution of HCl (315 mL). The mixture was

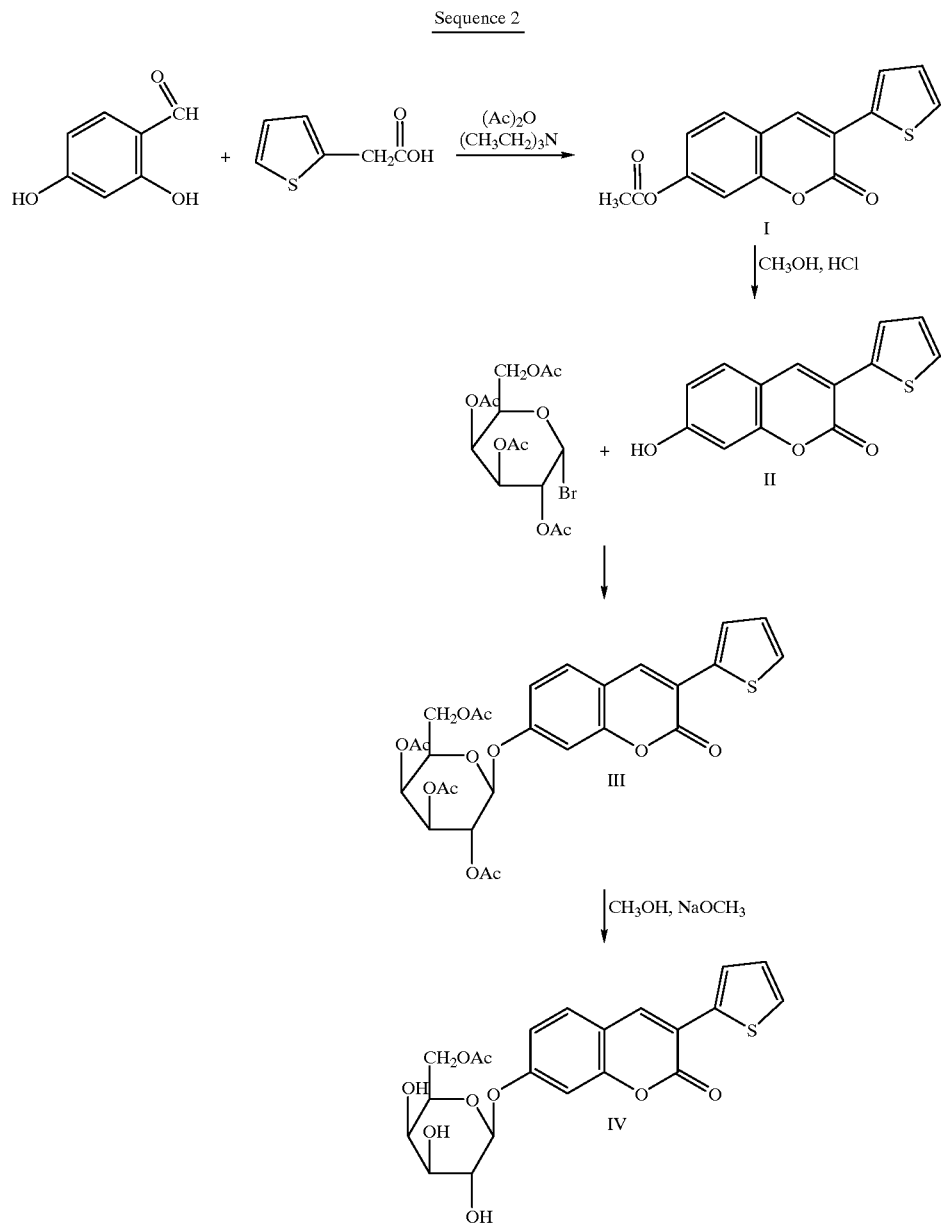

Sequence 2

3-(2-thienyl)-umbelliferyl acetate (I)

To a mixture of 2,4-dihydroxybenzaldehyde (9.65 g) and 2-thiopheneacetic acid (9.93 g, Lancaster Synthesis, Windham, N.H.) was added triethylamine (12.26 mL) and refluxed on a water bath for 4 hours. One half of the methanol was removed under vacuum, and the remaining solution was poured into water. The yellow-green solid II (15.01 g) that precipitated was collected by filtration. The structure of the product was confirmed by NMR.

(3-(2-thienyl)-umbelliferyl)-2,3,4,6-tetra-O-acetl-β-D-galactoside (IIIA)

To a solution of 3-(2-thienyl) umbelliferone (compound II, 4.0 g) and acetobromo-α-D-galactose (6.73 g, Sigma Chemical Company, St. Louis, Mo.) in acetone (40 mL) was added 1.0 M NaOH (20 mL). After stirring overnight at room temperature, the residual acetone was removed under vacuum and the residue was dissolved in chloroform. The solution was extracted twice with 5% aqueous NaOH and twice with water to remove any free 3-(2-thienyl)-umbelliferone (II). The organic phase was dried over MgSO$_4$ and the chloroform was evaporated under vacuum to give IIIA (5.32 g). The structure of the product was confirmed by NMR.

(3-(2-thienyl)-umbelliferyl)-2,3,4,6-tetra-O-acetyl-β-D-glucoside (IIIB)

To a solution of 3-(2-thienyl) umbelliferone (compound II, 3.0 g) and acetobromo-α-D-glucose (5.05 g, Sigma Chemical Company, St. Louis, Mo.) in acetone (30 mL) was added 1.0 M NaOH (15 mL). After stirring overnight at room temperature, the residual acetone was removed under vacuum and the residue was dissolved in chloroform. The solution was extracted twice with 5% aqueous NaOH and twice with water to remove any free 3-(2-thienyl)-umbelliferone (compound II). The organic phase was then dried over MgSO$_4$ and the chloroform evaporated under vacuum to give compound IIIB (2.33 g). The structure of the product was confirmed by NMR.

3-(2-thienyl)-umbelliferyl-7-β-D-zalactoside (β-TUGab) (IV)

To a solution of the acetylated sugar derivative of 3-(2-thienyl) umbelliferone (5.21 g) in methanol (52 mL) was added 1.0 M sodium methoxide solution (5.2 mL) with shaking. The solution was stirred for 30 min and the yellow solids that precipitated were collected by filtration and recrystallized from 50% methanol in water to give compound IV (3.00 g). The structure of the product was confirmed by NMR.

3-(2-thienyb)-umbelliferyl-7-β-D-lucoside (β-TUGlc)

To a solution of the acetylated glucose derivative of 3-(2-thienyl) umbelliferone (1.18 g) in 5:5:4 methanol:tetrahydrofuran:acetone (28 mL) was added 1.0 M sodium methoxide solution (22 mL) with shaking. The solution was stirred for 30 min and was diluted with water (250 mL). This solution was acidified with concentrated HCl and the green precipitate (0.56 g) was collected by filtration. The structure of the product was confirmed by NMR.

The synthesis of 2-furanacetic acid from furfural and rhodanine is seen below as Sequence 3. The resulting 2-furanacetic acid can be reacted according to the scheme in Sequence 2 above to give the furyl analog: 3-(2-furyl) umbelliferyl-β-D-glycoside (FUG).

Sequence 3

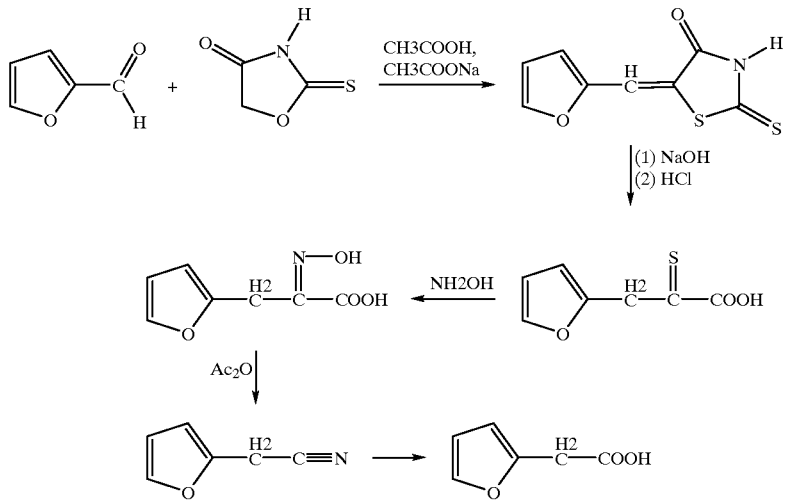

Furfuryl rhodanine

To a solution of 2-furaldehyde (43 mL) in hot glacial acetic acid (340 mL) was added rhodanine (68.4 g) and sodium acetate (128.4 g). The solution was refluxed for 0.5 hour and poured into water (2.6 L). The precipitate was collected by filtration and washed with water (1.4 L), ethanol (500 mL), and diethyl ether (200 mL). Recrystallization from acetone gave furfuryl rhodanine (97.4 g). The structure of the product was confirmed by NMR.

3-α-furyl-2-thioketopropnaloic acid

Furfuryl rhodanine (34.0 g) was refluxed in 15% aqueous NaOH (150 mL) for 0.5 hour. The solution was allowed to cool to room temperature and was filtered. The filtrate was cooled in an ice bath and 10% aqueous HCl (200 mL) was added. The yellow crystals were filtered and recrystallized from methanol to give 3-α-furyl-2-thioketopropanoic acid. The structure of the product was confirmed by NMR.

3-α-furyl-2-oximinopropanoic acid

To a warm solution of hydroxylamine hydrochloride (18.0 g) in water (16 mL) was added a solution of sodium ethoxide (22.0 g) in ethanol (187 mL). The resulting solution was filtered and the filtrate was added to 3-α-furyl-2-thioketopropanoic acid (20.0 g). After refluxing for 0.5 hour, the solution was cooled with an ice bath and 5% aqueous NaOH (60 mL) was added. The mixture was filtered and the cold filtrate was slowly acidified with 10% aqueous HCl (56 mL). The solution was extracted with ether and the organic phase was dried with MgSO$_4$. Evaporation of the ether under vacuum gave 3-α-furyl-2-oximinopropanoic acid as a sticky, orange paste. The structure of the product was confirmed by NMR.

2-furanacetonitrile

3-α-furyl-2-oximinopropanoic acid was combined with acetic anhydride in a 1 g: 4.83 mL ratio. The mixture was refluxed on a hot water bath for 0.5 hour. Steam distillation of the mixture afforded an azeotrope of 2-furanacetonitrile and water between 90–100° C. The mixture was neutralized with a saturated aqueous solution of sodium carbonate, and was extracted into ether. The organic phase was dried with $MgSO_4$ and distilled under vacuum at 105–115° C. to give 2-furanacetonitrile. The structure of the product was confirmed by NMR.

2-furanacetic acid

A mixture of 2-furanacetonitrile (6.14 g), KOH (4.0 g), and water (25 mL) was refluxed for 1 hour and then cooled. Following extraction with ether, the aqueous layer was acidified to pH 2.0 with concentrated aqueous HCl. This solution was extracted with ether, and the organic phase was dried over $MgSO_4$ and evaporated under vacuum to yield 2-furanacetic acid. The structure of the product was confirmed by NMR.

Example 2

Characterization

NMR spectra were run on a Varian UNITY 500 (Varian Analytical Instruments, Santa Clarita, Calif.) in $CDCl_3$ and DMSO-$d_6$ as indicated. Extensive 2-dimensional NMR studies were performed on TUG including distortionless enhancement via polarization transfer (DEPT), correlated spectroscopy (COSY), total correlated spectroscopy (TOCSY), heteronuclear multiple quantum coherence (HMQC), and heteronuclear multiple bond correlation (HMBC). Mass spectroscopy was also performed on some of the samples using the positive-ion thermal desorption electron impact (EI) techinique. Fluorescence measurements were made using a SPEX Fluorolog™ Series spectrofluorimeter (SPEX Industries, Inc., Edison, N.J.).

Determination of Fluorescence Characteristics

A stock solution of 3-(2-thienyl)-umbelliferone (TU) was prepared by dissolving $2.0 \times 10^{-3}$ g of the compound in 1100 μl of ethanol and 900 μl of distilled water. Fifty microliters of this solution were then diluted to 4.00 mL in a series of 50 mM sodium phosphate buffer solutions, each having a different pH, corresponding to the traces of FIG. 7a, as shown in Table 1. The final concentration of TU was $3.08 \times 10^{-4}$ M.

Figure 7A:
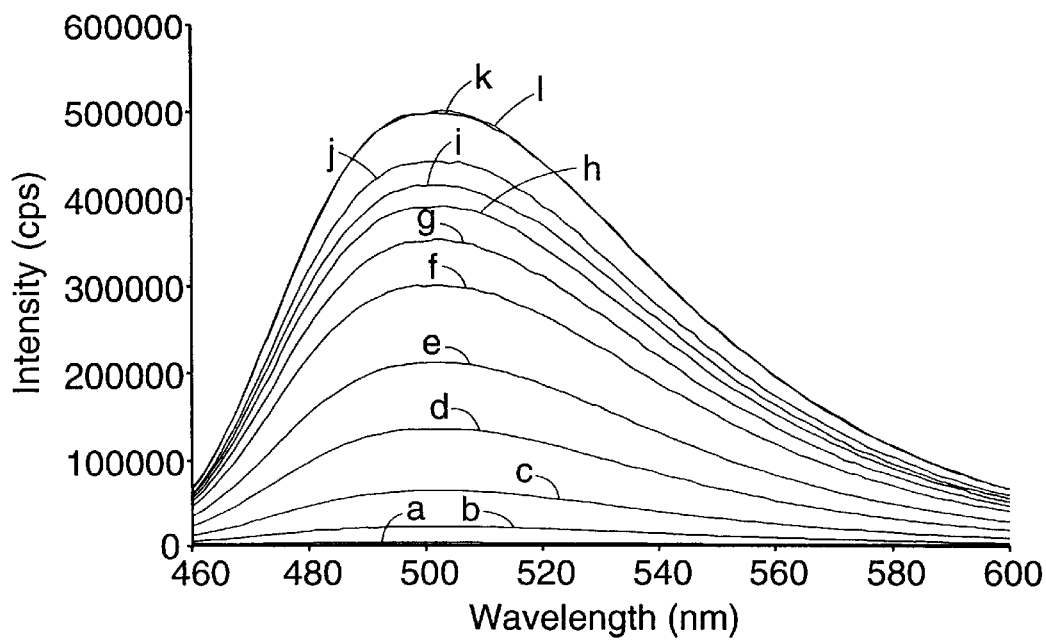
FIG. 7a shows the fluorescence emission spectra for 3-(2-thienyl)umbelliferone (TU) anion as a function of pH when the sample is excited at 450 nm.

FIG. 7a shows fluorescence emission spectra for each of these solutions as a function of pH when the sample is excited at 450 nm (SPEX Fluorolog™ Series spectrofluorimeter, SPEX Industries, Edison, N.J.). The emission is centered at 502 nm and is associated with the TU anion. Below pH 10, the emission increases with increasing pH. Above pH 10, the fluorescence decreases, probably due to hydrolysis of the coumarin lactone. Further fluorescence measurements in a narrower range of pH values (7.05 to 8.20) allowed determination of the pKa. From this data the pKa of 3-(2-thienyl)-umbelliferone was determined to be 7.57±0.03.

TABLE 1

| Trace | pH | Trace | pH |
|---|---|---|---|
| a | 5.0 | g | 8.0 |
| b | 6.0 | h | 11.0 |
| c | 6.5 | i | 8.5 |
| d | 7.0 | j | 9.0 |
| e | 7.3 | k | 9.5 |
| f | 7.6 | l | 10 |

Figure 7B:
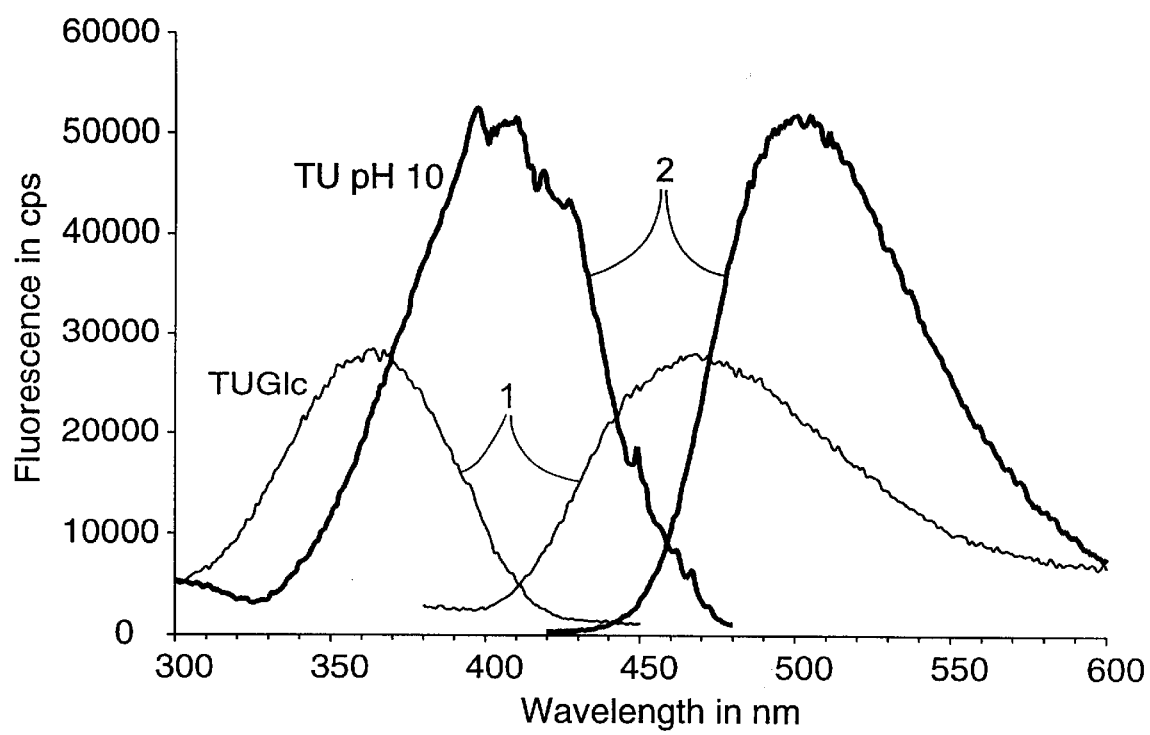
FIG. 7b shows the fluorescence excitation and emission spectra for β-TUGlc and for TU anion.

FIG. 7b shows the excitation and emission spectra for a 5 μM solution of β-TUGlc in 50 μM phosphate buffered saline (PBS) at pH 7.6 and for a 5 μM solution of 3-(2-thienyl)-umbelliferone in 50 mM PBS at pH 10.0. β-TUGlc exhibits an excitation maximum near 380 nm and an emission maximum near 460 nm (Trace 1). The corresponding TU anion exhibits an excitation maximum near 410 nm and an emission maximum near 502 nm (Trace 2). Similar data can be obtained for β-TUGal derivatives. The data of FIG. 7b indicate that the TU anion can be selectively excited in a spectral window for 430 nm to 480 nm in the presence of unreacted β-TUGlc. The spectral window overlaps with the emission spectrum of GaN LED light sources. By using an excitation source filter centered in this spectral window and an emission source filter centered between 480 nm and 600 nm, the formation of TU anion can be measured as a product of the enzymatic cleavage of β-TUGlc without interference from β-TUGlC fluorescence. As shown in FIG. 7a, the intensity of this emission signal depends on pH, and significant amounts of the TU anion can be detected at physiological pH values of 7.2–7.6, where enzyme activity is preserved, in contrast to known methyl umbelliferone derivatives having a pKa of 7.8. Thus, using the fluorogenic compounds of the present invention, enzyme activity can be monitored continuously, without the need to withdraw an aliquot of the reaction mixture and adjust the pH to form a fluorescently detectable product.

Example 3

Enzyme Assays Using β-TUGal

β-Galactosidase activity was continuously assayed at pH 7.6 in a fluorometer using front face detection. This pH was near the pKa for the 3-(2-thienyl) umbelliferone hydrolysis product of TUGal and was chosen so that TU would be approximately 50% deprotonated. Hence, the hydrolysis reaction could be monitored continuously without the need to add base to develop a fluorescent signal.

Figure 8:
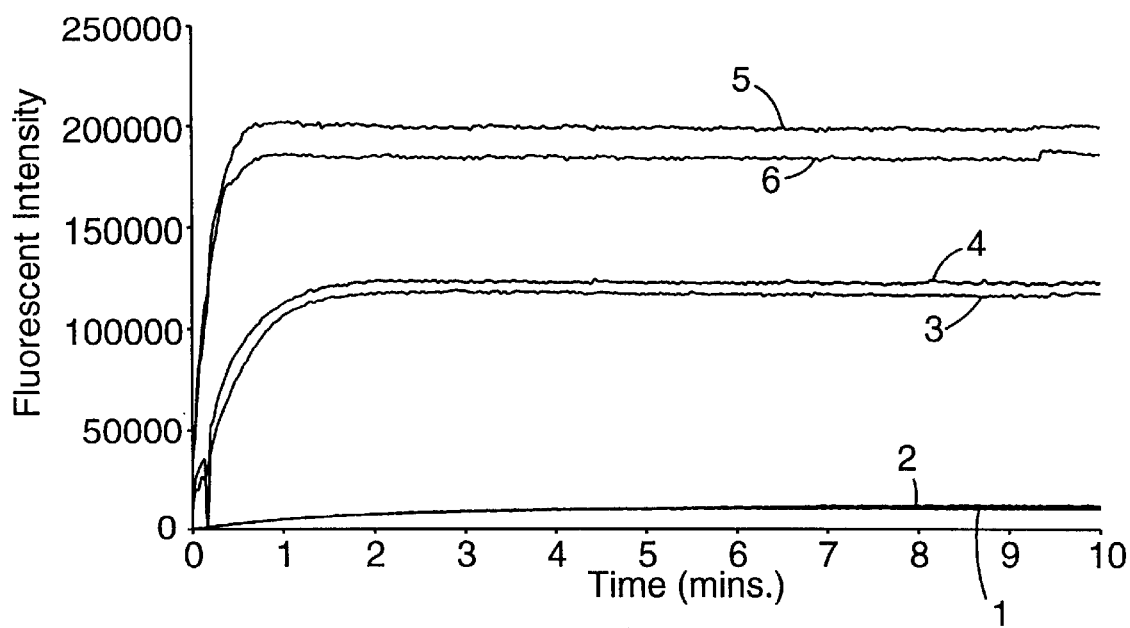
FIG. 8 shows the fluorescence intensity at 502 nm versus time for cleavage of three different concentrations of β-TUGal by β-galactosidase.

Samples were excited at 450 nm and emission was monitored at 502 nm. FIG. 8 shows the fluorescence detected for three initial concentrations of β-TUGal and enzyme. Addition of β-galactosidase caused a rapid increase in fluorescence due to the liberation of TU anion. Final intensities were correlated with the initial concentration of TUGal, as seen in Table 2. In FIG. 8, traces 1 and 2 correspond to a TUGal concentration of $1 \times 10^{-6}$ M, traces 3 and 4 correspond to $1 \times 10^{-5}$ M, and traces 5 and 6 correspond to $2 \times 10^{-5}$ M TUGal concentration. Results similar to this were also seen with cleavage of β-TUGlc by β-glucosidase.

β-Galactosidase

Assay solutions were prepared as follows: a 100 mM sodium phosphate solution, pH 7.6, a 30 mM $MgCl_2$ solution, a solution of β-TUGal ($3.08 \times 10^{-2}$ M, Example 1) in N,N-dimethyl formamide (DMF), and a solution of β-galactosidase (1.0 units/μl) from E. coli (Grade VIII, Sigma Chemical Co., St. Louis, Mo.) reconstituted in 100 mM sodium phosphate, pH 7.3. Details of mixing are shown below in Table 2. The corresponding fluorescence traces are shown in FIG. 8.

TABLE 2

TUGal Enzyme Assay

| FIG. 8 Traces | TUGal soln. | DMF | Buffer | MgCl$_2$ | Enzyme | Total Volume* | [TUGal] |
|---|---|---|---|---|---|---|---|
| 1, 2 | 0.13 | 99.87 | 3350 | 150 | 0.5 | 3600.5 | $1 \times 10^{-6}$ |
| 3, 4 | 1.3 | 98.7 | 3345 | 150 | 5 | 3600.0 | $1 \times 10^{-5}$ |
| 5, 6 | 2.6 | 97.4 | 3340 | 150 | 10 | 3600.0 | $2 \times 10^{-5}$ |

*All volumes are given in microLiters

All reagents were kept on ice until their time of use. From them, two solutions were prepared: the substrate solution and the enzyme solution. The substrate solution was prepared in a sample vial by further dilution of the β-TUGal solution in DMF. The preparations gave final concentrations of 1, 10, and 20 μM β-TUGal. In a separate cuvette, the phosphate buffer was combined with 150 μL MgCl$_2$ solution and the appropriate amount of reconstituted β-galactosidase to make the enzyme solution. This was then incubated for seven minutes at 37° C. Following incubation, the substrate solution was added and the fluorescence was measured by front face detection over a 10-minute period at 37° C. The results of these measurements are shown in FIG. 8.

β-Glucosidase

The activity of β-glucosidase (Sigma Chemical Co.) was assayed analogously to that of β-galactosidase. Only one concentration, 1×10$^{-5}$ M TUGlc, was tested.

Example 4
Synthesis of α-TUGlc

The current Attest# Rapid Readout Biological Indicator (3M, St. Paul, Minn.) for steam autoclaves is based on the cleavage of α-MUGlc by B. stearothermophilus at 60° C. Synthesis of the corresponding α-TUGlc is given below in Sequence 4.

Acetochloro-β-D-glucose

To a solution of β-D-glucose pentaacetate (20 g) in CHCl$_3$ (100 mL) was added AlCl$_3$ (3.6 g). After stirring at room temperature, toluene (100 mL) was added, followed by silicic acid (2 g). The mixture was stirred for a few minutes and the precipitate was removed by filtration. The solution was partially concentrated under vacuum and extracted with ice cold water (25 mL). The organic phase was concentrated to a syrupy mixture and ether was added to precipitate acetochloro-β-D-glucose as a powder (12 g).

3-(2-Thienyl) umbelliferyl-2,3,4,6-tetra-O-acetyl-α-D-glucoside

To a solution of acetochloro-α-D-glucose (1.46 g) in hexamethylphosphoramide (15 mL) was added 3-(2-thienyl) umbelliferyl sodium salt (1.06 g). The bright green solution was stirred overnight at room temperature and poured into ice cold water. After stirring for several hours, the solution was placed in a refrigerator for 5 days. The precipitate was filtered and dissolved in CHCl$_3$. Following extraction with 5% NaOH and water, the organic layer was dried with MgSO$_4$ and the solvent was evaporated under vacuum to give a yellow syrup (0.5 g).

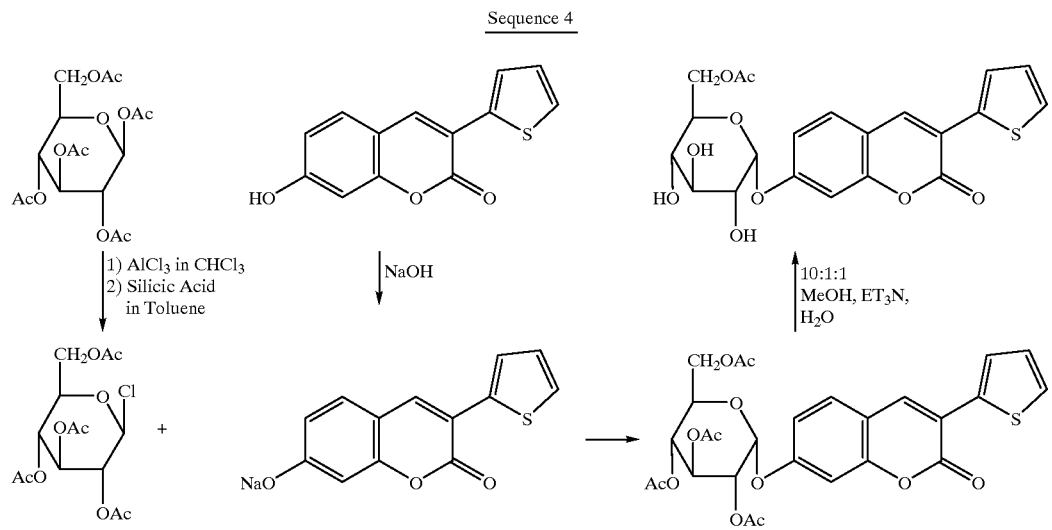

Sequence 4

Sodium Salt of 3-(2-thienyl) umbelliferone 3-(2-thienyl) umbelliferone (14.46 g) was dissolved in 1.0 M NaOH (60 mL). Orange solids quickly appeared but went back into solution. The mixture was then frozen in a dry ice/acetone bath and lyophilized to give a brownish orange solid (15.91 g).

α-TUGlc

The acetylated sugar derivative was dissolved in of 10:1:1 methanol: triethylamine:water (40 mL) and stirred overnight at room temperature. The solution was concentrated under vacuum to a syrup and methanol was added to precipitate α-TUGlc as a yellow solid (8 mg).

Example 5
*Escierichia coli* Detection

*E. coli* is known to secrete extracellular galactosidase. In a selective growth media, *E. coli* can be detected based on development of this enzyme activity. Varying concentrations of 3-(2-thienyl) umbelliferyl-β-D-galactoside (β-TUGal) indicator were assayed against three known concentrations of *E. coli* P18 cells: ca $10^3$, $10^2$, and 10 cells/mL. Viable cell counts were determined using Petrifilm (3M, St. Paul, Minn.). Adjusting for the dilutions used in the fluorescence detection experiments, cell counts were approximately 56, 5.6, and 0.56 cells per well.

Figure 9:
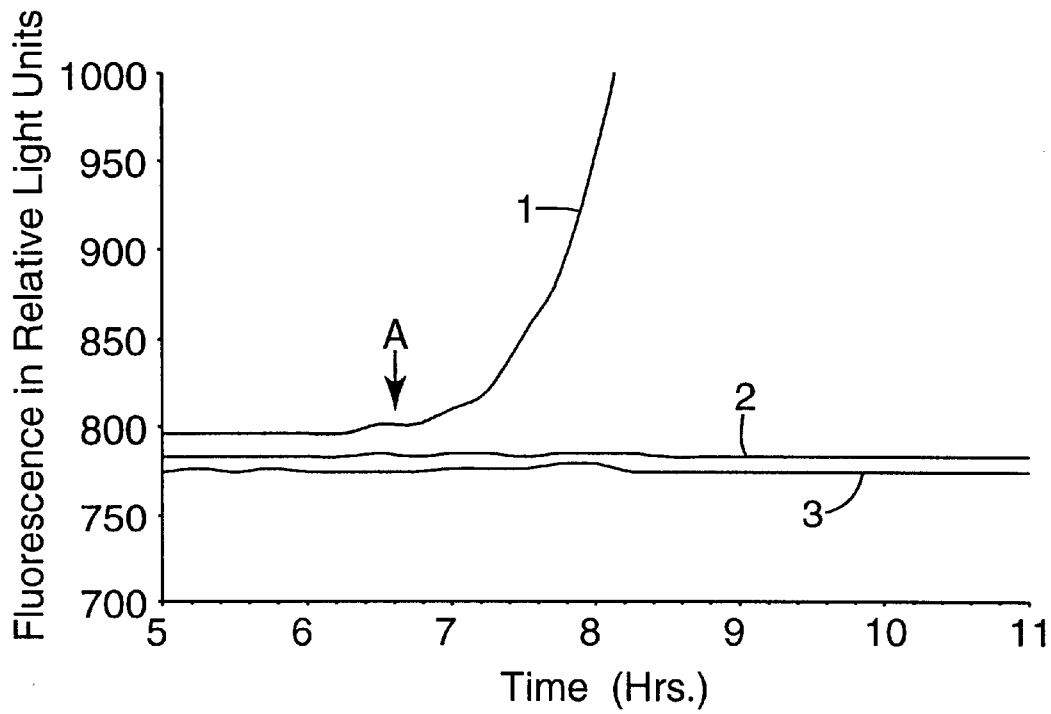
FIG. 9 shows the onset of detection for the most concentrated *Escherichia coli* (*E. coli*) culture from FIG. 11.

All three concentrations of β-TUGal showed positive results for the 56 and 5.6 cell *E. coli* concentrations at times between 6.5 and 10.5 hrs. Starting with 56 cells/mL and an indicator concentration of 62 μM β-TUGal, a growing microcolony was detected in 6.5 to 8 hrs. Starting with 6 cells/mL a growing microcolony was detected in 7.5 to 9 hrs. In the 0.56 cell concentration, 3 of the 10 concentrations showed positive results, since at this low concentration, not all wells may have had bacteria in them. Higher concentrations of substrate and bacteria led to the fastest detection times. The fastest occurred with 56 cells per well and 62 μM β-TUGal and indicated a positive result after 6.5 hrs (time A), as shown in trace 1 of FIG. 9. Traces 2 and 3 of FIG. 9 were blank (control) samples.

Figure 10:
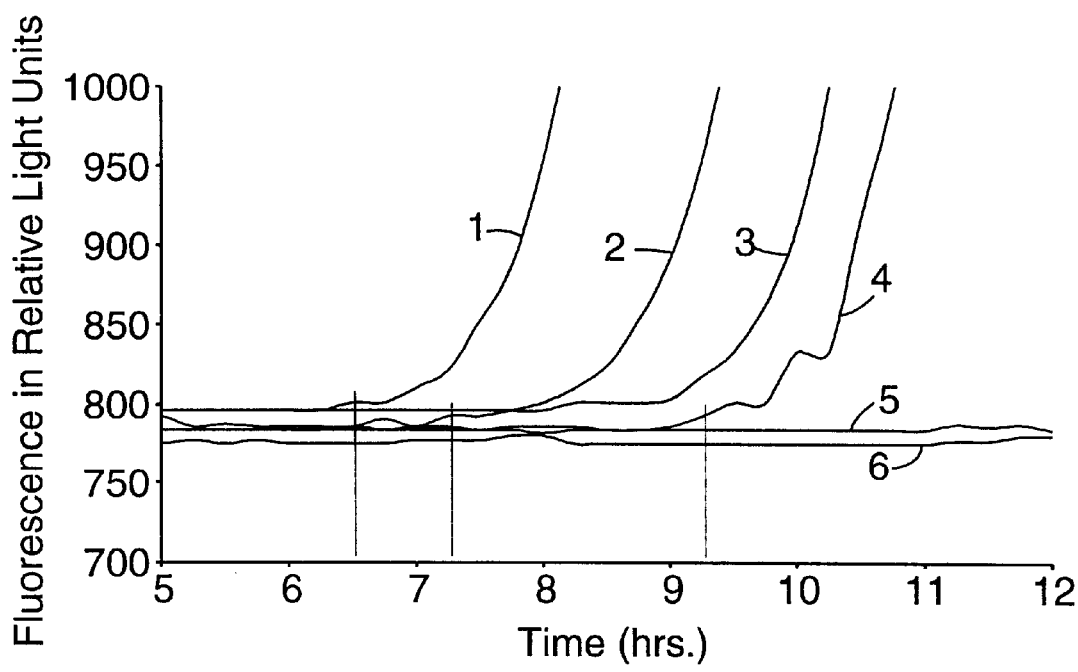
FIG. 10 shows the onsets of detection for the *E. coli* cultures shown in FIG. 11.
Figure 11:
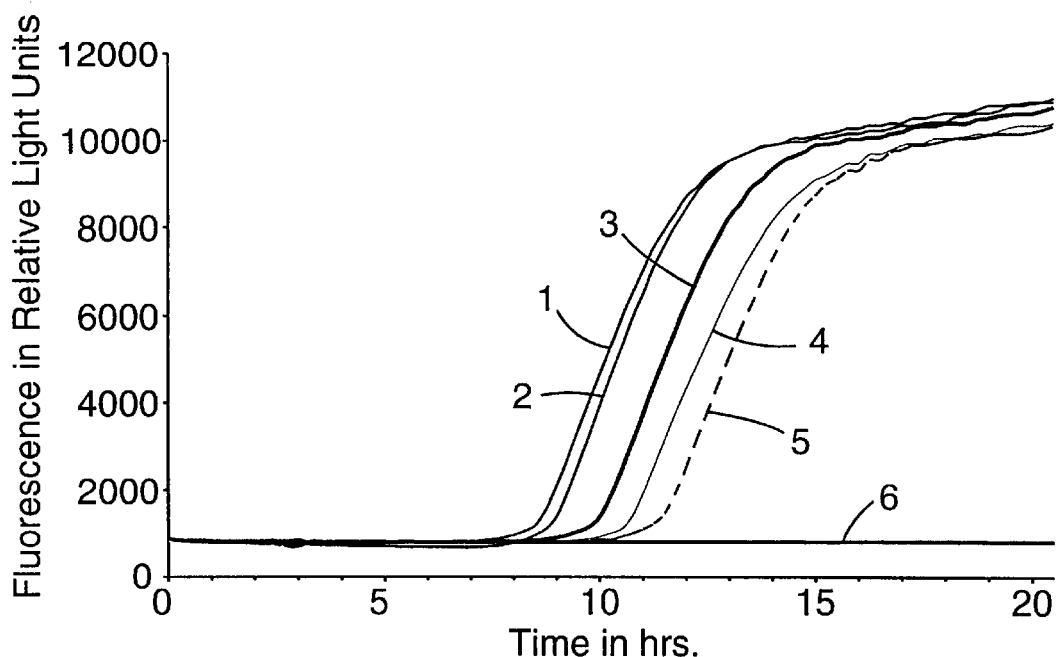
FIG. 11 shows fluorescence intensity vs time for the cleavage of β-TUGal by growing cultures of *E. coli*.

FIGS. 10 and 11 show the range of time where detection was confirmed with the 62 μM β-TUGal from all three concentrations of *E. coli*. In FIG. 10, traces 1 through 4 represent, respectively, *E. coli* concentrations of 56 cells, 5.6 cells, 5.6 cells, and 0.56 cells per well. Traces 5 and 6 represent blank (control) samples. In FIG. 11, traces 1 through 5 represent, respectively, *E. coli* concentrations of 56 cells, 56 cells, 5.6 cells, 5.6 cells, and 0.56 cells per well. Trace 6 represents a blank (control) sample. FIGS. 10 and 11 represent two distinct regimes of fluorescent detection. It is to be noted that FIG. 10 represents detection of relative light units in the range of 750 to 1000 units, whereas FIG. 11 represents detection above 2000 relative light units. FIGS. 3 and 4 show that for *E. coli* concentrations of 56 cells per well, i.e., approximately 103 cells per mL, positive detection can occur as early as 6.5 hours from the start of incubation.

In this example, detection of small quantities of *E. coli* in a continuously monitored experiment at pH 7.7 demonstrated improved detection over conventional methods using MUGal as a substrate.

Culture and Dilutions

A fresh overnight culture of *E. coli* P18 was prepared and grown in tryptic soy broth (TSB, Sigma Chemical Co., St. Louis, Mo.). Ten μL of this stock culture was diluted into 99 mL of Butterfields phosphate buffer (Hardy Diagnostics, Santa Maria, Calif.) to give a 10,000 fold dilution. Next, 10 mL of this new solution was diluted into 90 mL of phosphate buffer to give an approximate *E. coli* concentration of 103 cells/mL. Two more dilutions in this same manner yielded cultures of $10^2$ and 10 cells/mL.

Growth Media

Five hundred mL of growth media for the cells was prepared from the following: 5.0 g Difco bacto-tryptone (Difco Laboratories, Detroit, Mich.) 2.5 g Difco bacto-yeast extract, 0.54 g $KH_2PO_4$, 2.99 g $Na_2HPO_4$, and 0.5 g sodium pyruvate (Sigma Chemical Co., St. Louis, Mo.). The growth media was then sterile-filtered through a 0.8 μm filter.

Experimental Setup

Three concentrations of *E. coli* cells were used to measure detection times: $10^3$, $10^2$, and 10 cells/mL. Each of these cell concentrations was also assayed against varying concentrations of the fluorescent indicator 3-(2-thienyl) umbelliferyl-β-D-galactoside (β-TUGal). These β-TUGal solutions were prepared by dilutions of a $2.46 \times 10^{-2}$ M (in DMF) stock solution in the *E. coli* growth media.

All materials (growth media, 50 μL cell solutions, and β-TUGal solutions) were pipetted to a final volume of 200 μL in a microwell plate. Table 3 provides experimental detail by showing the pipetting grid used in the Example.

Fluorescence Detection

Fluorescence was measured at 37° C. in a CytoFluor™ fluorometer with excitation centered at 450 nm (bandwidth 50 nm), and emission monitored at 530 nm (bandwidth 25 nm). Data were taken every 15 minutes for a period of 21 hours.

Cell Concentration Determination

Each of the three lowest dilutions of the *E. coli* culture were counted on Petrifihm by plating 1 mL of each and growing overnight at 37° C.

TABLE 3

| | Pipetting grid used for experimental setup. | | | | | | |
|---|---|---|---|---|---|---|---|
| Final TUGal concentration | 62 μM | 31 μM | 15.5 μM | 6.2 μM | 3.1 μM | No TUGal | No Cells |
| Cell Solution | 50 | 50 | 50 | 50 | 50 | 50 | 0 |
| TUGal Solution | 20 | 10 | 5 | 2 | 1 | 0 | Varied* |
| Growth Media | 130 | 140 | 145 | 148 | 149 | 150 | Varied* |
| Total Volume** | 200 | 200 | 200 | 200 | 200 | 200 | 200 |

*"Varied" denotes that these values were not constant because a cell-less blank was prepared at each concentration of TUGal.
**All volumes are given in microliters

Example 6
*Bacillus stearothermophilus* Detection with β-TUGlc

Figure 12:
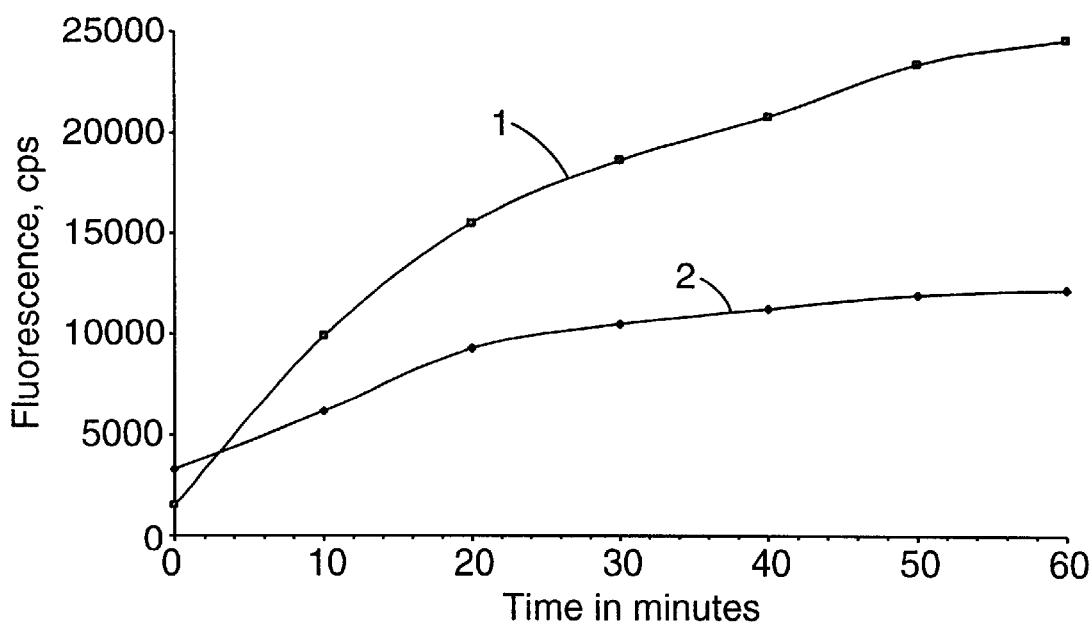
FIG. 12 shows relative fluorescence intensity versus time for the cleavage of β-TUGlc by two different concentrations of *Bacillus stearothermophilus*.

*B. stearothermophilus* spores (commercially available as ATCC 7953 or ATCC 8005 from American Type Culture Collection, Rockville, Md.) were diluted in growth media to a concentration of $1.3 \times 10^8$ cells per mL. Dilutions to $10^7$ cells/mL and $10^6$ cells/mL were prepared using 50 mM sodium phosphate, pH 7.6. Aliquots of these solutions were incubated with β-TUGlc ($2 \times 10^{-6}$ M) at 56° C. in a fluorimeter and fluorescence was monitored with excitation at 450 nm and emission at 502 nm. FIG. 12 shows that fluorescence changes were evident in less than 10 minutes in samples containing both $10^7$ (trace 1) and $10^6$ (trace 2) cells/mL. The rapid increase in fluorescence upon exposure of the spores to β-TUGlc demonstrated the presence of residual β-glucosidase in the spore coat. In a similar manner, spore solutions that had been steam-sterilized for 20 minutes at 121° C. were mixed with the β-TUGlc. In this case, the fluorescent background was small and constant, indicating no enzymatic cleavage reaction. The growth medium for this Example was prepared by dissolution of trypticase peptone (5 g), phytone peptone (12 g) and L-alanine (17 mg) in 1 liter of water.

Example 7
Bacterial Hydrolysis of α-TUGlc

Figure 13:
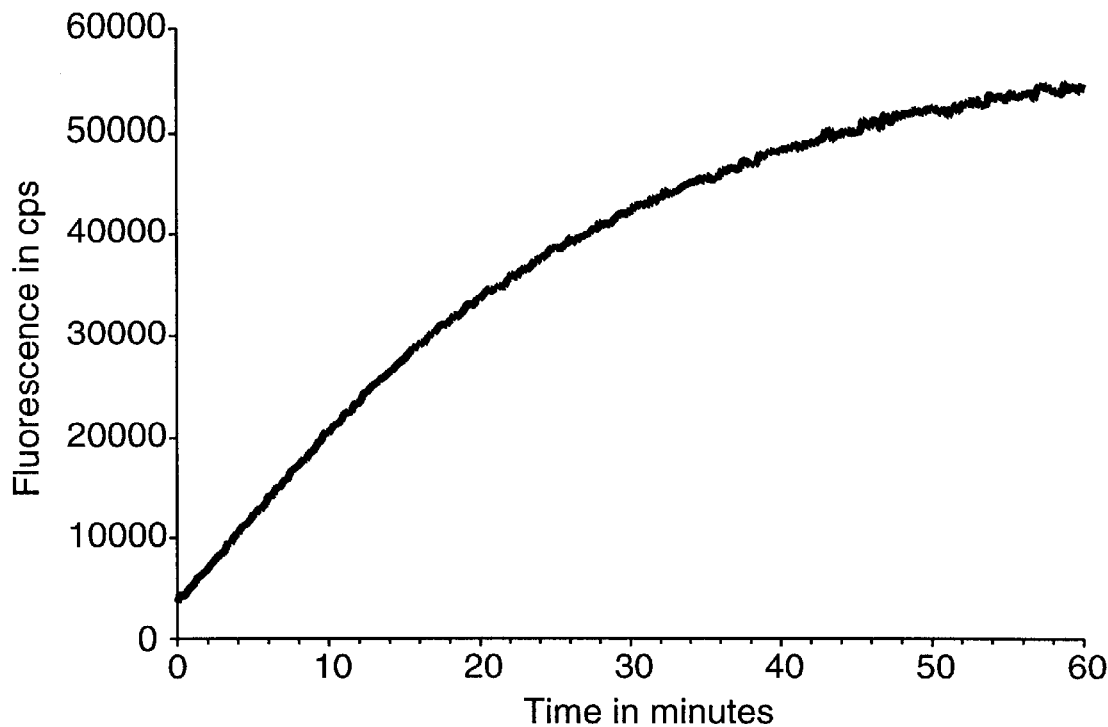
FIG. 13 shows relative fluorescence intensity at 502 nm for cleavage of α-TUGlc by *B. stearothermophilus*.

100 μL of *B. stearothermophilus* spores (initial conc. 1×10$^8$ cells/mL) was added to 890 μL of growth media and the mixture was incubated at 56° C. for 7 minutes. 10 μL of 246 μM α-TUGlc (prepared as described in Example 4) was then added and fluorescent emission was observed at 502 nm while exciting at 450 nm. Fluorescence increased rapidly in the first 20 minutes and began to slow down after 60 minutes (SPEX Fluorolog™ Series spectrofluorimeter, SPEX Industries, Inc., Edison, N.J.). This increase in fluorescence indicates enzymatic cleavage of the substrate. However, because the spores have both β- and α-glucosidase activity, the stereochemistry of the substrate can not be judged. The results from this Example are shown in FIG. 13.

Example 8
Enzymatic Hydrolysis of α-TUGlc

Figure 14:
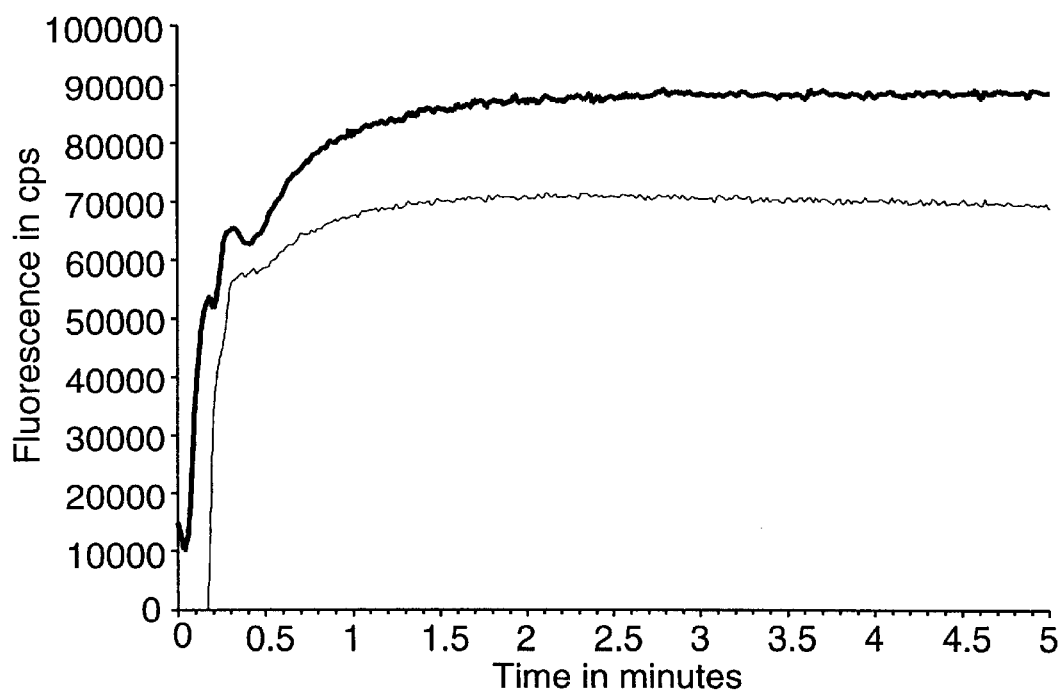
FIG. 14 shows relative fluorescence intensity at 502 nm for cleavage of (α-TUGlc by α-glucosidase.

Commercially prepared *B. stearothermophilus* α-glucosidase (Sigma Chemical Company, St. Louis, Mo.) was used as 100 units per mL (1 unit produces 1 limole of product per minute). 10 μL of this solution was added to 980 mL of growth media to simulate the actual environment of the bacterial spores. This enzyme and media mixture was then incubated for 7 minutes at 60° C., at which time 10 μL of 246 μM α-TUGlc (prepared as described in Example 4) was added. The reaction was monitored on the SPEX Fluorolog™ spectrofluorimeter by exciting at 450 nm with emission at 502 nm. The increase in fluorescence indicated that hydrolysis of the substrate occurred quite rapidly with the $V_{max}$ appearing in about 2 minutes. FIG. 14 shows the fluorescence of two hydrolysis trials, both at the nominal concentration noted above. Variation in fluorescence may be due to variation in activity of the bacterial enzyme per mL of mixture. The assays of examples 7 and 8 confirmed the presence of the α-glucoside derivative.

Example 9
LED Based Epifluorescence Detection Apparatus

Figure 15:
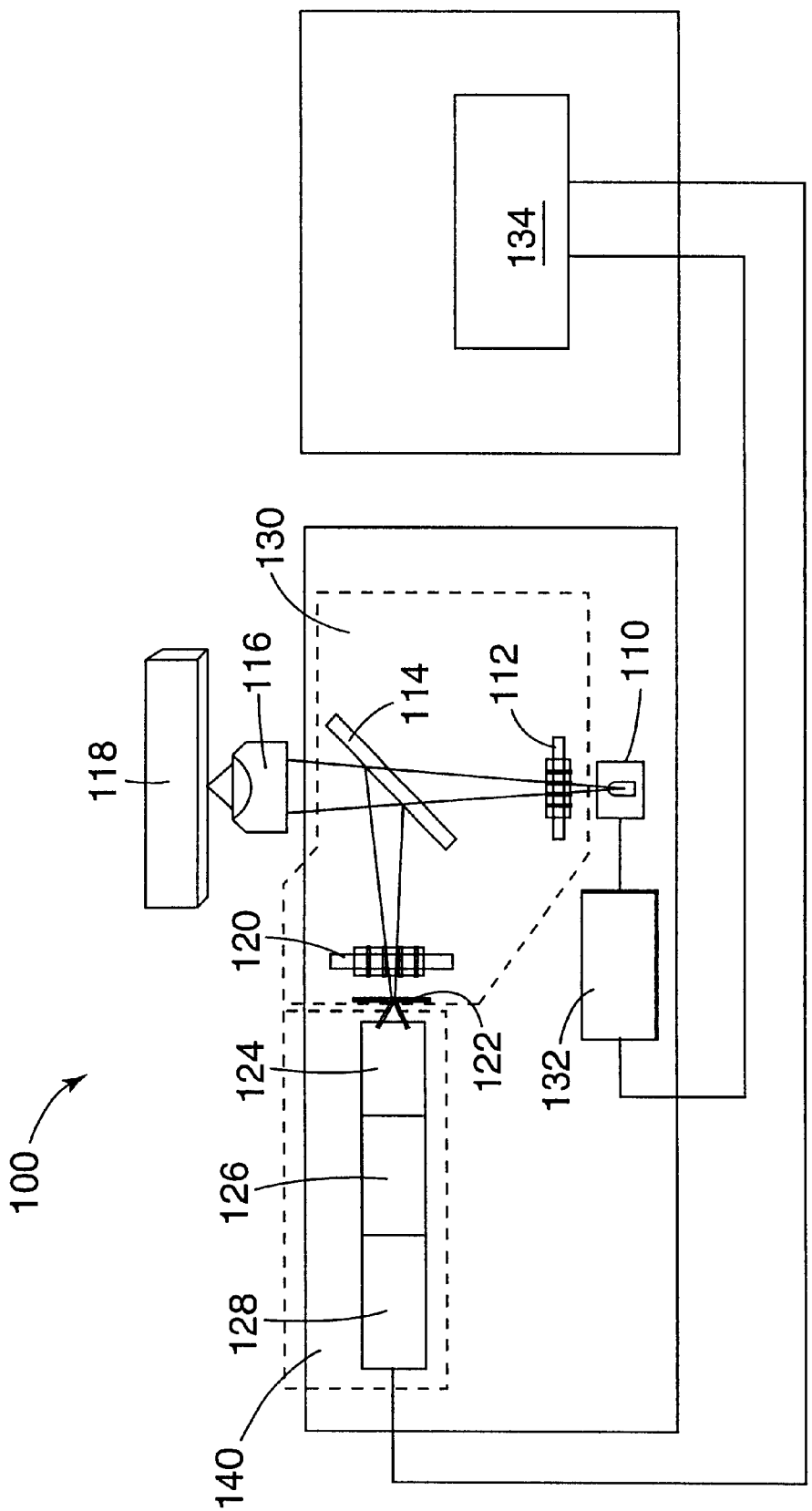
FIG. 15 shows a schematic diagram of an LED based apparatus used to detect enzymatic cleavage of α-TUGlc, β-TUGlc, and β-TUGal in cuvette experiments and microfluidic chip experiments.

FIG. 15 shows a schematic diagram 100 for an LED-based breadboard used in conjunction with the red-shifted fluorogenic enzyme substrates of the present invention to demonstrate feasibility for LED-based biodetection assays.

LED 110, having a maximum emission at 475 nm (Model HP HLMP CB15, Hewlett Packard Instruments, Palo Alto, Calif.), was driven in a pulsed mode with a 10% duty cycle by computer-controlled pulse generator 132 (Hewlett Packard Instruments). Light from LED 110 was introduced into filter block 130 (Model I3, Leica Microsystems, Inc., Deerfield, Ill.), comprising excitation filter 112 (model BP, 450–490 nm), dichroic mirror 114 (model RKP, reflection short pass at 510 nm), and emission filter 120 (model LP, 515 nm) and focused on an illumination region of sample 118 by objective lens 116. The illumination region was designed to accommodate a solution sample, a microfluidic chip, or other sample that might contain β-TUGlc to be enzymatically cleaved. A 10× objective was used for large detection zones (e.g., solution cuvettes, microwell arrays) and a 40× objective was used for small samples (e.g., 50 μm wide channels in microfluidic chips). Both objective lenses were obtained from Melles Griot, Irvine, Calif. (Model #04 OAS 016; 0.65 N.A.). Return fluorescence was passed through objective lens 116, reflected from dichroic mirror 114 through emission filter 120 and iris diaphragm 122, and detected with photomultiplier tube 124 (PMT Model H5783, Hamamatsu Corp., Bridgewater, N.J.) having an adjustable gain between 0 and 70,000 Amperes/Watt. PMT module 124 was powered by a 15 volt power supply (not shown). Preamplifier 126, operating with a gain of up to 10$^7$ Volts/Amp, converted the current to a potential that was signal-conditioned by 100 kHz low pass filter 128, then digitized by an A/D converter in a Macintosh Quadra™ 800 computer 134. LabView™ 4.0 software (National Instruments, Austin, Tex.), controlled LAB-NB, NB-AO-10 and NB-96 data acquisition, analog output and digital I/O printed circuit boards (not shown).

Example 10
Detection of 3-(2-thienyl)umbelliferone anion

Figure 16:
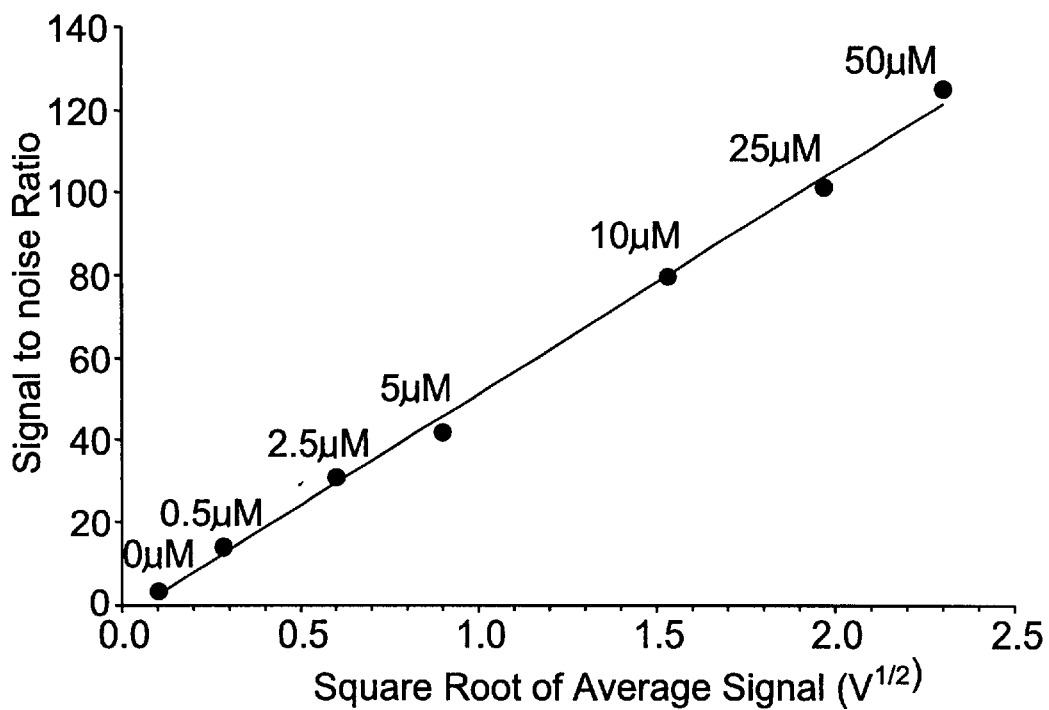
FIG. 16 shows a plot of signal to noise ratio versus the square root of the average signal obtained using the LED apparatus of FIG. 15 for several TU concentrations.

To determine the detection limits and linearity of the testbed described in Example 9, the breadboard was used to detect the 3-(2-thienyl) umbelliferone (TU) anion at concentrations of 50, 25, 10, 5, 2.5 and 0.5 μM in TU. The samples were sequentially transferred into a quartz cuvette that was fixed in position relative to 10× objective 116 (FIG. 15). In this configuration, a 50 μm TU sample provided a 6 pW fluorescent return to PMT 124. With the PMT gain set to 88 Amperes/Watt, the digitized output voltage from the breadboard varied linearly with TU concentration. FIG. 16 shows a plot of signal-to-noise ratio (SNR) vs. the square root of the average signal, in volts, for all of the TU concentrations. Under these conditions, the TU anion was detectable at a concentration as low as 0.5 μM.

The linear relationship shown in FIG. 16 was consistent with a white noise model. According to one theory, the SNR can be increased by a factor of 100 at a given TU concentration by decreasing the bandwidth of the detected signal from 100 KHz (as in the system of the invention) to approximately 10 Hz. Further improvements in SNR can be made by signal averaging. For example, a 100-point boxcar average will produce a 10-fold improvement in SNR. Thus, it may be possible to replace the PMT detector (at a gain of 88 A/W) with a compact photodiode detector (at a gain of 0.3 A/W) while achieving detection limits of 1 μM TU.

Example 11
LED-Based Sterilization Monitoring Using Enzymatic Cleavage of β-TUGlc Two stock solutions of β-glucosidase (Sigma Chemical Co., St. Louis, Mo.) were prepared in pH 7.6 phosphate buffered saline (PBS): (a) 1 enzyme unit/20 μL and (b) 1 enzyme unit/400 μL, where one enzyme unit liberates 1 μMole of product per minute when salicin is the substrate. Required amounts of the stock solutions were diluted with 980 μL of PBS to create samples of 0.5, 0.125, 0.0625, 0.025, and 0.0125 units per mL, represented in FIG. 17a by traces 1 through 5, respectively. These samples were incubated for 7 minutes at 37° C., then treated with 5 μL of 24.6 mM β-TUGlc in DMF (Example 1) such that the initial concentration of β-TUGlc was 123 μM.

Figure 17A:
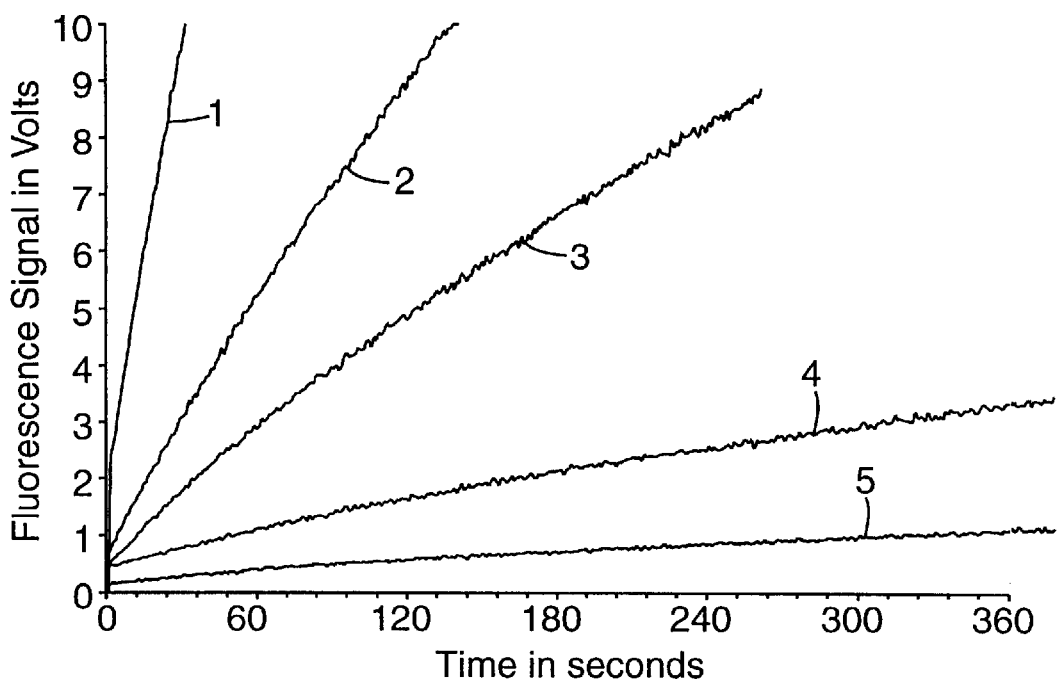
FIG. 17a shows a plot of the detector response versus time of the LED apparatus of FIG. 15, when used to monitor the cleavage of β-TUGlc by various concentrations of β-glucosidase
Figure 17B:
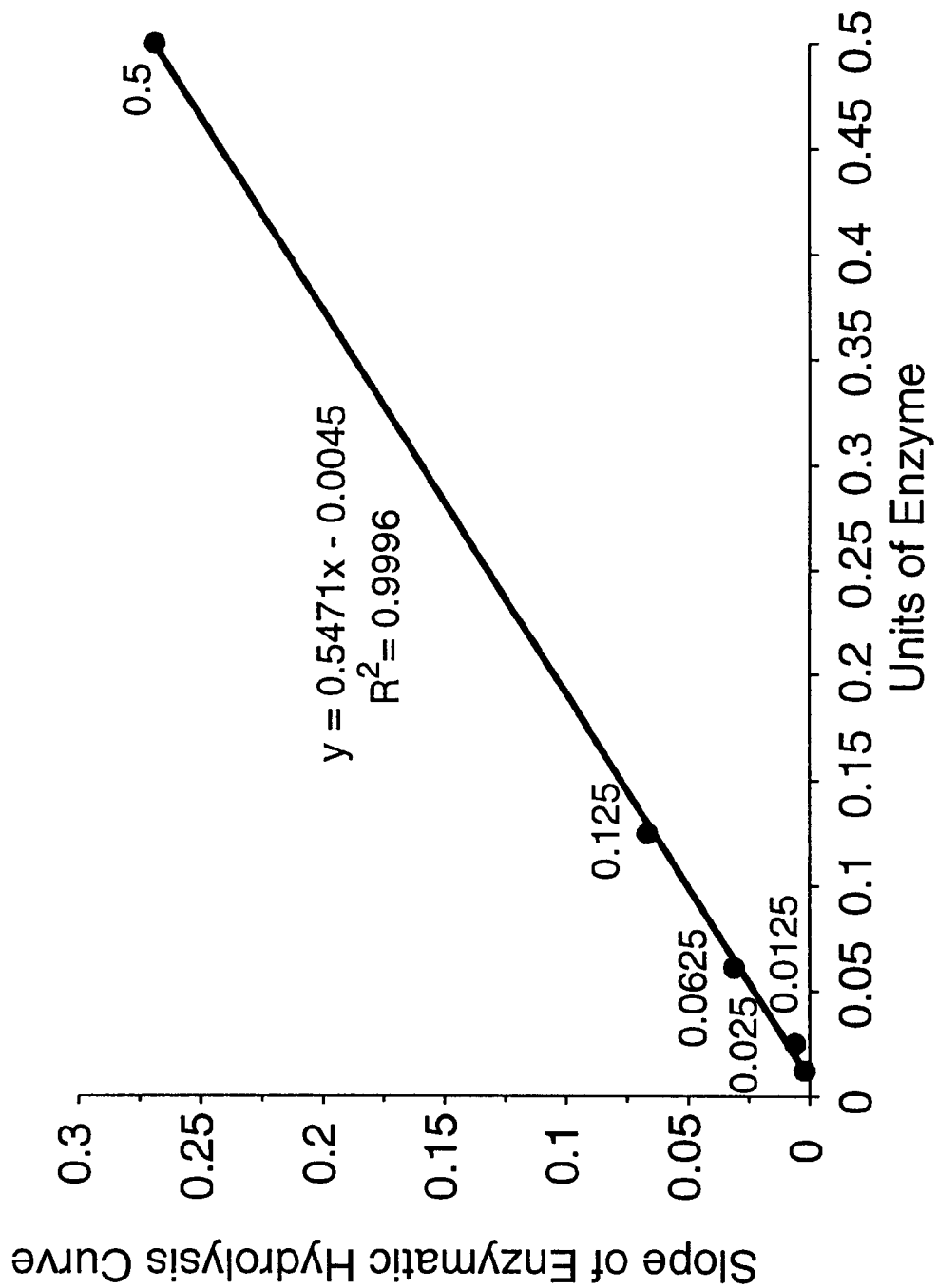

Fluorescence resulting from cleavage of the substrate was monitored in a thermostatted cuvette at 37° C. using the testbed described in Example 9 with a PMT gain setting of 822 Amperes/Watt. Fluorescent response for each enzyme concentration was monitored for three minutes. A graph of the fluorescence signal vs. time is shown in FIG. 17a. FIG. 17b is a plot of the initial rates of reaction obtained from the data in FIG. 17a. FIG. 17b shows a linear dependence of initial rate on enzyme concentration.

Data from this Example show that a significant, detectable fluorescent signal was obtained using the testbed configuration of Example 9 in less than 5 seconds in the presence of 0.5 enzyme units, and that the signal is linear with enzyme concentration in the first 5 minutes. The data of this Example showed that a presumptive positive detection of enzyme was obtained in seconds and a confirmative result was obtained in minutes, very much faster than art-known methods. Control experiments in which similarly prepared enzyme solutions were first steam-sterilized at 121° C. for 20 minutes showed no time-dependent changes in the fluorescent signal, consistent with sterilizer-induced loss of enzyme activity. Therefore, a sterilization indicator system based on the fluorescent enzyme substrates of the present invention, optionally using a compact LED-based detection system, can be constructed.

Figure 18:
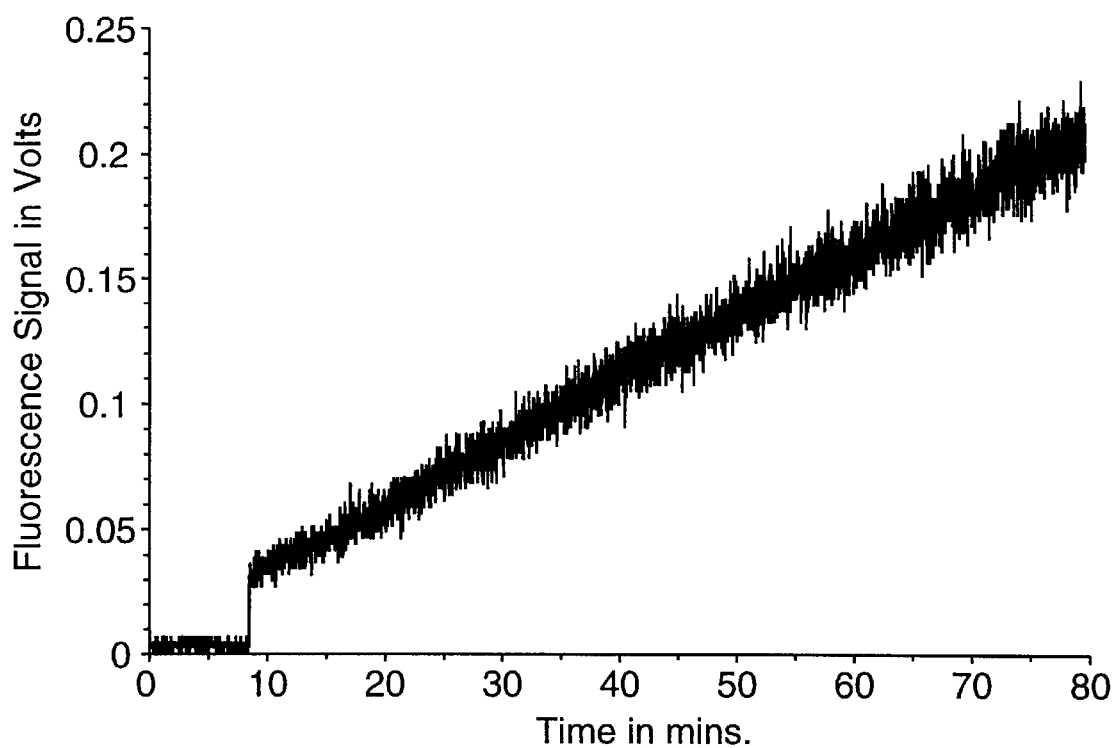
FIG. 18 shows a time plot of the fluorescence signal for the cleavage of β-TUGlC by *Bacillus subtilus* (*B. subtilus*) at $10^8$ spores/mL, measured with the LED apparatus for FIG. 15.

Example 12
LED-Based Sterilization Monitoring Using Bacterial Cleavage of β-TUGlc A mixture comprising 100 μL of $10^9$ spores/mL of *Bacillus subtilis* (commercially available as ATCC 9372 from American Type Culture Collection, Rockville, Md.) in 895 μL of *B. subtilis* growth media (growth media was as described in U.S. Pat. No. 5,795,730, Example 1, incorporated herein by reference) was incubated at 37° C. for 7 minutes, then treated with 5 μL of 24.6 mM β-TUGlc in DMF (Example 1). Fluorescence of the TU anion resulting from enzymatic cleavage was monitored over a two-hour period using the testbed described in Example 9, using a PMT gain of 88 Amperes/Watt and a 10× objective lens. Fluorescence data shown in FIG. 18 indicated that a presumptive identification of *B. subtilis* occurred in less than five minutes after the mixing step, which occurred at the 8-minute mark in FIG. 18. Control experiments in which similarly prepared enzyme solutions were first steam-sterilized at 121° C. for 20 minutes showed no time-dependent changes in the fluorescent signal, consistent with sterilizer-induced loss of enzyme activity. According to one theory, the SNR can be increased by a factor of 100 at a given TU concentration by decreasing the bandwidth of the detected signal from 100 KHz (as in the system of the invention) to approximately 10 Hz. Further improvements in SNR can be made by signal averaging. For example, a 100-point boxcar average will produce a 10-fold improvement in SNR. Thus, it may be possible to replace the PMT detector (at a gain of 88 A/W) with a compact photodiode detector (at a gain of 0.3 A/W) while achieving detection onset times similar to those shown in FIG. 18.

Example 13
Autoclave Stability of β-TUGlc

Solutions of 0.1 g/mL of β-TUGlc (Example 1) in *B. subtilis* growth media and in pH 7.6 phosphate buffered saline (PBS) were heated in an autoclave for 20 minutes at 121° C. Fluorescence spectrum on excitation at 362 nm was obtained. The sample was heated a second time in an autoclave for 15 minutes at 132° C., and the fluorescence spectrum was obtained. Analysis of the fluorescence spectra indicated that approximately 10% of the β-TUGlc had been hydrolyzed during each autoclave cycle. Therefore, β-TUGlc was sufficiently robust to be used in a sterilization indicator format such as a Attest™ Rapid Readout Biological Indicator (3M Company, St. Paul, Minn.), wherein the fluorogenic enzyme substrate and the biological spore are both exposed to the conditions within the steam sterilizer.

Example 14
Hand-Held Sterilization Monitor Probe

A solution of 100 μL of 1.0 mM β-TUGlc (Example 1) in DMF was combined with 840 μL of 7.6 pH PBS in a 1 mL cuvette, and the volume was adjusted to 990 μL by the addition of 50 μL of 30 mM aq. MgCl. The mixture was irradiated using a GaN LED ($\lambda_{max}$=480 nm, Nichia Chemical Industries, Ltd., Anan, JP) mounted in a compact, hand-held probe, and 10 μL of β-glucosidase (0.125 units in pH 7.6 PBS) was added. Within ten seconds, a strong fluorescent signal could be seen in the cuvette. After five minutes, the solution in the cuvette had turned from colorless to green, in addition to exhibiting strong fluorescence, indicating that the TUG dye was useful as a visible indicator as well as a fluorescent indicator.

In addition to housing an LED, the probe can be configured to include fiber optics modules for collecting fluorescent emissions and routing them to a detector or other attached devices. Alternatively, the probe can be configured to hold an optical fiber or fiber bundle that delivers an LED excitation signal from a remote source.

Example 15
Fluid Control Film Based Sterilization Monitor

In this example, a plastic fluid control film microstructured with parallel V-groove channels was derivatized with an azlactone functional polymer that served to covalently attach the sterilization indicating enzyme β-D-glucosidase. Enzyme activity was retained as indicated by wicking a buffered solution of β-TUGlc into the channels and noting a rapid development of enzyme cleaved fluorescent product. However, exposure of an enzyme derivatized chip to a steam sterilization cycle resulted in total loss of enzyme activity, as indicated by a lack of fluorescent signal upon wicking of a β-TUGlc solution. Details of the experiment are given below.

Microchannels were extrusion embossed in an impact-modified polypropylene/polyethylene copolymer film (SRD-7560 resin, Union Carbide Corp., Danbury, Conn.) as described in U.S. Pat. No. 5,514,120, Example 1, incorporated herein by reference. For the example cited below, an embossing tool was used that produced microchannel film with a "V channel" cross-section profile. The microchannels had a triangular cross-section with a base of approximately 0.3 mm and a height of approximately 0.35mm.

An azlactone functional polymer and β-D-glucosidase enzyme were applied to the V-groove channels as follows. Channel arrays were cut into 5 cm lengths, dipped in a 2% priming solutions referred to below as "Universal Primer," dried for 10 minutes at 80° C., cooled to room temperature, dip coated in a coating solution containing azlactone functional polymer (70% methylmethacrylate:30% vinyl dimethylazlactone copolymer mixed 2% in methyl ethyl ketone solvent, prepared as described in U.S. Pat. No. 5,292,840, Example 43, incorporated herein by reference), and air dried for 30 minutes. The channels were treated for 90 minutes at room temperature with a stock solution of β-glucosidase (Sigma Chemical Co., St. Louis, Mo.; pH 7.6 phosphate buffered saline PBS); specific activity of 1 enzyme unit/20 uL).

The composition of the undiluted "Universal Primer" (described in U.S. Pat. No. 5,602,202, Example 15, incorporated herein by reference) was as follows (one gallon basis): 15 g Kraton 1901X (maleated Kraton rubber, Shell Chemical Co., Houston, Tex.), 61.3 g CP 343-3 (chlorinated polypropylene @ 50% solids, Eastman Chemical Co., Kingsport, Tenn.), 10 g EPON 828 epoxy resin (Shell Chemical Co.), 10 g silane coupling agent A-186 (OSi Specialties, Endicott, N.Y.), 1106 g cyclohexane, and 679 g xylenes, mixed for 30 min at 67° C. To this was added 120.2 g 79/20/1 Isooctyl acrylate/n-vinyl caprolactam/acrylic acid copolymer (40% by weight in ethyl acetate), 5 g triethanolamine chelate of tetraisopropylalcohol titanate, available as Taizer TE™ (Dupont Chemical Co., Wilmington, Del.), 200g ethanol, and 18 g xylenes, with mixing. The "Universal Primer" was diluted from a 5% solution to a 2% solution in cyclohexane before application to the microchannel film.

Enzyme-derivatized fluid control film was examined to determine if the enzyme activity could be used to indicate effective sterilization. Samples of the film with and without enzyme were exposed to a steam sterilization cycle for 5 minutes at 121° C. Control films with and without enzyme were stored at room temperature. After sterilization, films were treated by wicking up an assay solution of 123 uM β-TUGlc in PBS buffer pH 7.6 and monitoring for fluorescent return using a GaN LED source. The results are summarized in Table 4.

TABLE 4

| Sample | Generation of fluorescent product |
|---|---|
| Film with enzyme-5 min. at 121° C. | − |
| Film with enzyme-23° C. | + |
| Film without enzyme-5 min. at 121° C. | − |
| Film without enzyme-23° C. | − |

These results indicate that enzyme activity is stable on the fluid control film, but is destroyed by the sterilization procedure as desired for a presumptive sterilization indicator.

Example 16
Laser Induced Thermal Imaging of Biomolecules in a Predefined Pattern Laser Induced Thermal Imaging (LITI) donor sheet consisting of an azlactone hydrogel layer comprising covalently bound β-D-glucosidase enzyme, a polyacrylate interlayer, and a carbon black light-to-heat conversion layer was prepared on a polyethylene terephthalate support. The donor sheet was prepared as follows:

The light-to-heat conversion layer was prepared by coating an aqueous dispersion of carbon black in a radiation curable resin onto a 0.1 mm thick PET substrate with a Yasui Seiki Lab Coater, Model CAG-150 (Yasui Seiki Co., Bloomington, Ind.) using a microgravure roll of 90 helical cells per lineal inch. The coating composition was 1 part trimethylolpropane triacrylate (Sartomer™ SR351 HP, Sartomer Co. Inc., Exton, Pa.), 1.15 parts 3M Matchprint Negative Black Millbase (3M Co., St. Paul, Minn.), and 5% 2-hydroxy-2,2-dimethylacetophenone photoinitiator (Darocur™ 1173, Ciba Specialty Chemicals Co., Tarrytown, N.Y.). The coating was subsequently in-line dried and UV-cured on the PET support. The transmission optical density (TOD=−logT, where T is the measured fractional transmission) of the coated film was 2.35 at 1060 nm.

The polyacrylate interlayer was prepared as a 20% solids solution of 130 g trimethylolpropane triacrylate (Sartomer™ SR351 HP), 130 g of a 3:1 mixture (25% solids w/w/) with polyvinyl butyral (Butvar™ B98, Monsanto Co., St. Louis, Mo.), 221 g 1-methyl-2-propanol, 8.13 g Darocur™ 1173 in 331.5 g methyl ethyl ketone, which was then coated onto the light-to-heat conversion layer at a thickness of from 1.0 to 1.2 μm and cured with actinic radiation via exposure in a Radiation Polymer Corporation (Plainfield, Ill.) UV Processor Model No. QC 1202AN3TR (medium pressure UV lamp, total exposure ca. 100 millijoules/cm$^2$, N$_2$ atmosphere) to produce an interlayer.

A 40% (w/w) solution of 60:40 (w/w) DMA/VDM copolymer (prepared as described in Example 17, using 56 parts DMA and 84 parts VDM) solid was prepared in cyclohexanone. The residue resulting from drying 28 mg of a 30% aqueous suspension of 2,6-bis(4-azidobenzylidene)-4-methyl cyclohexanone (BAMC) crosslinker was taken up in 2 mL of the polymer-cyclohexanone solution, and the resulting mixture was hand spread onto the interlayer under reduced lighting conditions, at a target coating thickness of 5 μm to complete the LITI donor substrate. The resulting azlactone hydrogel coating was treated at various locations with a 1 mg/mL solution of β-D-glucosidase enzyme in 50 mM sodium phosphate buffer pH 7.6 and allowed to dry. This provided covalent attachment of the enzyme to the azlactone transfer layer of the donor sheet construction via reaction of reactive pendant groups on the enzyme with the azlactone functionality of the hydrogel composition.

Material was transferred by LITI to a polyvinylidene chloride-primed PET receptor sheet. The LITI apparatus used a YAG laser (Model 2600 from Control Laser Corporation, Orlando, Fla.) operated in the continuous wave (cw) mode. The cw output beam was incident on a model 1201E-2 acousto-optic modulator (AOM) driven by a model 21A radio frequency (RF) driver, both from Isomet Corporation, Springfield, Va. The component of the YAG laser beam diffracted into the first order by the AOM was selected by an aperture and focused to a 100 μm diameter spot with a three element, 2.5" focal length objective lens. The LITI donor sheet in contact with the glass receptor was placed at the focus of the objective lens on a, model number ATS50030 xy translation stage from Aerotech Inc., Pittsburgh, Pa. The RF driver for the AOM was gated on and off with a model 8116A function generator from Hewlett-Packard, Santa Clara, Calif. In this way different areas of the LITI donor sheet/receptor combination were moved into the laser beam and the laser beam turned on and off to produce optical pulses with pulse widths in the range of 0.1–100 msec. Absorption of these laser pulses by the donor sheet resulted in rapid heating of the above-described DMA/VDM copolymer layer and thermal transfer of the copolymer-plus-enzyme to the receptor.

In this case, 100 μm wide stripes with 100 μm spacing were imaged onto the receptor and subsequently crosslinked. Some stripes corresponded to regions of the donor sheet where enzyme had been applied. Some stripes corresponded to control regions where no enzyme was applied. The entire receptor sheet was innoculated with a 0.05 mM solution of 4 methyl-umbelliferyl-β-D-glucoside indicator that becomes fluorescent as a result of enzymatic cleavage by β-D-glucosidase enzyme. The resulting fluorescent pattern was imaged with a CCD camera mounted on a Leica Model DMRX epifluorescence microscope. As a control, a second sample was exposed to a steam sterilization cycle (5 minutes at 121° C.) to kill the enzyme activity. This sample gave no detectable fluorescent image when treated with TUGlc. Both images were digitized and transmitted over a LAN to a research database along with information pertaining to sample identification.

Example 17
Preparation of 1:1 dimethylacrylamide:vinyl dimethylazlactone (DMA:VDM) copolymer A solution of 70 parts dimethylacrylamide (DMA) and 70 parts 2-vinyl-4,4-dimethyl-2-oxazoline-5-one (vinyldimethylazlactone, VDM, commercially available from SNPE, Princeton, N.J.) in 210 parts methyl ethyl ketone (MEK) was mixed with 0.7 parts N, N'-azobis (isobutyronitrile) initiator (AIBN, commercially available as VAZO 64™, Wako Chemicals USA, Inc., Richmond, Va.). The mixture was sparged with nitrogen for 5 minutes, then sealed in ajar and tumbled in a lauderometer water bath at 60° C. for 24 hours. The resulting reaction mixture was shown gravimetrically to have 40.6% solids by evaporation of a sample at 120° C. for 3 hours.

Example 18

Synthesis of Covalently Attachable FES (3-[2'-(5'-carboxy)-furyl]-umbelliferyl)-β-D-galactoside)

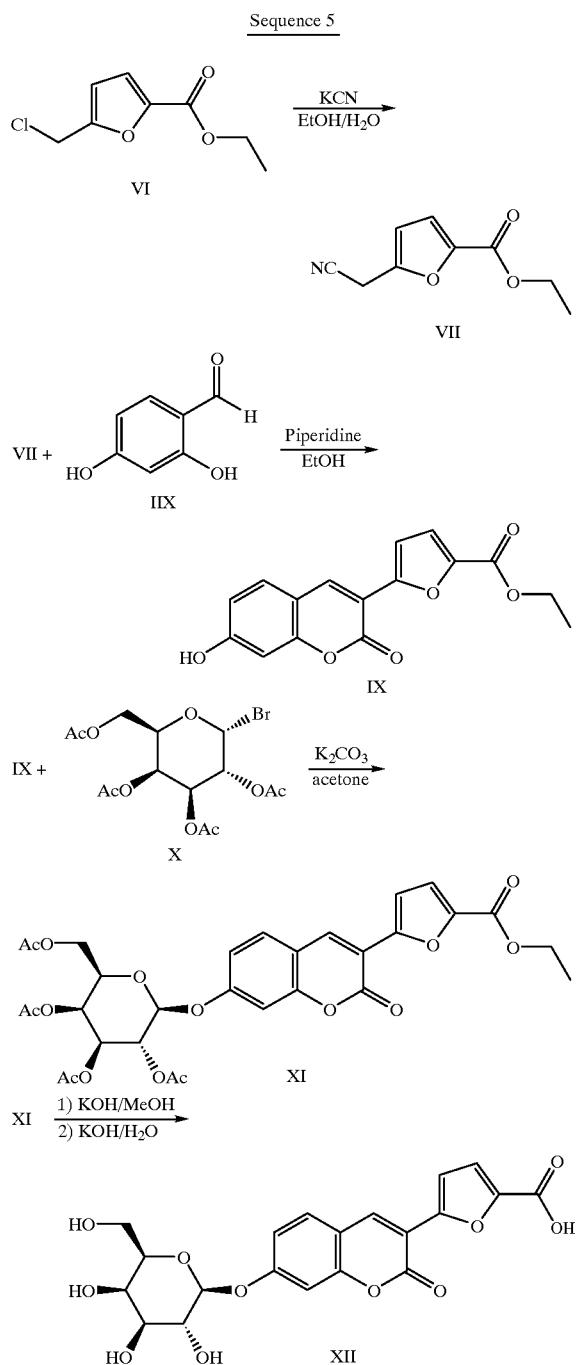

Sequence 5 shows the synthetic scheme for preparing FES (3-[2'-(5'-carboxy)-furyl]-umbelliferyl)-β-D-galactoside.

The free carboxy group provides a site for covalent attachment to a polymer or to a macromolecule. Covalent attachment to a polymer is described, for example in copending U.S. patent application Ser. No. 5,958,782, incorporated herein by reference.

Ethyl-(5-cyanomethyl)-2-furoate (VII)

A solution of ethyl-(5-chloromethyl)-2-furancarboxylate (VI, 50 g) in ethanol (80 mL) was added to a solution of potassium cyanate (18 g) in water (40 mL) and the mixture was refluxed for 3 hours. After cooling to room temperature, the solution was poured into water (300 mL) and extracted three times with ether. The combined organic layers were washed with brine and dried over $MgSO_4$. Removal of solvent under vacuum gave a crude thick brown oil which was purified by column chromatography on silica gel using ethyl acetate/hexane (1:4) to give VII as a yellow solid (31.4 g). The structure of the product was confirmed by NMR.

3-[2'-(5'-carboethoxy)-furyl]-umbelliferone (IX)

To a solution of ethyl-(5-cyanomethyl)-2-furoate (VII, 1.00 g) and 2,4-dihydroxybenzaldehyde (VII, 0.77 g) in ethanol (20 mL), was slowly added piperidine (1.44 g). The solution turned dark green/black, and was refluxed for 17 hours. The solution was cooled to room temperature and concentrated HCl (4 mL) was added. The ethanol was removed under vacuum, and the dark solid was dissolved in warm 20:80 ethanol:water (40 mL), and allowed to slowly cool. The brown solid IX (1.50 g) was collected by filtration and dried under vacuum. The structure of the product was confumed by NMR.

(3-[2'-(5'-carboethoxy)-furyl]-umbelliferyl)-2,3,4,6-tetra-O-acetyl-β-D-galactoside (XI)

Potassium carbonate (20.0 g) was added to a solution of 3-[2'-(5'-carboethoxy)-furyl]-umbelliferone (IX, 8.50 g) and acetobromo-α-D-galactose (X, 11.64 g) in acetone (250 mL). The mixture was stirred for 3 days at room temperature (23° C.) under nitrogen. The acetone was then removed under vacuum, and water (50 mL) was added to dissolve the potassium carbonate. The product was extracted with ethyl acetate and the combined organic layer was dried over $MgSO_4$. The solvent was removed under vacuum, and the product was purified by column chromatography on silica gel using ethyl acetate/hexane (1:1) to give VI as a yellow solid (11.00 g). The structure of the product was confirmed by NMR.

(3-[2'-(5'-carboxy)-furyl]-umbelliferyl)-β-D-galactoside (XII)

To a solution of tetra-O-acetyl-β-D-galactoside (XII, 1.00 g) in methanol (10 mL) was added of a 1M aqueous solution of KOH (8.7 mL) dropwise over 5 minutes. The resulting solution was stirred for 4 hours at room temperature. Methanol was then removed under reduced pressure, and the resulting solution was heated to 65° C. for 5 h. The solution was cooled to 0° C. and brought to pH 3 by the addition of 1M HCl (aq). The resulting solids were collected by filtration and dried under reduced pressure, to give 0.21 g XII as a yellow solid. The structure of the product was confirmed by NMR.

The above specification, examples and data provide a complete description of the manufacture and use of the compositions of the invention. Since many embodiments of the invention can be made without departing from the spirit and scope of the invention, the invention resides in the claims hereinafter appended.

We claim:
1. A fluarogenic compound of the formula:

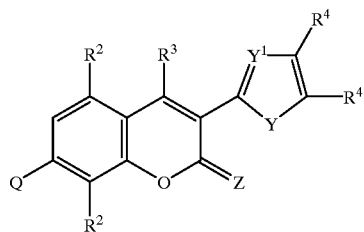

wherein:
- Q is a enzymatically hydrolyzable group selected from the group consisting of a glyconc, a glycosyl phosphate, an ester, and a peptide,
- each $R^2$ independently is a sterically non-interfering group;
- $R^3$ is an electron withdrawing or non-electron withdrawing group;
- Z is O or $NR^5$, wherein $R^5$ is hydrogen or a hydrocarbyl-containing group;
- Y and $Y^1$ independently are O, S, $NH_x$, or $CH_y$ where x is 0 or 1 and y is 1 or 2, and at least one of Y and $Y^1$ is O, S, or $NH_x$; and
- each $R^4$ independently is selected from the group consisting of hydrogen and carboxyl;

or a salt thereof.

2. A compound according to claim 1, wherein
each $R^2$ independently is selected from the group consisting of: hydrogen, halogen, a $C_1$–$C_{20}$ alkyl, a $C_1$–$C_{20}$ alkoxy, a $C_2$–$C_{18}$ alkenyl, a $C_1$–$C_{20}$ hydrocarbylamino, a $C_2$–$C_{20}$ di(hydrocarbyl)amino, and a group having the formula $(CH_2A)_aE$ in which A is O, NH, or a single bond, E is a functional group that includes active hydrogen, and a is a whole number from 1 to 100; and $R^3$ is selected from the group consisting of: hydrogen, a $C_1$–$C_{20}$ alkyl, a $C_3$–$C_{18}$ cycloalkyl, a $C_6$–$C_{18}$ aryl, a $C_6$–$C_{18}$ aryloxy, a $C_6$–$C_{18}$ hydroxyaryl, a $C_6$–$C_{18}$ arylcarboxy, a $C_6$–$C_{18}$ carboxyaryl, a $C_2$–$C_{18}$ alkenyl, a $C_2$–$C_{18}$ alkynyl, a halogen selected from the group consisting of F, Cl, Br, and I, a $C_1$–$C_4$ haloalkyl, a cyano, a $C_1$–$C_6$ cyanoalkyl, a carboxylate, a $C_1$–$C_6$ carboxylalkyl, and a group having the formula $(CH_2A)_aE$ in which A and E are defined as above and a is a whole number from 1 to 100.

3. A compound according to claim 1, wherein:
each $R^2$ independently is selected from the group consisting of: hydrogen, halogen, a $C_1$–$C_{10}$ alkyl, a $C_1$–$C_{10}$ alkoxy, a $C_2$–$C_{10}$ alkenyl, a $C_1$–$C_{10}$ alkylamino, a $C_1$–$C_{10}$ dialkylamino, and a group having the formula $(CH_2A)_aE$ in which A is O, NH, or a single bond, E is a functional group that includes active hydrogen, and a is a whole number from 1 to 100; and $R^3$ is selected from the group consisting of: hydrogen, a $C_1$–$C_{10}$ alkyl, a $C_5$–$C_8$ cycloalkyl, a $C_6$–$C_{10}$ aryl, a heterocyclic group comprising at least one O, N or S atom, a $C_2$–$C_{10}$ alkenyl, chloromethyl, a $C_2$–$C_{10}$ alkynyl, a halogen selected from the group consisting of F, Cl, and Br, a $C_1$–$C_4$ haloalkyl, a cyano, a $C_1$–$C_6$ cyanoalkyl, a carboxylate, a $C_1$–$C_6$ carboxylalkyl, and a group having the formula $(CH_2A)_aE$ in which A and E are defined as above and a is a whole number from 1 to 25.

4. A compound according to claim 1, wherein Z is O or $NR^5$, where $R^5$ is hydrogen or a $C_1$ to $C_4$ alkyl group.

5. A compound according to claim 1, wherein each $R^2$ and $R^3$ are hydrogen.

6. A compound according to claim 1, wherein each $R^4$ independently is selected from the group consisting of hydrogen, halogen, carboxyl, carboxamide, ester, keto-alkyl ester, sulfonic acid, amino, and a group of the formula $(CH_2A)_aE$ in which A is O, NH, or a single bond, E is a functional group that includes active hydrogen, and a is a whole number from 1 to 25; or both $R^4$ groups together with the carbon atoms to which they are attached form a 6-membered aromatic ring which optionally has one or two $R^4$ groups attached.

7. A compound according to claim 1, wherein:
Z is O;
each $R^2$ and $R^3$ are hydrogen; and
each $R^4$ independently is selected from the group consisting of hydrogen, halogen, carboxyl, carboxamide, ester, keto-alkyl ester, sulfonic acid, amino, and a group of the formula $(CH_2A)_aE$ in which A is O, NH, or a single bond, E is a functional group that includes active hydrogen, and a is a whole number from 1 to 10; or both $R^4$ groups together with the carbon atoms to which they are attached form a 6-membered aromatic ring which optionally has one or two $R^4$ groups attached.

8. A compound according to claim 1, wherein Q is a carboxy terminal-linked peptide having 1 to 4 amino acids, wherein free amino groups optionally have a protective group, or an acid addition salt thereof.

9. A compound according to claim 1, wherein Q is a carboxy terminal-linked amino acid, or an acid addition salt thereof.

10. A compound according to claim 1, wherein Q is a monosaccharide glycone or a disaccharide glycone.

11. A compound according to claim 1, wherein Q is selected from the group consisting of α- and β-D-galactopyranosyl; α- and β-D glucopyranosyl; N-acetyl-α- and β-D-galactosaminyl; N-acetyl-α- and β-glucosaminyl; β-D-glucuronyl; α-L-arabinopyranosyl; α-L-arabinofaranosyl; β-D-facopyranosyl; α- and β-L-fucopyranosyl; α-D-mannopyranosyl; β-D-xylopyranosyl; α-D-maltosyl; β-D-lactopyranosyl; β-D-cellobiosyl; α-d-N-acetylneuraminyl; and myoinositol-1-yl phosphate.

12. A compound according to claim 1, wherein Q is a peptide selected from the group consisting of N-acetyl-L-lysine, L-alanine, L-arginine, L-arginyl-L-arginine, L-aspartic acid, N-alpha-benzyloxycarbonyl-L-arginine, N-benzyloxycarbonyl-glycyl-L-proline, L-citrulline, gamma-L-glutamic acid, L-glutaryl-glycyl-arginine, L-glycine, glycyl-glycine, glycyl-L-phenylalanine, glycyl-L-proline, L-histidine, L-hydroxproline, L-isoleucine, L-leucine, L-lysine, L-methionine, L-ornithine, L-phenylalanine, L-proline, L-pyroglutamic acid, L-serine, L-seryl-L-tyrosine, L-tryptophan, L-tyrosine, and L-valine.

13. A compound according to claim 11, wherein Q is selected from the group consisting of α- and β-D-galactopyranosyl, α- and β-D-glucopyranosyl, and β-D-glucurosyl.

14. A compound according to claim 1 wherein Q is an ester.

15. A compound according to claim 1, wherein said compound is stable when exposed to a temperature of 121° C. for 5 minutes.

16. A compound according to claim 1, wherein the product obtained by hydrolysis of Q exhibits a wavelength of maximum absorbance of at least about 380 nm.

17. A compound according to claim 16, wherein the hydrolysis is carried out by an enzyme selected from the group consisting of a glycosidase, a peptidase, an esterase, and combinations thereof.

* * * * *

UNITED STATES PATENT AND TRADEMARK OFFICE
CERTIFICATE OF CORRECTION

PATENT NO.   : 6,372,895 B1
DATED        : April 16, 2002
INVENTOR(S)  : Bentsen, James G.

It is certified that error appears in the above-identified patent and that said Letters Patent is hereby corrected as shown below:

Column 1,
Line 17, "calorimetric" should be -- colorimetric --

Column 2,
Line 16, "405 mn" should be -- 405 nm --

Column 5,
Line 41, "hydroxyaryl" should be -- hydroxyaryl, a --

Column 6,
Line 58, "wherein $\lambda_1$ is at least 10 nm greater than $\lambda_1$, $\lambda_2$" should be -- $\lambda_2$ is at least 10 nm greater than $\lambda_1$, $\lambda_1$, --

Column 9,
Line 9, "cleavage of (α-TUGlc by" should be -- cleavage of α-TUGlc by --
Line 26, cleavage of (β-TUGlC by" should be -- cleavage of β-TUGlc by --

Column 11,
Line 30, "$\lambda_{cm}$ (nm)" should be -- "$\lambda_{em}$ (nm) --

Column 12,
Line 30, "facopyranosyl," should be -- fucopyranosyl, --

Column 14,
Line 44, "Coniugates" should be -- Conjugates --

Column 20,
Line 34, "(α-D-glucosidase" should be -- α-D-glucosidase --
Line 63, "tinder" should be -- under --

Column 21,
Line 60, "inumunohistochemical" should be -- immunohistochemical --

Column 31,
Line 3, "farther" should be -- further --
Replace the last chemical structure identified as number IV

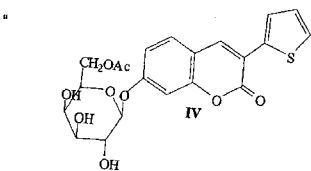 should be -- 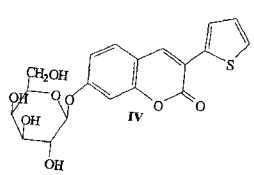 --

UNITED STATES PATENT AND TRADEMARK OFFICE
CERTIFICATE OF CORRECTION

PATENT NO. : 6,372,895 B1
DATED : April 16, 2002
INVENTOR(S) : Bentsen, James G.

It is certified that error appears in the above-identified patent and that said Letters Patent is hereby corrected as shown below:

Column 33,
Line 1, "tetra-O-acetl" should be -- tetra-O-acetyl --
Line 53, "D-zalactoside (β-TUGab)" should be -- D-galactoside (β-TUGal) --
Line 63, "3-(2-thienyb)-umbelliferyl-7-β-D-lucoside" should be -- 3-(2-thienyl)-umbelliferyl-7-β-D-glucoside --

Column 34,
Line 44, "thioketopropnaloic" should be -- thioketopropanoic --
Line 53, "hydroxylarnine" should be -- hydroxylamine --

Column 35,
Line 31, "techinique." should be -- technique. --

Column 36,
Line 20, "β-TUGlC" should be -- β-TUGlc --

Column 37,
Line 26, "β-Glucosidase" should be -- β-Glucosidase --
Line 33, "Attest#" should be -- Attest$^{TM}$ --

Column 38,
Line 28, "acetochloro-α-D-glucose" should be -- acetochloro-β-D-glucose --

Column 39,
Line 2, "*Escierichia*" should be -- *Escherichia* --
Line 54, "103" should be -- $10^3$ --

Column 40,
Line 31, "Petrifihm" should be -- Petrifilm --

Column 41,
Line 24, "limole of" should be -- $\mu$mole of --

Column 44,
Line 54, "saline PBS);" should be -- saline –(PBS); --

Column 47,
Line 1, "ajar" should be -- a jar --

Column 49,
Line 2, "fluarogenic" should be -- fluorogenic --
Line 16, "glyconc" should be -- glycone --

UNITED STATES PATENT AND TRADEMARK OFFICE
CERTIFICATE OF CORRECTION

PATENT NO. : 6,372,895 B1
DATED : April 16, 2002
INVENTOR(S) : Bentsen, James G.

It is certified that error appears in the above-identified patent and that said Letters Patent is hereby corrected as shown below:

Column 50,
Line 37, "arabinofaranosyl; β-D-facopyranosyl;" should be -- arabinofuranosyl; β-D-fucopyranosyl; --

Signed and Sealed this

Twenty-sixth Day of August, 2003

JAMES E. ROGAN
*Director of the United States Patent and Trademark Office*